(12) United States Patent  
Song et al.

(10) Patent No.: US 7,705,004 B2
(45) Date of Patent: Apr. 27, 2010

(54) PROTEIN KINASE INHIBITORS

(75) Inventors: Yonghong Song, Foster City, CA (US); Qing Xu, Foster City, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 61 days.

(21) Appl. No.: 12/192,034

(22) Filed: Aug. 14, 2008

(65) Prior Publication Data

US 2009/0054425 A1 Feb. 26, 2009

Related U.S. Application Data

(60) Provisional application No. 60/956,643, filed on Aug. 17, 2007.

(51) Int. Cl.
C07D 487/04 (2006.01)
A61K 31/519 (2006.01)

(52) U.S. Cl. .................. 514/265.1; 544/280; 544/105; 514/105

(58) Field of Classification Search .............. 544/280; 514/265.1
See application file for complete search history.

(56) References Cited

FOREIGN PATENT DOCUMENTS

| WO | WO 01/09134 A1 | 2/2001 |
|----|----------------|--------|
| WO | WO 2005/051393 A1 | 6/2005 |
| WO | WO 2007/042298 A1 | 4/2007 |
| WO | WO 2007/042299 A1 | 4/2007 |
| WO | WO 2007/117465 A2 | 10/2007 |
| WO | WO 2008/081928 A1 | 7/2008 |
| WO | WO 2008/119792 A1 | 10/2008 |

*Primary Examiner*—Kahsay T Habte
(74) *Attorney, Agent, or Firm*—Seed IP Law Group PLLC

(57) ABSTRACT

Compounds, particularly compounds having spleen tyrosine kinase (Syk) inhibition activity, having the following structure:

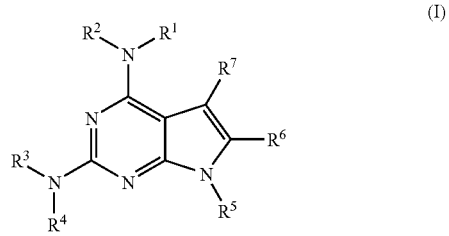

or a pharmaceutically acceptable salt thereof, wherein $R^1$ is structure (a), (b), (c) or (d):

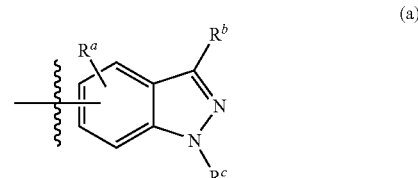

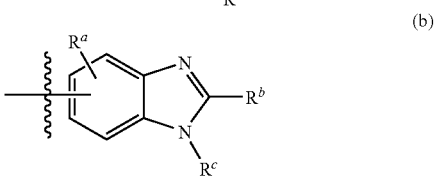

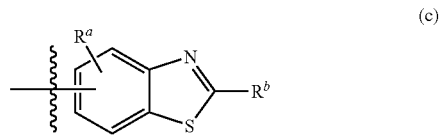

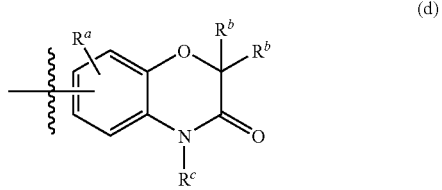

and $R^a$, $R^b$, $R^c$, $R^2$, $R^3$, $R^4$, $R^5$, $R^6$ and $R^7$ are as defined herein. Methods associated with preparation and use of the same, as well as pharmaceutical compositions containing the same, are also disclosed, as well as uses of the same to treat a condition or disorder mediated by a Syk and/or JAK kinase.

17 Claims, No Drawings

PROTEIN KINASE INHIBITORS

CROSS-REFERENCE TO RELATED APPLICATION

This application claims the benefit under 35 U.S.C. § 119(e) of U.S. Provisional Patent Application No. 60/956,643 filed Aug. 17, 2007, which is incorporated herein by reference in its entirety.

BACKGROUND

1. Technical Field

The present invention generally relates to novel compounds, particularly compounds having spleen tyrosine kinase (Syk) and/or JAK kinase inhibition activity, as well as to compositions and methods associated with the same.

2. Description of the Related Art

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there have been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as Syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the syk family of protein tyrosine kinases. The interaction of Syk or ZAP-70 with diphosphorylated ITAM sequences induces a conformation change in the kinases that allows for tyrosine phosphorylation of the kinase itself. Src and Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C) γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via Syk, activate a signaling cascade in mast, basophil, and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of Syk (Rossi, A. B. et al., *J Allergy Clin Immunol.*, 118:749-755, 2006). In immune-thrombocytopenia, antibody bound platelets are cleared by the spleen by an Fc receptor/ITAM/Syk-mediated process (Crow, A. R. et al., *Blood*, 106: abstract 2165, 2005). Drug-induced thrombocytopenia, caused by heparin-platelet factor 4 immune complexes that activate platelet FcγRIIa, also involve Syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. Syk is activated during both phases of integrin signaling, and inhibition of Syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from Syk deficient mouse (Poole, A. et al., *EMBO J.*, 16:2333-2341, 1997). Thus Syk inhibitors may also possess anticoagulation action.

Because of the role Syk plays in Ig-induced platelet activation, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin α2β1.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of Syk. Activation of GPVI leads to induction of multiple platelet functions including: activation of integrins α2β1 to achieve firm platelet adhesion, and GP IIb-IIIa which mediates platelet aggregation and thrombus growth; platelet secretion, allowing for the delivery of inflammatory proteins such as CD40L, RANTES and TGFβ to the vessel wall; and the expression of P-selectin which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from Syk deficient mouse (Crowley, M. T. et al., *J. Exp. Med.,* 186:1027-1039, 1997). This suggests that Syk has a markedly important role in the FcγR-mediated phagocytosis of macrophages. Therefore, it is believed that Syk inhibitors can inhibit cell or tissue damage induced by antibody-dependent cellular cytotoxicity (ADCC).

It has also been reported that an antisense oligonucleotide of Syk suppresses the apoptosis inhibition of eosinophils induced by GM-CSF (Yousefi, S. et al., *J. E. Med.,* 183:1407-1414, 1996), showing that Syk is essential for the life extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.,* 267:8613-8619, 1992; and Takata, M. et al., *EMBO J.,* 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA,* 91:5301-5305, 1994; and Couture, C. et al., *Mol. Cell. Biol.,* 14:5249-5258, 1994). Syk is present in mature T-cell populations, such as intraepithelial γδ T-cells and naïve ad T-cells, and has been reported to be capable of phosphorylation of multiple components of the TCR signaling cascade (Latour, S. et al., *Mol Cell Biol.,* 17:4434-4441, 1997). As a consequence, Syk inhibitors may serve as agents for inhibiting cellular immunity mediated by T-cell antigen receptor.

Recent comparative genomic hybridization studies have identified Syk as another gene important in the pathogenesis of Mantle Cell Lymphoma (MCL) (Chen, R. et al. *Journal of Clinical Oncology,* 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B-cell lymphomas, with median survival of three years. It has been reported that Syk is overexpressed in MCL (Rinaldi, A, et al., *Br. J. Haematol,* 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et al., *Blood,* 2006; 108: 4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B-cell and Syk-dependent survival of non-Hodgkin's lymphoma cell lines in vitro (Chen, L., et al., *Blood,* 2006; 108:3428-3433), Syk inhibition is a promising rational treatment target for certain B-cell lymphomas.

The oncogenic potential of the spleen tyrosine kinase (Syk) has been described in a number of different settings. Clinically, Syk over-expression is reported in Mantle Cell Lymphoma (Rinaldi, A., et al., *Br. J. Haematol,* 2006; 132:303-316) and the TEL-Syk fusion protein (Translocated ETS Leukemia) generated by a chromosomal translocation (t(9; 12)(q22;p12)) leads to increased Syk activity and is associated with myelodysplastic syndrome (Kuno, Y., et al., *Blood,* 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et al., JEM, 2006; 203:2829-2840).

Interestingly, Syk signaling appears to be required for B-cell development and survival in humans and mouse. Inducible loss of the B-cell receptor (Lam, K., et al., *Cell,* 1997; 90:1073-1083) or Igα (Kraus, M., et al., *Cell,* 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et al., *Blood,* 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Additional recent studies also suggest that Syk-dependant survival signals may play a role in B-cell malignancies, including DLBCL, mantle cell lymphoma and follicular lymphoma (see, e.g., S. Linfengshen et al. *Blood*, February 2008; 111: 2230-2237; J. M. Irish et al. *Blood*, 2006; 108: 3135-3142; A. Renaldi et al. *Brit J. Haematology*, 2006; 132: 303-316; M. Guruoajan et al. *J. Immunol*, 2006; 176: 5715-5719; L. Laseux et al. *Blood*, 2006; 108: 4156-4162.

JAK kinases (Janus Kinases) are a family of cytoplasmic protein tyrosine kinases including JAK1, JAK2, JAK3 and TYK2. The JAKs play a crucial role in cytokine signaling. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal tranducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). JAK3 kinases have also been implicated in the mechanism involved in early and late stages of rheumatoid arthritis (Muller-Ladner et al., (2000), *J. Immunol.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10: 105-115).

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood* 89:4146-52; Kaneko et al., (1997), *Clin. Exp. Immun.* 109:185-193; and Nakamura et al., (1996), *J. Biol. Chem.* 271: 19483-8). They are also known to be important for lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection), bone marrow transplant applications (e.g., graft-versus-host disease), autoimmune diseases (e.g., diabetes), and inflammation (e.g., asthma, allergic reactions). Conditions which can benefit from JAK3 inhibition are discussed in greater detail below.

While progress has been made in this field, there remains a need in the art for compounds that inhibit Syk and/or JAK kinase, as well as for methods for treating conditions in a patient, such as restenosis, thrombosis, and/or inflammation that can benefit from such inhibition. Moreover, the availability of compounds that selectively inhibit kinases would also be desirable. The present invention satisfies these and other needs.

BRIEF SUMMARY

In brief, this invention is generally directed to novel compounds having activity as inhibitors of Syk activity (also referred to herein as "Syk inhibitors") and/or JAK kinase activity (also referred to herein as "JAK inhibitors"), as well as to methods for their preparation and use, and to pharmaceutical compositions containing the same. Such compounds have the following structure (I):

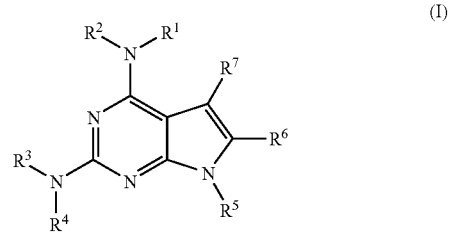

or a pharmaceutically acceptable salt thereof, wherein $R^1$, $R^2$, $R^3$, $R^4$, $R^5$, $R^6$ and $R^7$ are as defined below.

The present invention also provides a pharmaceutical composition comprising a therapeutically effective amount of a compound of formula I, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by Syk and/or JAK kinase activity, in both men and women, as well as a mammal in general (also referred to herein as a "Subject"). For example, such conditions include, but are not limited to, those associated with cardiovascular disease, inflammatory disease or autoimmune disease. More specifically, the compounds of the present invention have utility for treating conditions or disorders including, but not limited to: restenosis, thrombosis, inflammation, immune thrombocytopenic purpura, heparin induced thrombocytopenia, dilated cardiomyopathy, sickle cell disease, atherosclerosis, myocardial infarction, vascular inflammation, unstable angina, acute coronary syndromes, allergy, asthma, rheumatoid arthritis, B-cell mediated diseases such as non Hodgkin's lymphoma, chronic lymphocytic leukemia, acute myeloid leukemia, antiphospholipid syndrome, lupus, psoriasis, multiple sclerosis, sclerosis, end stage renal disease (platelet component), or hemolytic anemia. Thus, in one embodiment, methods are disclosed which include the administration of an effective amount of a compound of formula (I), typically in the form of a pharmaceutical composition, to a subject in need thereof.

The conditions associated with cardiovascular disease include acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

The present invention also provides a method for inhibiting the Syk and/or JAK kinase activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

DETAILED DESCRIPTION

As mentioned above, compounds are disclosed having the following general structure (I):

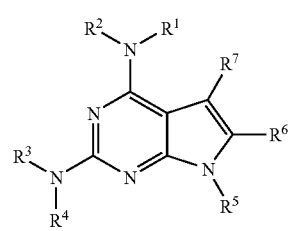

or a pharmaceutically acceptable salt thereof, wherein
$R^1$ is structure (a), (b), (c) or (d):

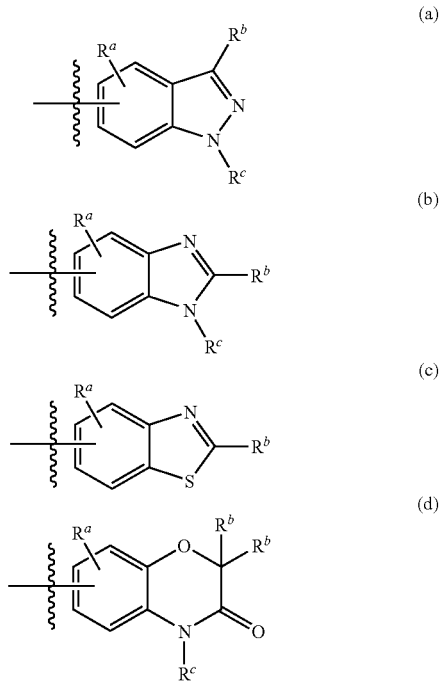

$R^a$ and $R^b$ are independently hydrogen, halogen, alkyl, aryl, heterocycle, —CN, —NO$_2$, —OR, —SR, —NRR, —C(=O)R —C(=O)OR, —NHC(=O)OR, or —SO$_2$NRR; and $R^c$ is hydrogen, alkyl, —S(O)R or —(SO$_2$)R;

R is, at each occurrence, independently hydrogen, alkyl, or aryl;

$R^2$ is hydrogen or alkyl;

$R^3$ is hydrogen, alkyl, optionally substituted aryl or optionally substituted heterocycle;

$R^4$ is hydrogen or alkyl;

$R^5$ is hydrogen or lower alkyl; and $R^6$ and $R^7$ are independently hydrogen, halogen, cyano, lower alkyl, aryl or heterocycle.

As used herein, the above terms have the following meaning:

"Alkyl" means a straight chain or branched, noncyclic or cyclic, unsaturated or saturated aliphatic hydrocarbon containing from 1 to 8 carbon atoms, while the term "lower alkyl" has the same meaning as alkyl but contains from 1 to 4 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Carbocycle" means an aryl group fused to a cyclic unsaturated or saturated aliphatic hydrocarbon containing from 1 to 8 carbon atoms.

"Halogen" means fluoro, chloro, bromo and iodo.

The terms "optionally substituted aryl" and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, hydroxy, cyano, alkyl, alkoxy, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

In some embodiments, substituents of an optionally substituted aryl group or an optionally substituted heterocycle group may join to form a fused ring. In these embodiments any two of the substituents, when attached to adjacent atoms of the aryl or heterocycle group, may be taken together with the atoms to which they are attached to form a fused heterocyclic ring or fused carbocyclic ring, wherein the fused heterocyclic ring and fused carbocyclic ring may be substituted with one or more substituents as defined above.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

The term "condition or disorder responsive to modulation of Syk and/or JAK" and related terms and phrases refer to a condition or disorder associated with inappropriate, e.g., less than or greater than normal, activity of Syk and/or JAK and at least partially responsive to or affected by modulation of Syk and/or JAK (e.g., Syk and/or JAK antagonist or agonist results in some improvement in patient well-being in at least some patients). Inappropriate functional activity of Syk and/or JAK might arise as the result of expression of Syk and/or JAK in cells which normally do not express the receptor, greater than normal production of Syk and/or JAK, or slower than normal metabolic inactivation or elimination of Syk and/or JAK or its active metabolites, increased expression of Syk and/or JAK or degree of intracellular activation (leading to, e.g., inflammatory and immune-related disorders and conditions) or decreased expression of Syk and/or JAK. A condition or disorder associated with Syk and/or JAK may include a "Syk and/or JAK-mediated condition or disorder".

The phrases "a condition or disorder mediated at least in part by Syk or JAK kinase activity", and related phrases and terms refer to a condition or disorder characterized by inappropriate, e.g., greater than normal, Syk and/or JAK activity. Inappropriate Syk and/or JAK functional activity might arise as the result of Syk and/or JAK expression in cells which normally do not express Syk and/or JAK or increased Syk and/or JAK expression or degree of intracellular activation (leading to, e.g., inflammatory and immune-related disorders and conditions). A condition or disorder mediated at least in part by Syk or JAK kinase activity may be completely or partially mediated by inappropriate Syk and/or JAK functional activity. However, a condition or disorder mediated at least in part by Syk or JAK kinase activity is one in which modulation of Syk and/or JAK results in some effect on the underlying condition or disorder (e.g., an Syk and/or JAK antagonist results in some improvement in patient well-being in at least some patients).

The term "inflammation" refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The term "JAK" refers to a Janus kinase (RefSeq Accession No. P-43408) or a variant thereof that is capable of mediating gene expression in vitro or in vivo. JAK variants include proteins substantially homologous to native JAK, i.e., proteins having one or more naturally or non-naturally occurring amino acid deletions, insertions or substitutions (e.g., JAK derivatives, homologs and fragments). The amino acid sequence of JAK variant preferably is at least about 80% identical to a native JAK, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of Syk and/or JAK, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Syk and/or JAK, either directly or indirectly, and/or the upregulation or downregulation of the expression of Syk and/or JAK, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Syk and/or JAK can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

The phrase "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The phrases "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The phrase "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "platelet" refers to a minute, nonnucleated, disklike cell found in the blood plasma of mammals that functions to promote blood clotting.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reaquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The term "selectively" or "specifically", when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

The term "Sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "Sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

A "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "Syk" refers to a spleen tyrosine kinase (RefSeq Accession No. P-043405) or a variant thereof that is capable of mediating a cellular response to T-cell receptors in vitro or in vivo. Syk variants include proteins substantially homologous to native Syk, i.e., proteins having one or more naturally or non-naturally occurring amino acid deletions, insertions or substitutions (e.g., Syk derivatives, homologs and fragments). The amino acid sequence of Syk variant preferably is at least about 80% identical to a native Syk, more preferably at least about 90% identical, and most preferably at least about 95% identical.

The term "Syk inhibitor" refers to any agent that inhibits the catalytic activity of spleen tyrosine kinase.

The term "thrombosis" refers to the blockage or clotting of a blood vessel caused by a clumping of cells, resulting in the obstruction of blood flow. The term "thrombus" refers to the clot that is formed within the blood vessel.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

In more specific embodiments, the compounds of this invention have the following structures (II), (III), (IV) or (V) when $R^1$ is structure (a), (b), (c) or (d), respectively:

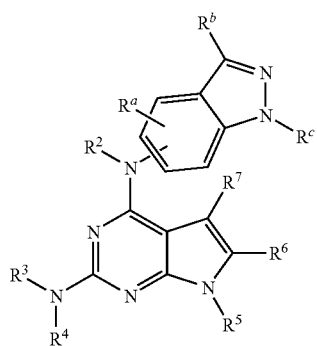

(II)

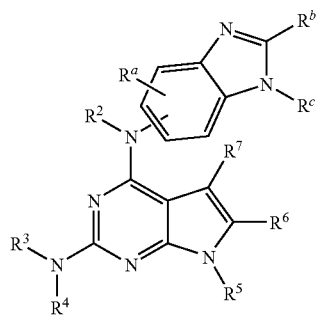

(III)

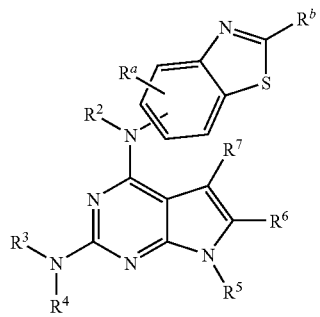

(IV)

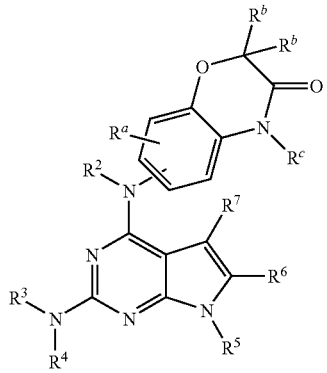

(V)

and pharmaceutically acceptable salts thereof, wherein $R^a$, $R^b$, $R^c$, $R^2$, $R^3$, $R^4$, $R^5$, $R^6$ and $R^7$ are as defined above.

In this regard, it should be understood that the point of attachment of structures (a), (b), (c) and (d) in structures (II), (III), (IV) and (V) above is at the 5- or 6-position of the bicyclic ring systems. For example, when $R^a$, $R^b$ and $R^c$ of structures (a), (b), (c), and (d) are hydrogen (as depicted by structures (a'), (b'), (c'), and (d') below), then the point of attachment is as shown in structures (a-1), (a-2), (b-1), (b-2), (c-1), (c-2), (d-1) and (d-2):

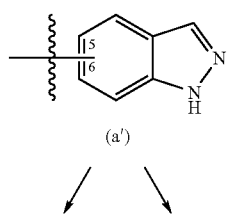

(a')

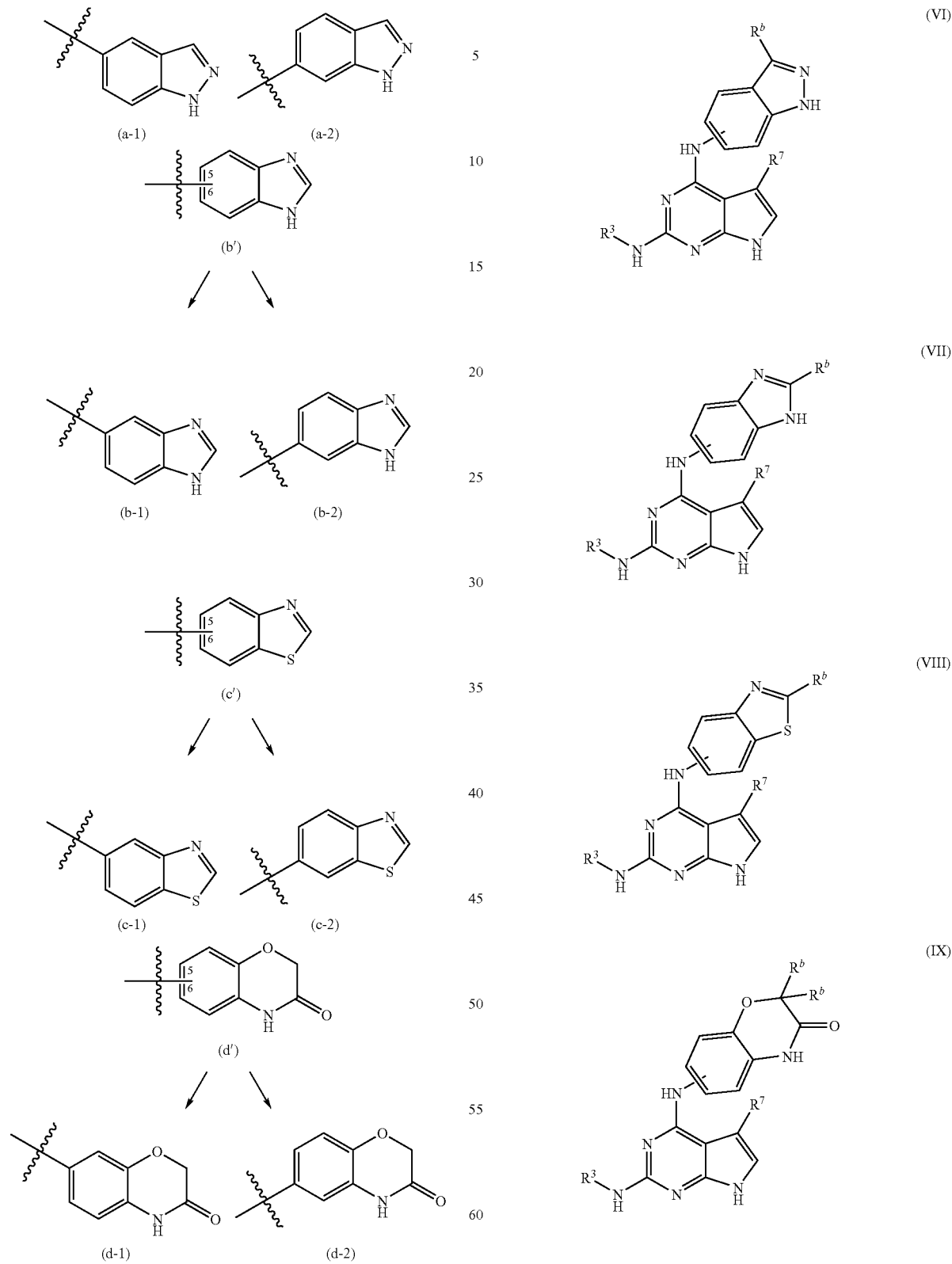
In one embodiment of structures (II), (III), (IV) and (V), $R^a$, $R^c$, $R^2$, $R^4$, $R^5$ and $R^6$ are hydrogen, and the compounds have the following structures (VI), (VII), (VIII) or (IX):
In further embodiments of structure (I), $R^3$ is an optionally substituted phenyl group bearing $R^{3a}$, $R^{3b}$ and $R^{3c}$, and compounds of this invention have structure (X):

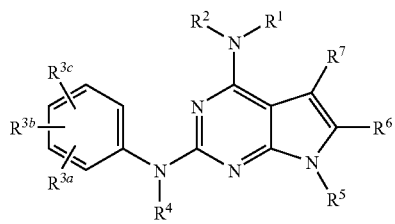
(X)

wherein $R^{3a}$, $R^{3b}$ and $R^{3c}$ are independently hydrogen, halogen, cyano, optionally substituted alkyl, optionally substituted aryl, optionally substituted heterocycle, —COOR$^8$, —COR$^8$, —CONR$^8_2$, —NR$^8$C(=O)R$^8$, —NR$^8$COOR$^8$, —OR$^8$, —SO$_n$R$^8$, —SO$_n$NR$^8_2$, —NR$^8$S(O)$_n$R$^8$, and —SO$_n$R$^9$ wherein R$^8$ is, at each occurrence, independently hydrogen or an optionally substituted alkyl group, R$^9$ is an optionally substituted heterocycle group and n is 0, 1 or 2, or any two of $R^{3a}$, $R^{3b}$ and $R^{3c}$ when attached to adjacent atoms of the phenyl group are taken together with the carbon atoms to which they are attached to form an optionally substituted, fused heterocylic ring, or an optionally substituted, fused carbocyclic ring.

In more specific embodiments of structure (X), at least one of $R^{3a}$, $R^{3b}$ and $R^{3c}$ has the following structure (where the wavy line indicates the point of attachment to the phenyl ring):

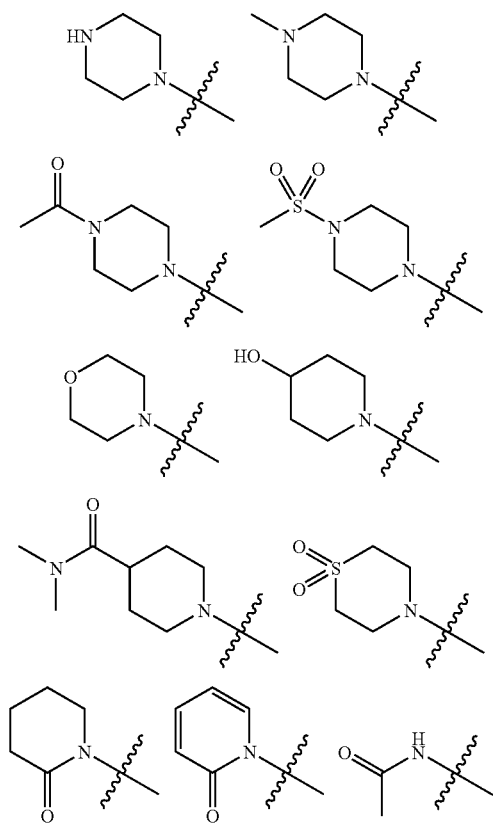

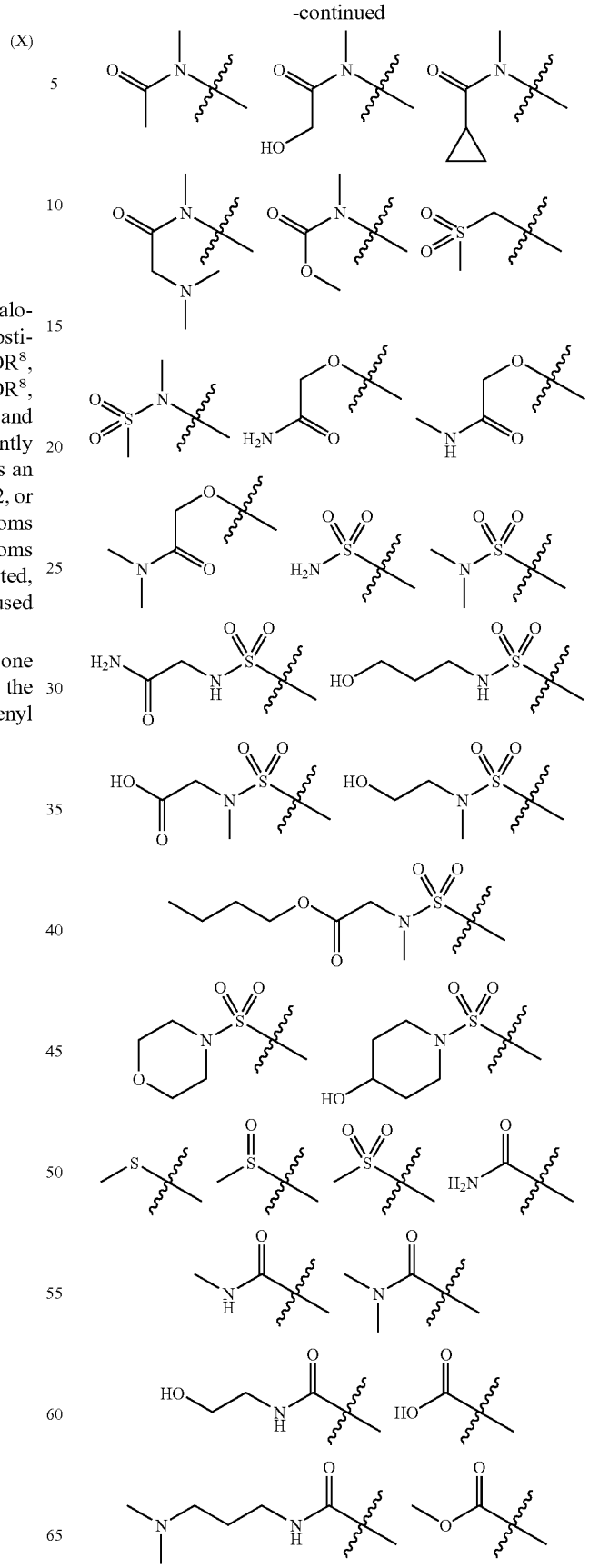

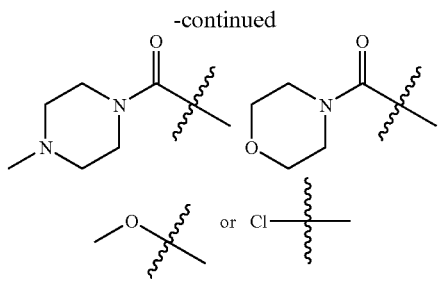

In yet more embodiments of structure (X), $R^{3b}$ and $R^{3c}$ when attached to adjacent atoms of the aryl group are taken together with the carbon atoms to which they are attached to form an optionally substituted, fused heterocylic ring, or an optionally substituted, fused carbocyclic ring as shown by structures (XI) and (XII) (where A represents an optionally substituted, fused heterocylic ring, or an optionally substituted, fused carbocyclic ring):

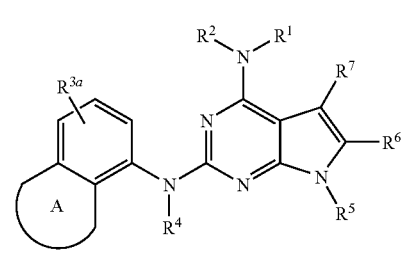
(XI)

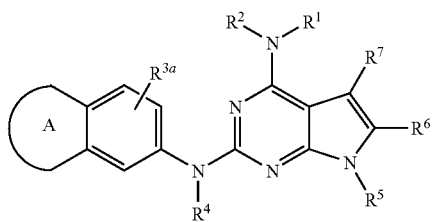
(XII)

Representative optionally substituted, fused heterocyclic rings of structures (XI) and (XII) include, but are not limited to, the following (where the wavy line indicates the point of attachment to the nitrogen atom bearing $R^4$):

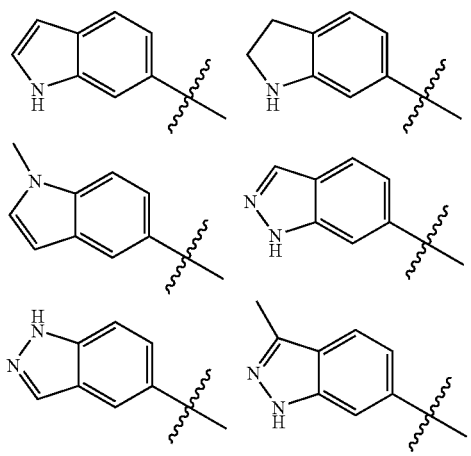

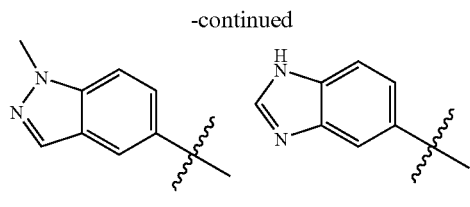
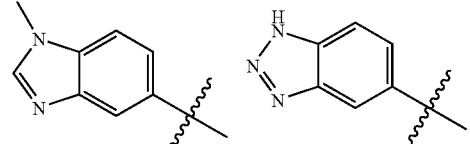
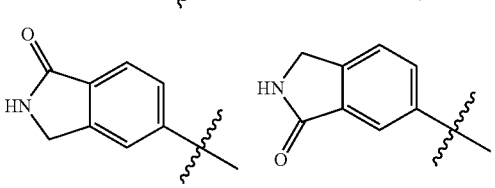
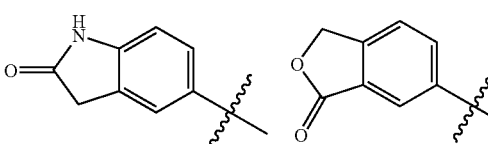
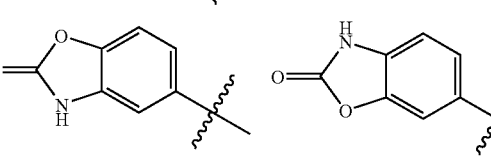
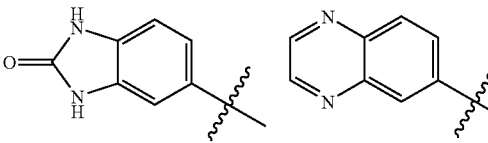
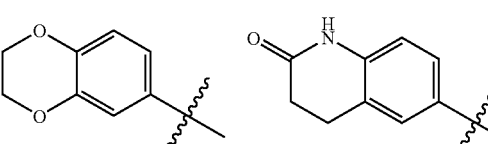
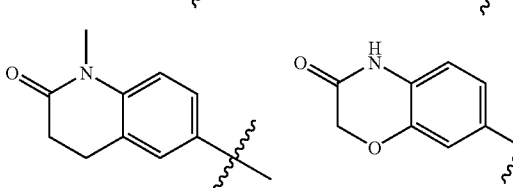
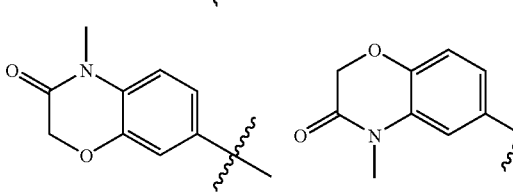
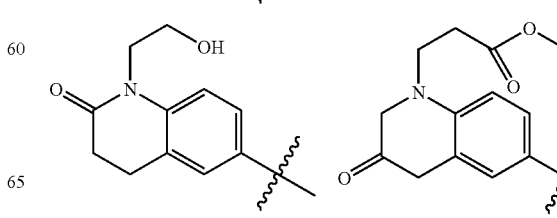

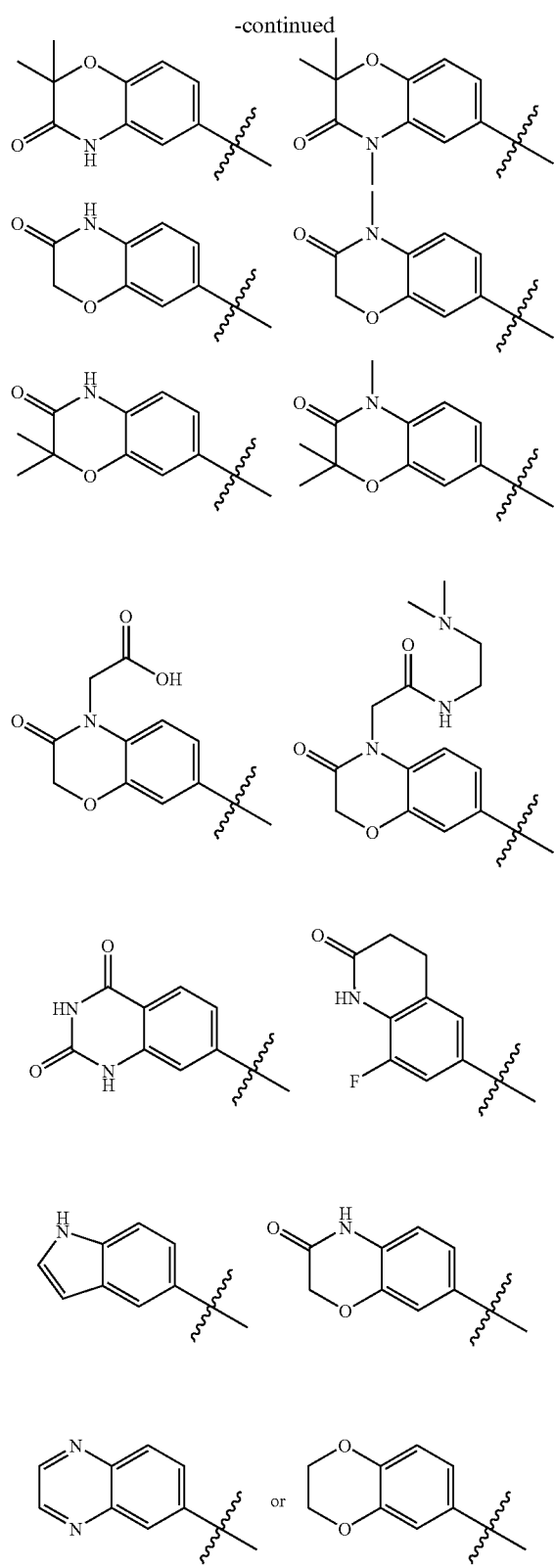

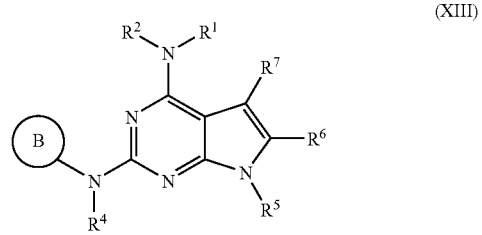

Representative optionally substituted heterocycle groups in the context of B above include, but are not limited to, optionally substituted pyridine groups and optionally substituted pyrimidine groups.

The compounds of the present invention may be prepared by known organic synthesis techniques, including the methods described in more detail in the Examples. In general, the compounds of structure (I) above may be made by the following Reaction Schemes 1-3, wherein all substituents are as defined above unless indicated otherwise.

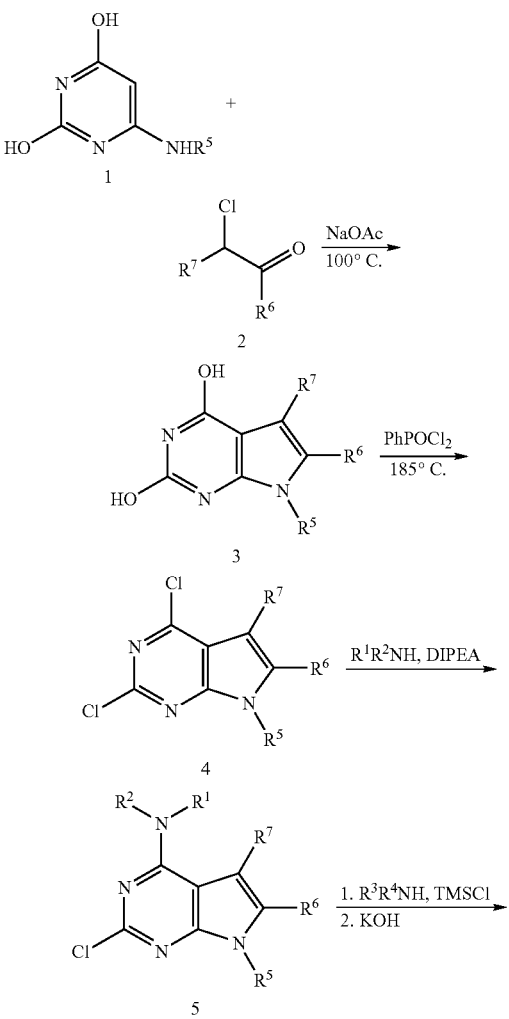

In other embodiments of structure (I), $R^3$ is an optionally substituted heterocycle group as represented by structure (XIII), wherein B represents an optionally substituted heterocycle as defined herein:

-continued

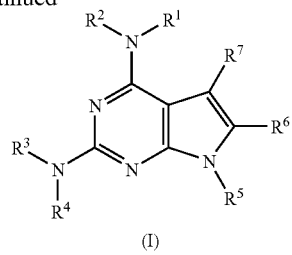

(I)

Compounds of structure (I) can be synthesized by methods known to those skilled in the art. For example, compounds of formula (1) and (2) can be purchased or synthesized using methods known to those skilled in the art. Heating compounds (1) and (2) in the presence of a base, such as sodium acetate (NaOAc), yields compounds of formula (3). Compounds of formula (3) can be converted to the chloro derivative (4) by treatment with an appropriate chlorinating reagent, such as phenylphosphonic dichloride (PhPOCl$_2$), at elevated temperatures. Reaction of (4) with an appropriate amine, for example R$^1$R$^2$NH (available commercially or synthesized using methods known to those skilled in the art), in the presence of a base, such as diisopropylethylamine (DIPEA), can then yield compounds of formula (5). Finally, compounds of formula (I) can be obtained by reaction of (5) with an appropriate amine, such as R$^3$R$^4$NH (available commercially or synthesized using methods known to those skilled in the art), and an activating reagent, such as trimethylsilyl chloride (TMSCl), followed by treatment with a base, such as potassium hydroxide (KOH).

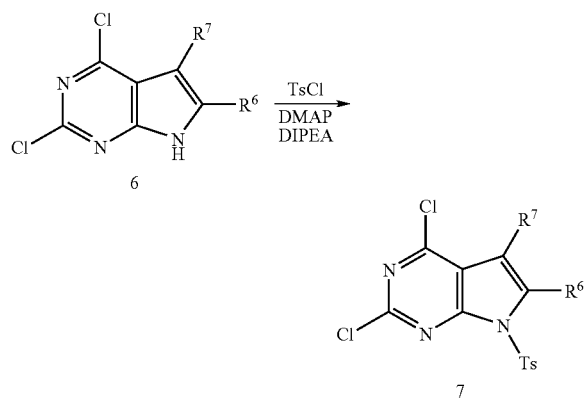

In certain embodiments of structure (I) when R$^5$ is hydrogen, it may be necessary to use a protecting group, for instance p-toluenesulfonyl. In this case, compounds of formula (6) can be reacted with the appropriately activated protecting group, such as p-toluensulfonyl chloride (TsCl), in the presence of a nucleophilic catalyst, such as dimethylaminopyridine (DMAP), and an appropriate base, such as diisopropylethylamine (DIPEA), to yield protected compounds of formula (7) (where the protecting group is shown to be p-toluenesulfonyl). Compounds of formula (7) can be utilized to make compounds of structure (I) by means of Reaction Scheme 1. The protecting group can be removed under the conditions of the final step in Reaction Scheme 1 to yield compounds of structure (I). Alternatively, the protecting group can be removed using methods known to those skilled in the art to yield compounds of structure (1).

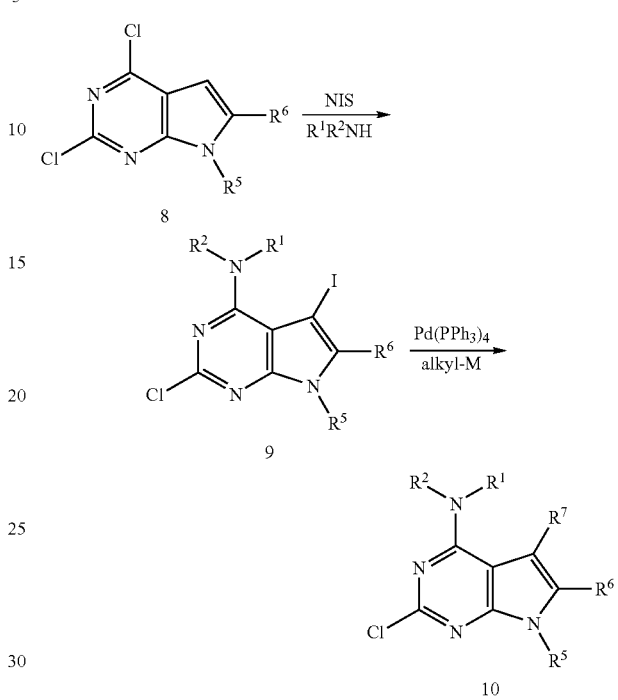

In certain embodiments of structure (I), R$^7$ can be installed via organometallic chemistries known to those skilled in the art. For instance, compounds of formula (8) can be treated with an appropriate halogenating reagent, such as N-iodosuccinimide, followed by reaction with an appropriate amine, such as R$^1$R$^2$NH (available commercially or synthesized using methods known to those skilled in the art), to obtain halo compounds, such as formula (9). Compounds of formula (9) can then be reacted with an appropriate organometallic catalyst, such as tetrakis(triphenylphosphine)palladium(0) (Pd(PPh$_3$)$_4$), and an appropriate alkyl metal (alkyl-M), for example tetravinyl tin, to obtain compounds of formula (10). Compounds of formula (10) can be converted to compounds of structure (I) using methods described in Reaction Scheme 1. One skilled in the art will recognize that in the case where R$^5$ is hydrogen, an appropriate protecting group strategy, such as that described in Reaction Scheme 2, may be necessary. Additionally, one skilled in the art will recognize that further manipulations of the alkyl group derived from the alkyl metal reagent, such as catalytic hydrogenation, may be required after formation of the carbon-carbon bond to obtain the desired R$^7$ structure.

The compounds of the present invention may generally be utilized as the free base. Alternatively, the compounds of this invention may be used in the form of acid addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

For the purposes of administration, the compounds of the present invention may be formulated as pharmaceutical compositions. Pharmaceutical compositions of the present invention comprise a compound of formula (I) and a pharmaceutically acceptable carrier and/or diluent. The compound of formula (I) is present in the composition in an amount which is effective to treat a particular disorder—that is, in an amount sufficient to achieve Syk and/or JAK inhibitory activity, and preferably with acceptable toxicity to the patient. Syk and JAK inhibitory activity of compounds of formula (I) can be determined, for example, as described in Example 28, and as discussed below. Typically, the pharmaceutical compositions of the present invention may include a compound of formula (I) in an amount from 0.001 mg to 100 mg per dosage depending upon the route of administration, and more typically from 0.01 mg to 10 mg. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of formula (I), diluents, dispersing and surface active agents, binders, and lubricants. One skilled in this art may further formulate the compound of formula (I) in an appropriate manner, and in accordance with accepted practices, such as those disclosed in Remington's Pharmaceutical Sciences, Gennaro, Ed., Mack Publishing Co., Easton, Pa. 1990.

The present invention also provides for methods of using compounds of formula (I) to treat a disease or condition. Such methods include administering of a compound of the present invention to a warm-blooded animal in an amount sufficient to treat the condition or disease. Such methods include systemic administration of a compound of formula (I) of this invention, preferably in the form of a pharmaceutical composition as discussed above. As used herein, systemic administration includes oral and parenteral methods of administration. For oral administration, suitable pharmaceutical compositions of a compound of formula (I) include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain, in addition to the compound of formula (I), buffers, antioxidants, bacteriostats, and other additives commonly employed in such solutions.

The activity of a specified compound as an inhibitor of a Syk and/or JAK kinase may be assessed in vitro or in vivo. In some embodiments, the activity of a specified compound can be tested in a cellular assay. Selectivity could also be ascertained in biochemical assays with isolated kinases.

Similar types of assays can be used to assess JAK kinase inhibitory activity and to determine the degree of selectivity of the particular compound as compared to Syk kinase. One means of assaying for such inhibition is detection of the effect of the compounds of the present invention on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimindinediamine compounds described herein) on the JAK1 and JAK3 kinases, human Ramos B-cells are stimulated with human IL-4. 10' post-stimulation, cells are subjected to intracellular flow cytometry to measure the extent of STAT-6 phosphorylation. 20 to 24 hours post-stimulation, cells are stained for upregulation of CD23 and analyzed using flow cytometry. A reduction of the amount of phosphohorylated STAT-6 and/or cell surface CD23 compared to control conditions indicates that the test compound actively inhibits the JAK kinase pathway.

Additionally, IL-6 stimulation of Ramos B-cells induces JAKs 1, 2, and Tyk2, leading to Stat-3 and Erk phosphorylation. 10' post-stimulation, cells are subjected to intracellular flow cytometry to measure the ability of compound to inhibit these phosphorylation events. To specifically measure the activity of JAK2, the CellSensor irfl-bla HEL cell line expressing the beta-lactamase reporter gene controlled by Stat5 will be used (Invitrogen, Carlsbad, Calif.). These cells express a constituitively active JAK2 mutant (JAK2V617F), found naturally in myeloproliferative neoplasms (Constantinescu, S., et al., *Trends Biochem Sci.*, 2008; 33:122-31). A reduction in the amount of beta-lactamase reporter gene expression is used a measure of the JAK2 inhibitory activity of compounds.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFN gamma induces ICAM-1 up-regulation through activation of the JAK1/JAK2 pathway. The up-regulation of ICAM-1 can be quantified by flow cytometry across a compound dose curve and EC50 values are calculated.

Active compounds as described herein generally inhibit the JAK kinase pathway with an IC50 in the range of about 1 mM or less, as measured in the assays described herein. Of course, skilled artisans will appreciate that compounds which exhibit lower IC50s, (on the order, for example, of 100 µM, 75 M, 50 µM, 40 M, 30 µM, 20 µM, 15 µM, 10 µM, 5 µM, 1 µM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The active compounds also typically inhibit IL-4 stimulated expression of CD23 in B-cells with an IC50 in the range of about 20 µM or less, typically in the range of about 10 µM, 1 µM, 500 nM, 100 nM, 10 nM, 1 nM, or even lower. A suitable assay that can be used is the assay described in the Examples, "Assay for Ramos B-cell Line Stimulated with IL-4." In certain embodiments, the active compounds of the present invention have an IC50 of less than or equal to 5 µM, greater than 5 µM but less than 20 µM, greater than 20 µM, or greater than 20 µM but less than 50 µM in the assay described in the Examples.

The active compounds also typically inhibit expression of ICAM1 (CD54) induced by IFN.gamma. exposure in U937 or A549 cells with an IC50 in the range of about 20 µM or less, typically in the range of about 10 µM, 1 µM, 500 nM, 100 nM, 10 nM, 1 nM, or even lower. The IC50 against expression of ICAM (CD54) in IFNγ stimulated cells can be determined in a functional cellular assay with an isolated A549 or U937 cell line. Suitable assays that can be used are the assays described in the Examples, "A549 Epithelial Line Stimulated with IFNγ" and "U937 IFN.gamma. ICAM1 FACS Assay," respectively. In certain embodiments, the active compounds of the present invention have an IC50 of less than or equal to 20 µM, greater than 20 µM, or greater than 20 µM but less than 50 µM in the assays described in the Examples.

The invention provides methods of inhibiting or decreasing Syk and/or JAK activity as well as treating or ameliorating a Syk and/or JAK associated state, symptom, condition, disorder or disease in a patient in need thereof (e.g., human or non-human). In one embodiment, the Syk and/or JAK associated state, symptom, condition, disorder or disease is mediated, at least in part by Syk and/or JAK kinase activity. In more specific embodiments, the present invention provides a method for treating a condition or disorder mediated at least in part by Syk and/or JAK kinase activity is cardiovascular disease, inflammatory disease or autoimmune disease.

In one embodiment, the invention provides methods for preventing or treating a condition in a mammal characterized by undesired thrombosis comprising the step of administering to the mammal a therapeutically effective amount of a compound of the present invention. Such conditions include, but are not limited, to restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purura, heparin induced thrombocytopenia, dilated cardiomypathy, sickle cell disease, atherosclerosis, myocardial infarction, vacular inflammation, unstable angina or acute coronary syndromes.

In another embodiment, the present invention also provides a method for treating allergy, asthma, rheumatoid arthritis, B-cell mediated disease such as non-Hodgkin's lymphoma, anti-phospholipids syndrome, lupus, psoriasis, multiple sclerosis, chronic lymphocytic leukemia, or end stage renal disease (platelet component).

In another embodiment, the present invention provides a method for treating hemolytic anemia or immune thrombocytopenic purpura.

The compounds described herein are also potent and/or selective inhibitors of JAK kinases. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren's syndrome, Type II inflammatory disease such as vascular inflammation (including vasculitis, ateritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas.

In another embodiment, this invention provides a method of inhibiting an activity of a JAK kinase, comprising contacting the JAK kinase with an amount of a compound effective to inhibit an activity of the JAK kinase, wherein the compound is selected from the compounds of this invention. In certain embodiments of the methods described herein, the method is carried out in vivo.

In another embodiment, this invention provides a method of inhibiting an activity of a JAK kinase, comprising contacting in vitro a JAK3 kinase with an amount of a compound effective to inhibit an activity of the JAK kinase, wherein the compound is selected from the compounds of this invention.

In a specific embodiment, the compounds can be used to treat and/or prevent rejection in organ and/or tissue transplant recipients (i.e., treat and/or prevent allorgraft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compounds can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoriasis, or Sjogren's syndrome. Such autoimmune diseases include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be beta-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with the compounds generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the compounds. In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycopheno late, mycopheno late mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a Syk kinase. Syk kinase is a tyrosine kinase known to play a critical role in Fcy receptor signaling, as well as in other signaling cascades, such as those involving B-cell receptor signaling (Turner et al., (2000), *Immunology Today* 21:148-154) and integrins beta (1), beta (2), and beta (3) in neutrophils (Mocsai et al., (2002), *Immunity* 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (Publication no. 2004/0029902); WO 03/063794; Ser. No. 10/631,029 filed Jul. 29, 2003 (Publication no. 2007/0060603); WO 2004/014382; Ser. No. 10/903,263 filed Jul. 30, 2004 (Publication no. 2005/0234049); PCT/US2004/24716 filed Jul. 30, 2004 (WO 2005/016893); Ser. No. 10/903,870 filed Jul. 30, 2004 (Publication no. 2005/0209224); PCT/US2004/

24920 filed Jul. 30, 2004 (WO 2005/012294); Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The described herein and Syk/JAK inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a Syk inhibitory compound or one of the other current treatments for the particular disease. The compounds could also be used in combination with Syk inhibitory compounds in patients that are Syk-compound resistant or non-responsive. Suitable Syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits Syk kinase with an IC50 in the range of at least 10 µM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK3 kinase plays a role, comprising contacting a cell expressing a receptor involved in such a signaling cascade with a compound wherein the compound is selected from the compounds of this invention, as described herein.

In another embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a Syk and/or JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit the Syk and/or JAK/Stat pathway. The activity of a specified compound as an inhibitor of a Syk and/or JAK kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA*, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and NK-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the Syk and/or JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant Syk and/or JAK activity can be treated with the Syk and/or JAK inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" in this context includes an alleviation of symptoms associated with a disorder or disease, or halt of further progression or worsening of those symptoms, or prevention or prophylaxis of the disease or disorder. The term "mammal" includes organisms which express Syk and/or JAK. Examples of mammals include mice, rats, cows, sheep, pigs, goats, horses, bears, monkeys, dogs, cats and, preferably, humans. Transgenic organisms which express Syk and/or JAK are also included in this definition.

The inventive methods comprise administering an effective amount of a compound or composition described herein to a mammal or non-human animal. As used herein, "effective amount" of a compound or composition of the invention includes those amounts that antagonize or inhibit Syk and/or JAK. An amount which antagonizes or inhibits Syk and/or JAK is detectable, for example, by any assay capable of determining Syk and/or JAK activity, including the one described below as an illustrative testing method. Effective amounts may also include those amounts which alleviate symptoms of a Syk and/or JAK associated disorder treatable by inhibiting Syk and/or JAK. Accordingly, "antagonists of Syk" or "antagonists of JAK" include compounds which interact with the Syk or JAK, respectively, and modulate, e.g., inhibit or decrease, the ability of a second compound, e.g., another Syk or JAK ligand, to interact with the Syk or JAK, respectively. The Syk or JAK binding compounds are preferably antagonists of Syk or JAK, respectively. The language "Syk binding compound" and "JAK-binding compound" (e.g., exhibits binding affinity to the receptor) includes those compounds which interact with Syk or JAK resulting in modulation of the activity of Syk or JAK, respectively. Syk and/or JAK binding compounds may be identified using an in vitro (e.g., cell and non-cell based) or in vivo method. A description of in vitro methods is provided below.

The amount of compound present in the methods and compositions described herein should be sufficient to cause a detectable decrease in the severity of the disorder, as measured by any of the assays described in the examples. The amount of Syk and/or JAK modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

The invention comprises a compound having structure (I) above, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

In some embodiments, the compounds of the present invention may be "dual" Syk/JAK inhibitors in that they inhibit both Syk and JAK kinase to some degree. In other embodiments, the compounds of the present invention may selectively inhibit Syk kinase, but not appreciably inhibit one or more JAK kinases. In other embodiments, the compounds of the present invention may selectively inhibit JAK kinase, but not appreciably inhibit one or more Syk kinases.

The following examples are provided for purposes of illustration, not limitation.

EXAMPLES

Referring to the examples that follow, compounds of the present invention were synthesized using the methods described herein, or other methods, which are well known in the art. The compounds and/or intermediates were characterized by high performance liquid chromatography (HPLC) using a Waters Alliance chromatography system with a 2695 Separation Module (Milford, Mass.). The analytical columns were C-18 SpeedROD RP-18E Columns from Merck KGaA (Darmstadt, Germany). Alternately, characterization was performed using a Waters Unity (HPLC) system with Waters Acquity HPLC BEH C-18 2.1 mm×15 mm columns. A gradient elution was used, typically starting with 5% acetonitrile/95% water and progressing to 95% acetonitrile over a period of 5 minutes for the Alliance system and 1 minute for the Acquity system. All solvents contained 0.1% trifluoroacetic acid (TFA). Compounds were detected by ultraviolet light (UV) absorption at either 220 or 254 nm. HPLC solvents were from EMD Chemicals, Inc. (Gibbstown, N.J.). In some instances, purity was assessed by thin layer chromatography (TLC) using glass backed silica gel plates, such as, for example, EMD Silica Gel 60 2.5 cm×7.5 cm plates. TLC results were readily detected visually under ultraviolet light, or by employing well known iodine vapor and other various staining techniques.

Mass spectrometric analysis was performed on one of two Agilent 1100 series LCMS instruments with acetonitrile/water as the mobile phase. One system uses TFA as the modifier and measures in positive ion mode, and the other system uses either formic acid or ammonium acetate and measures in both positive and negative ion modes. Nuclear magnetic resonance (NMR) analysis was performed on some of the compounds with a Varian 400 MHz NMR (Palo Alto, Calif.). The spectral reference was either tetramethylsilane (TMS) or the known chemical shift of the solvent.

Preparative separations were carried out using either an Sq16x or an Sg100c chromatography system and prepackaged silica gel columns purchased from Teledyne Isco, (Lincoln, Nebr.). Alternately, compounds and intermediates were purified by flash column chromatography using silica gel (230-400 mesh) packing material, or by HPLC using a C-18 reversed phase column. Typical solvents employed for the Isco systems and flash column chromatography were dichloromethane, methanol, ethyl acetate, hexane, acetone, aqueous hydroxyamine and triethylamine. Typical solvents employed for the reverse phase HPLC were varying concentrations of acetonitrile and water with 0.1% trifluoroacetic acid.

Example 1

1-(4-(4-(4-(1H-indazol-6-ylamino)-7H-pyrrolo[2,3-d]pyrimidin-2-ylamino)phenyl)piperazin-1-yl)ethanone and N4-(1H-indazol-6-yl)-N2-(4-(piperazin-1-yl)phenyl)-7H-pyrrolo[2,3-d]pyrimidine-2,4-diamine

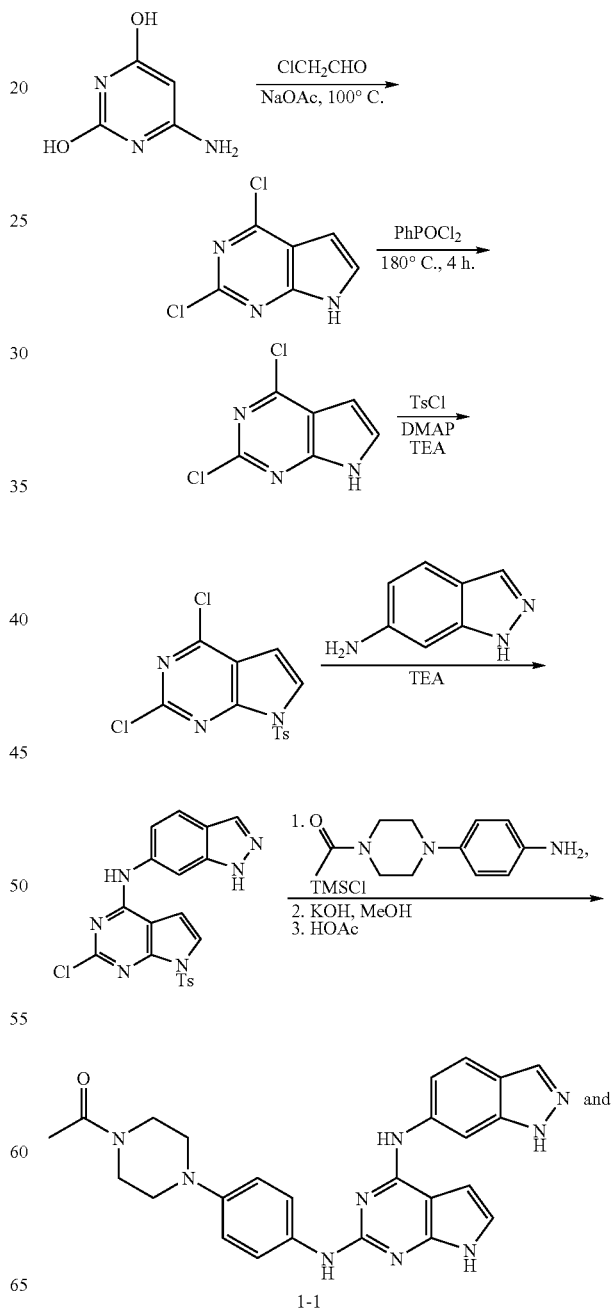

1-1

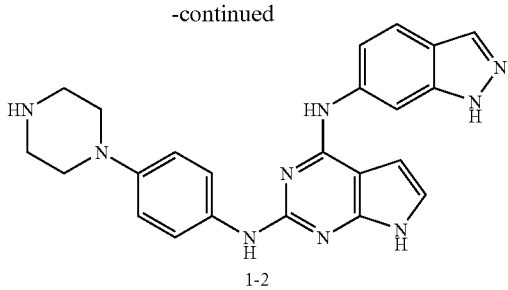

1-2

To a suspension of 6-aminouracil (15 g, 0.118 mol) in H₂O (600 mL) was added sodium acetate (NaOAc) (15 g, 0.183 mol) and chloroethanal (ClCH₂CHO) (50% in H₂O, 30 mL). The mixture was heated at reflux for 4 h and then cooled to room temperature. The resulting dark brown precipitates were collected by filtration to afford crude 7H-Pyrrolo[2,3-d]pyrimidine-2,4-diol (14.4 g, 81% yield).

A suspension of 7H-Pyrrolo[2,3-d]pyrimidine-2,4-diol (2.25 g, 0.015 mol) in phenylphosphinic dichloride (Ph-POCl₂) (15 mL) was heated at 180° C. for 4 h. The resulting dark syrup was poured slowly to ice water, the black precipitates were filtered off, and the filtrate was extracted with ether. The ether layers were combined, washed sequentially with sat. NaHCO₃, brine, dried over Na₂SO₄ and concentrated to give 2,4-Dichloro-7H-Pyrrolo[2,3-d]pyrimidine (0.8 g, 28% yield).

To a suspension of 2,4-dichloro-7H-pyrrolo[2,3-d]pyrimidine (1.59 g, 8.46 mmol), p-toluenesulfonyl chloride (1.93 g, 10.1 mmol) and triethylamine (TEA) (2.35 mL, 16.9 mmol) in CH₂Cl₂ (15 mL), dimethylaminopyridine (DMAP) (27 mg, 0.22 mmol) was added. As soon as the DMAP was added, the suspension became clear. The solution was then stirred at room temperature for 1 h. It was washed with 1N HCl, then with 5% NaHCO₃, dried over Na₂SO₄ and concentrated in vacuo to give 2,4-dichloro-7-tosyl-7H-pyrrolo[2,3-d]pyrimidine as a solid (2.55 g).

A mixture of 2,4-dichloro-7-tosyl-7H-pyrrolo[2,3-d]pyrimidine (400 mg, 1.17 mmol), 6-aminoindazole (171 mg, 1.29 mmol) and triethylamine (0.400 mL, 2.88 mmol) in n-butyl alcohol (10 mL) was heated at 80° C. overnight. After cooling down, H₂O and CH₂Cl₂ were added. The organic phase was separated, washed with 1N HCl, followed by 5% NaHCO₃, before it was dried over Na₂SO₄ and concentrated in vacuo to give 2-chloro-N-(1H-indazol-6-yl)-7-tosyl-7H-pyrrolo[2,3-d]pyrimidin-4-amine as a solid (490 mg).

A mixture of 2-chloro-N-(1H-indazol-6-yl)-7-tosyl-7H-pyrrolo[2,3-d]pyrimidin-4-amine (340 mg, 0.78 mmol), 1-(4-(4-aminophenyl)piperazin-1-yl)ethanone (204 mg, 0.93 mmol) and trimethylsilyl chloride (TMSCl) (0.200 mL, 1.58 mmol) in n-butyl alcohol (8 mL) was heated at 116° C. overnight. More 1-(4-(4-aminophenyl)piperazin-1-yl)ethanone (204 mg, 0.93 mmol) was added. The mixture was then stirred at 116° C. for another 48 h. It was then purified by HPLC to give 1-(4-(4-(4-(1H-indazol-6-ylamino)-7-tosyl-7H-pyrrolo[2,3-d]pyrimidin-2-ylamino)phenyl)piperazin-1-yl)ethanone as a solid (126 mg).

To a solution of 1-(4-(4-(4-(1H-indazol-6-ylamino)-7-tosyl-7H-pyrrolo[2,3-d]pyrimidin-2-ylamino)phenyl)piperazin-1-yl)ethanone (60 mg, 0.097 mmol) in methanol (MeOH) (4 mL), aq. 1N potassium hydroxide (KOH) (1.0 mL, 1.0 mmol) was added. The mixture was heated at 60° C. for 5 h before it was concentrated in vacuo. The residue was acidified with acetic acid (HOAc) (1 mL) before being purified by HPLC to give 1-(4-(4-(4-(1H-indazol-6-ylamino)-7H-pyrrolo[2,3-d]pyrimidin-2-ylamino)phenyl)piperazin-1-yl)ethanone (21 mg), MS 468.2 (M+H) (Compound 1-1); and N4-(1H-indazol-6-yl)-N2-(4-(piperazin-1-yl)phenyl)-7H-pyrrolo[2,3-d]pyrimidine-2,4-diamine (3 mg), MS 426.3 (M+H) (Compound 1-2).

Example 2

1-(4-(4-(4-(3-methyl-1H-indazol-6-ylamino)-7H-pyrrolo[2,3-d]pyrimidin-2-ylamino)phenyl)piperazin-1-yl)ethanone and N4-(3-methyl-1H-indazol-6-yl)-N2-(4-(piperazin-1-yl)phenyl)-7H-pyrrolo[2,3-d]pyrimidine-2,4-diamine

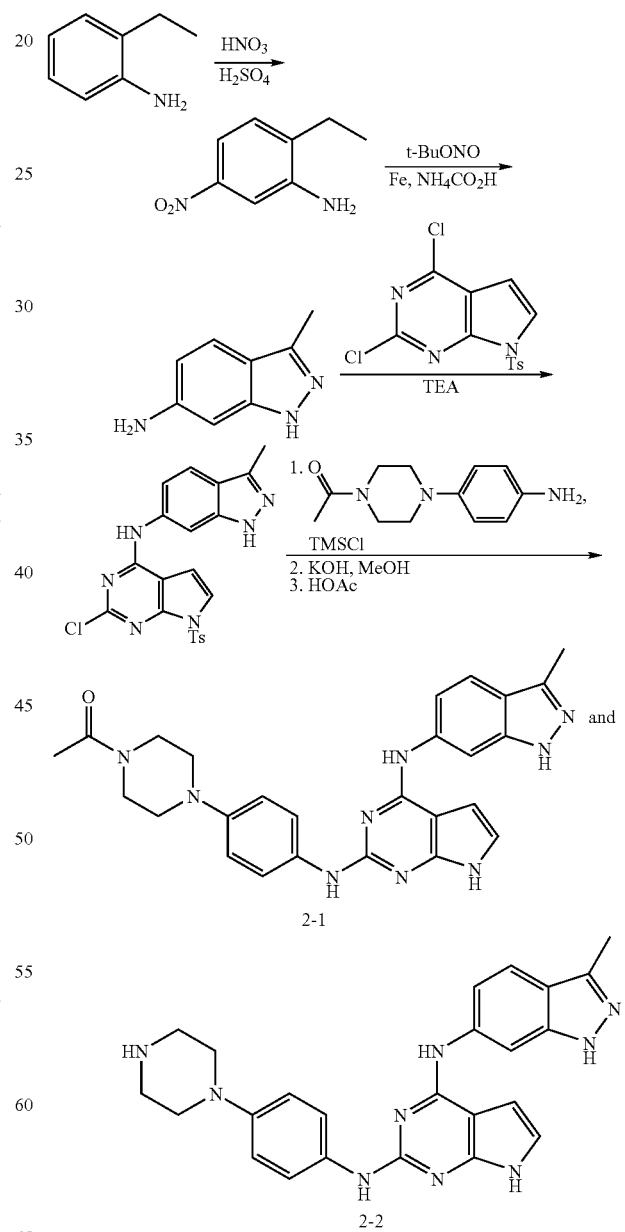

2-1

2-2

To a solution of 2-ethylaniline (12.1 g, 0.1 mol) in conc. H₂SO₄ (50 mL) at 0° C. was added fuming HNO₃ (9.3 g) drop wise. After stirring at ambient temperature for 30 min, the mixture was poured into ice-water, and 2 N NaOH was added to neutralize the excess acid. The resulting reddish-brown solid was collected by filtration and washed with petroleum ether to give 2-ethyl-5-nitroaniline as crude product (9 g).

To a mixture of 2-ethyl-5-nitroaniline (2 g, 12 mmol) in acetic acid (AcOH) (60 mL) at ambient temperature was added a solution of tert-butyl nitrite (t-BuONO) (1.8 mL, 12 mmol) in AcOH (8 mL). After stirring at ambient temperature for 1 h, AcOH was removed in vacuo. The resulting residue was dissolved in ethyl acetate (EtOAc), washed with Sat. NaHCO₃, dried over Na₂SO₄, and concentrated to afford 3-methyl-6-nitroindazole (1.2 g).

To a solution of 3-methyl-6-nitroindazole (0.4 g, 2.24 mmol) in ethanol (EtOH) (10 mL) and H₂O (5 mL) was added Iron (0.63 g, 11.22 mmol) and ammonium formate (1.4 g, 22.4 mmol). After heating at 90° C. for 2 h, the mixture was diluted with EtOAc, excess iron was removed by filtration, and the filtrate was washed sequentially with water, sat. NaHCO₃, and brine, before it was dried and concentrated to give 6-amino-3-methylindazole (0.27 g).

A mixture of 2,4-dichloro-7-tosyl-7H-pyrrolo[2,3-d]pyrimidine (200 mg, 0.585 mmol), 6-amino-3-methylindazole (94 mg, 0.64 mmol) and triethylamine (TEA) (0.200 mL, 1.44 mmol) in n-butyl alcohol (n-BuOH) (5 mL) was heated at 110° C. overnight. After cooling down, H₂O and EtOAc were added. The organic phase was separated, washed with 1N HCl, followed by 5% NaHCO₃, before being dried over Na₂SO₄ and concentrated in vacuo to give 2-chloro-N-(3-methyl-1H-indazol-6-yl)-7-tosyl-7H-pyrrolo[2,3-d]pyrimidin-4-amine (260 mg).

A mixture of 2-chloro-N-(3-methyl-1H-indazol-6-yl)-7-tosyl-7H-pyrrolo[2,3-d]pyrimidin-4-amine (260 mg, 0.574 mmol), 1-(4-(4-aminophenyl)piperazin-1-yl)ethanone (251 mg, 1.15 mmol) and trimethylsilyl chloride (TMSCl) (0.150 mL, 1.19 mmol) in n-BuOH (5 mL) was heated at 116° C. for 48 h. It was then purified by HPLC to give 1-(4-(4-(4-(3-methyl-1H-indazol-6-ylamino)-7-tosyl-7H-pyrrolo[2,3-d]pyrimidin-2-ylamino)phenyl)piperazin-1-yl)ethanone (30 mg).

To a solution of 1-(4-(4-(4-(3-methyl-1H-indazol-6-ylamino)-7-tosyl-7H-pyrrolo[2,3-d]pyrimidin-2-ylamino)phenyl)piperazin-1-yl)ethanone (30 mg, 0.047 mmol) in methanol (MeOH) (3 mL), aq. 1N KOH (1.0 mL, 1.0 mmol) was added. The mixture was heated at 60° C. for 5 h. and then concentrated in vacuo. The residue was acidified with HOAc (1 mL) before being purified by HPLC to give 1-(4-(4-(4-(3-methyl-1H-indazol-6-ylamino)-7H-pyrrolo[2,3-d]pyrimidin-2-ylamino)phenyl)piperazin-1-yl)ethanone (10 mg), MS 482.2 (M+H) (Compound 2-1); and N4-(3-methyl-1H-indazol-6-yl)-N2-(4-(piperazin-1-yl)phenyl)-7H-pyrrolo[2,3-d]pyrimidine-2,4-diamine (3 mg), MS 440.1 (M+H) (Compound 2-2).

Example 3

6,6'-(7H-pyrrolo[2,3-d]pyrimidine-2,4-diyl)bis(azanediyl)bis(2,2-dimethyl-2H-benzo[b][1,4]oxazin-3(4H)-one

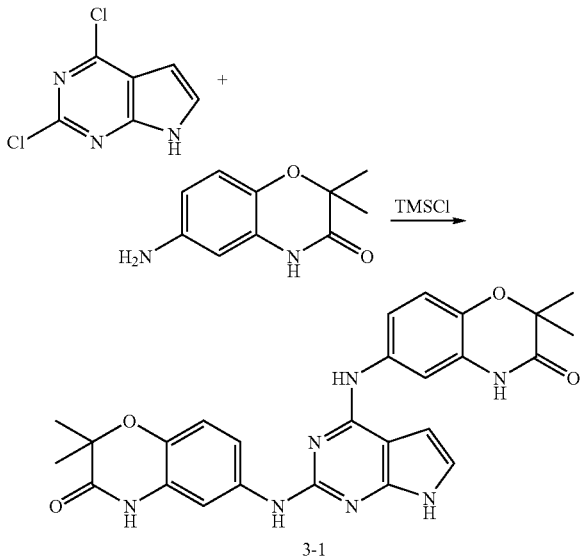

To a mixture of 2,4-dichloro-7H-pyrrolo[2,3-d]pyrimidine (0.038 g, 0.2 mmol) in n-butyl alcohol (n-BuOH) (1 mL) was added 6-amino-2,2-dimethyl-2H-benzo[b][1,4]oxazin-3 (4H)-one (0.115 g, 0.6 mmol) and trimethylsilyl chloride (TMSCl) (4 drops). After heating for 3 h, the mixture was purified by preparative HPLC to give 6,6'-(7H-pyrrolo[2,3-d]pyrimidine-2,4-diyl)bis(azanediyl)bis(2,2-dimethyl-2H-benzo[b][1,4]oxazin-3(4H)-one (0.02 g, MS 500.2 (MH+)) (Compound 3-1).

Example 4

N2,N4-di(1H-indazol-6-yl)-7H-pyrrolo[2,3-d]pyrimidine-2,4-diamine

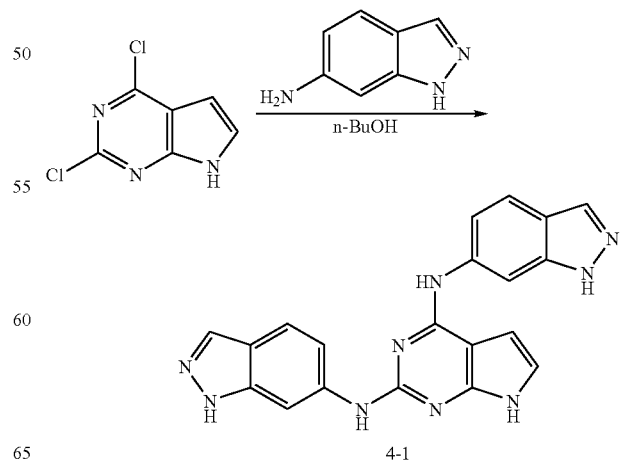

A mixture of 2,4-dichloro-7H-pyrrolo[2,3-d]pyrimidine (90 mg, 0.48 mmol) and 6-aminoindazole (127 mg, 0.95 mmol) in n-butyl alcohol (n-BuOH) (4 mL) was stirred at 116° C. overnight. The mixture was purified by reverse phase HPLC using a gradient of 7-50% CH₃CN in water over 10 min. The title compound was recovered to give a powder (15 mg). MS 382.4 (M+H) (Compound 4-1).

Example 5

$N^4$-(1H-benzo[d]imidazol-6-ylamino)-$N^2$-(1H-indazoyl-6-yl)-7H-pyrrolo[2,3-d]pyrimidin-2,4-diamine

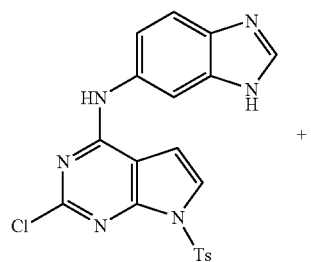

+

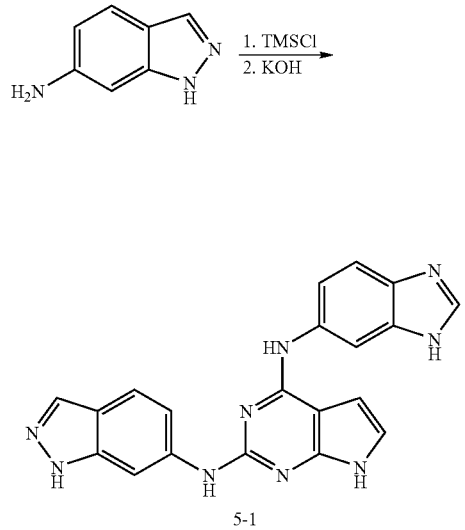

5-1

To a mixture of N-(1H-benzo[d]imidazol-6-yl)-2-chloro-7-tosyl-7H-pyrrolo[2,3-d]pyrimidin-4-amine (0.095 g, 0.22 mmol) in n-butyl alcohol (n-BuOH) (0.8 mL) was added 6-aminoindazole (0.057 g, 0.44 mmol) and trimethylsilyl chloride (TMSCl) (0.014 mL, 0.11 mmol). After heating at 115° C. for 2 days, the mixture was purified by preparative HPLC to give $N^4$-(1H-benzo[d]imidazol-6-ylamino)-$N^2$-(1H-indazoyl-6-yl)-7-tosyl-7H-pyrrolo[2,3-d]pyrimidin-2,4-diamine, which was diluted with MeOH (1 mL), and a solution of KOH (0.1 g) in H₂O (0.5 mL) was added. After heating at 60° C. for 2 h, the mixture was purified by prep HPLC to give $N^4$-(1H-benzo[d]imidazol-6-ylamino)-$N^2$-(1H-indazoyl-6-yl)-7H-pyrrolo[2,3-d]pyrimidin-2,4-diamine (0.007 g, MS (MH 382.1)) (Compound 5-1).

Example 6

N-(4-(4-(1H-indazol-6-ylamino)-7H-pyrrolo[2,3-d]pyrimidin-2-ylamino)phenyl)-N-methylacetamide

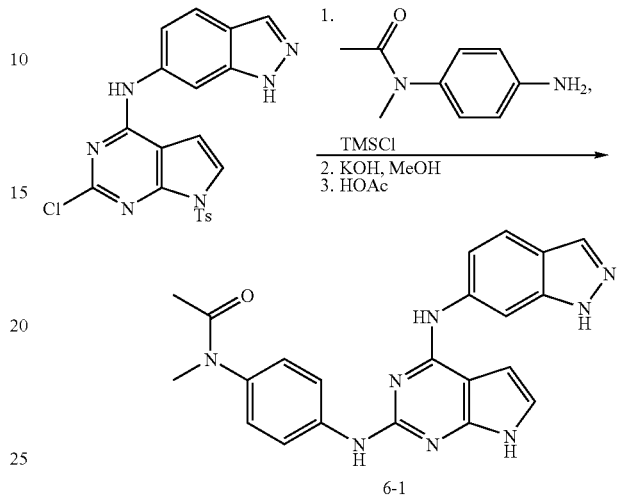

6-1

A mixture of 2-chloro-N-(1H-indazol-6-yl)-7-tosyl-7H-pyrrolo[2,3-d]pyrimidin-4-amine (140 mg, 0.32 mmol), N-(4-aminophenyl)-N-methylacetamide (63 mg, 0.38 mmol) and trimethylsilyl chloride (TMSCl) (0.080 mL, 0.63 mmol) in n-butyl alcohol (4 mL) was heated at 116° C. overnight. More N-(4-aminophenyl)-N-methylacetamide (63 mg, 0.38 mmol) was then added. The mixture was then stirred at 116° C. for an additional 24 h. It was then purified by HPLC to give N-(4-(4-(1H-indazol-6-ylamino)-7-tosyl-7H-pyrrolo[2,3-d]pyrimidin-2-ylamino)phenyl)-N-methylacetamide as a solid (45 mg).

To a solution of N-(4-(4-(1H-indazol-6-ylamino)-7-tosyl-7H-pyrrolo[2,3-d]pyrimidin-2-ylamino)phenyl)-N-methylacetamide (45 mg, 0.080 mmol) in methanol (MeOH) (3 mL), aq. 1N potassium hydroxide (KOH) (0.50 mL, 0.50 mmol) was added. The mixture was then heated at 60° C. for 4 h before it was concentrated in vacuo. The residue was then acidified with acetic acid (HOAc) (0.5 mL) before being purified by HPLC to give the title compound (20 mg). MS 413.1 (M+H) (Compound 6-1).

Example 7

1-(4-(4-(1H-indazol-6-ylamino)-7H-pyrrolo[2,3-d]pyrimidin-2-ylamino)phenyl)piperidin-4-ol

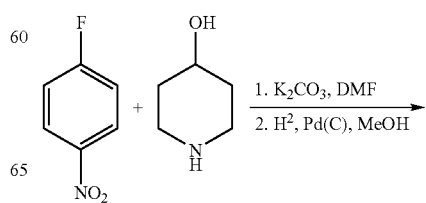

-continued

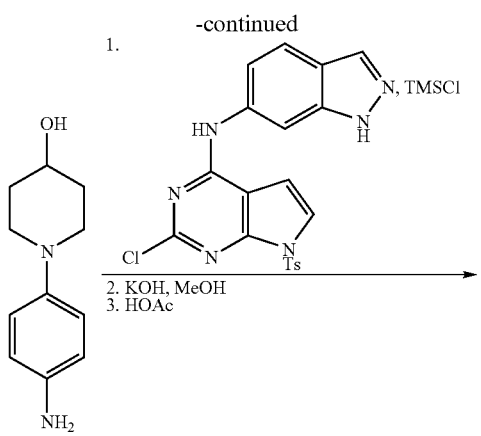

Example 8

N4-(1H-indazol-6-yl)-N2-(4-(4-(methylsulfonyl) piperazin-1-yl)phenyl)-7H-pyrrolo[2,3-d]pyrimidine-2,4-diamine and N4-(1-(methylsulfonyl)-1H-indazol-6-yl)-N2-(4-(4-(methylsulfonyl)piperazin-1-yl) phenyl)-7H-pyrrolo[2,3-d]pyrimidine-2,4-diamine

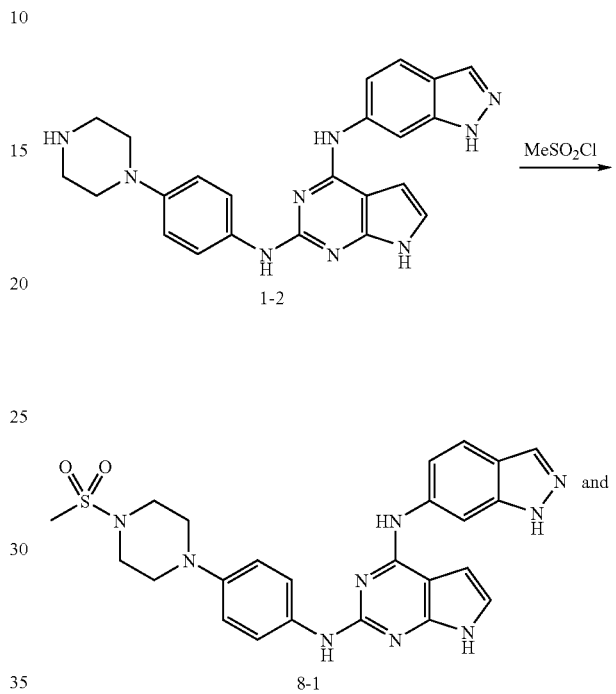

A mixture of 1-fluoro-4-nitrobenzene (0.588 mL, 5.55 mmol), 4-hydroxypiperidine (0.560 g, 5.54 mmol) and $K_2CO_3$ (1.50 g, 10.9 mmol) in dimethylformamide (DMF) (10 mL) was stirred at room temperature overnight. Water was then added to induce precipitation. The yellowish solid was collected by filtration (0.90 g).

A mixture of the yellowish solid (0.90 g, 4.05 mmol) and palladium on carbon (Pd(C)) (10%, 120 mg) in methanol (MeOH) (20 mL) containing aqueous 6N HCl (0.20 mL) was hydrogenated under a balloon of $H_2$ overnight. It was then filtered through celite. The filtrate was concentrated in vacuo to give 1-(4-aminophenyl)piperidin-4-ol as a solid (0.841 g).

A mixture of 2-chloro-N-(1H-indazol-6-yl)-7-tosyl-7H-pyrrolo[2,3-d]pyrimidin-4-amine (61 mg, 0.14 mmol), 1-(4-aminophenyl)piperidin-4-ol (61 mg, 0.32 mmol) and trimethylsilyl chloride (TMSCl) (0.060 mL, 0.48 mmol) in n-butyl alcohol (2 mL) was heated at 116° C. for 96 h. The mixture was then purified by HPLC to give 1-(4-(4-(1H-indazol-6-ylamino)-7-tosyl-7H-pyrrolo[2,3-d]pyrimidin-2-ylamino) phenyl)piperidin-4-ol (11 mg).

To a solution of 1-(4-(4-(1H-indazol-6-ylamino)-7-tosyl-7H-pyrrolo[2,3-d]pyrimidin-2-ylamino)phenyl)piperidin-4-ol (11 mg, 0.018 mmol) in methanol (MeOH) (1 mL), aq. 1N KOH (0.50 mL, 0.50 mmol) was added. The mixture was heated at 60° C. for 24 h. It was then concentrated in vacuo. The residue was acidified with acetic acid (HOAc) (1.0 mL) before being purified by HPLC to give the title compound (1 mg). MS 441.1 (M+H) (Compound 7-1).

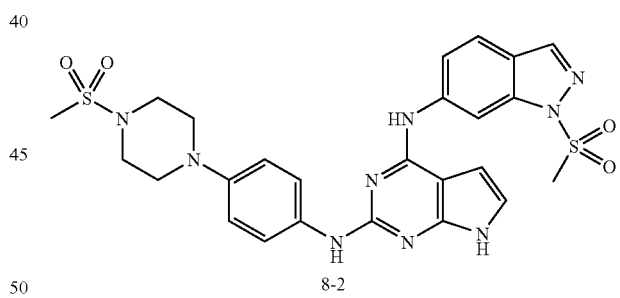

To a suspension of N4-(1H-indazol-6-yl)-N2-(4-(piperazin-1-yl)phenyl)-7H-pyrrolo[2,3-d]pyrimidine-2,4-diamine (9 mg, 0.021 mmol) and triethylamine (TEA) (0.010 mL, 0.072 mmol) in $CH_2Cl_2$ (1 mL) at room temperature, methanesulfonyl chloride ($MeSO_2Cl$) (0.006 mL, 0.077 mmol) was added. After being stirred at room temperature for 3 h, the mixture was concentrated in vacuo. The residue was purified by HPLC to give N4-(1H-indazol-6-yl)-N2-(4-(4-(methylsulfonyl)piperazin-1-yl)phenyl)-7H-pyrrolo[2,3-d] pyrimidine-2,4-diamine (2 mg), MS 504.3 (M+H) (Compound 8-1); and N4-(1-(methylsulfonyl)-1H-indazol-6-yl)-N2-(4-(4-(methylsulfonyl)piperazin-1-yl)phenyl)-7H-pyrrolo[2,3-d]pyrimidine-2,4-diamine (1 mg), MS 582.4 (M+H) (Compound 8-2).

Example 9

N4-(1H-indazol-6-yl)-N2-(4-(methylsulfonyl)phenyl)-7H-pyrrolo[2,3-d]pyrimidine-2,4-diamine

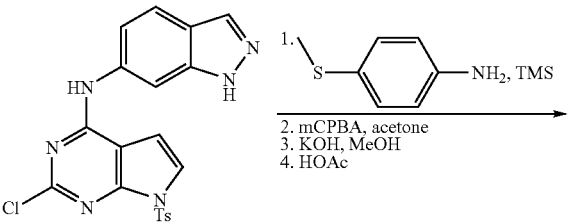

A mixture of 2-chloro-N-(1H-indazol-6-yl)-7-tosyl-7H-pyrrolo[2,3-d]pyrimidin-4-amine (400 mg, 0.912 mmol), 4-(methylthio)aniline (0.227 mL, 1.83 mmol) and trimethylsilyl chloride (TMSCl) (0.231 mL, 1.83 mmol) in n-butyl alcohol (8 mL) was heated at 116° C. for 72 h. Water and ethyl acetate were then added. The organic phase was separated, washed with 5% NaHCO₃, dried over Na₂SO₄, and concentrated in vacuo. The residue was dissolved in CH₃CN (20 mL), and water was added to induced precipitation. The solid was collected by filtration to give N4-(1H-indazol-6-yl)-N2-(4-(methylthio)phenyl)-7-tosyl-7H-pyrrolo[2,3-d]pyrimidine-2,4-diamine (225 mg). The filtrate was also purified by HPLC to give another portion of the desired product (127 mg).

To a solution of N4-(1H-indazol-6-yl)-N2-(4-(methylthio)phenyl)-7-tosyl-7H-pyrrolo[2,3-d]pyrimidine-2,4-diamine (87 mg, 0.16 mmol) in acetone (4 mL), m-chloroperbenzoic acid (mCPBA) (~70%, 58 mg, 0.24 mmol) was added. After being stirred at room temperature for 24 h, the mixture was concentrated in vacuo. The residue was dissolved in dioxane (3 mL), and aq. 1N KOH (1.5 mL, 1.5 mmol) was added. After being stirred at 70° C. for 3 h, the mixture was concentrated in vacuo. The residue was acidified with acetic acid (HOAc) (2 mL) and purified by HPLC to give the title compound (25 mg). MS 420.1 (M+H) (Compound 9-1).

Example 10

N4-(1H-indazol-6-yl)-N2-(4-(methylsulfinyl)phenyl)-7H-pyrrolo[2,3-d]pyrimidine-2,4-diamine and N4-(1H-indazol-6-yl)-N2-(4-(methylthio)phenyl)-7H-pyrrolo[2,3-d]pyrimidine-2,4-diamine

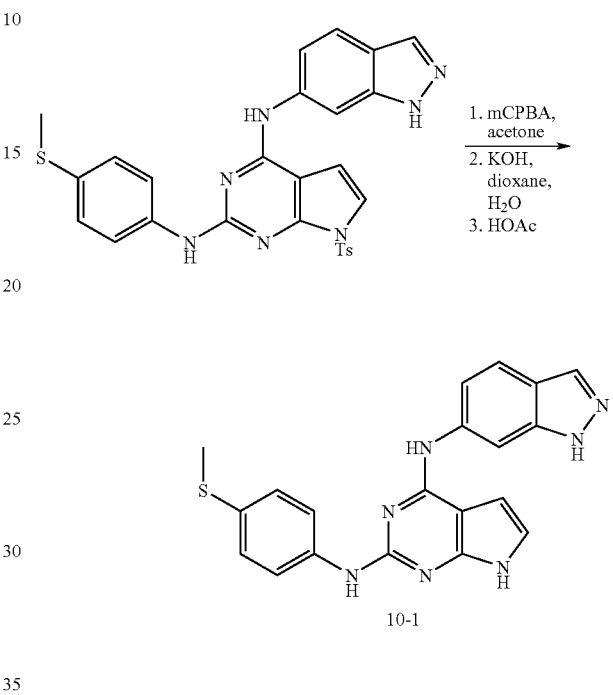

To a solution of N4-(1H-indazol-6-yl)-N2-(4-(methylthio)phenyl)-7-tosyl-7H-pyrrolo[2,3-d]pyrimidine-2,4-diamine (102 mg, 0.19 mmol) in acetone (4 mL), m-chloroperbenzoic acid (mCPBA) (70%, 34 mg, 0.14 mmol) was added. After being stirred at room temperature for 2 h, the mixture was concentrated in vacuo. The residue was dissolved in dioxane (3 mL) and aq. 1N KOH (1.5 mL, 1.5 mmol) was added. After being stirred at 70° C. for 24 h, the mixture was concentrated in vacuo. The residue was acidified with acetic acid (HOAc) (2 mL) before it was purified by HPLC to give N4-(1H-indazol-6-yl)-N2-(4-(methylsulfinyl)phenyl)-7H-pyrrolo[2,3-d]pyrimidine-2,4-diamine (21 mg), MS 404.1 (M+H) (Compound 10-2); and N4-(1H-indazol-6-yl)-N2-(4-(methylthio)phenyl)-7H-pyrrolo[2,3-d]pyrimidine-2,4-diamine (10 mg), MS 388.1 (M+H) (Compound 10-1).

Example 11

4-(4-(1H-indazol-6-ylamino)-7H-pyrrolo[2,3-d]pyrimidin-2-ylamino)benzenesulfonamide

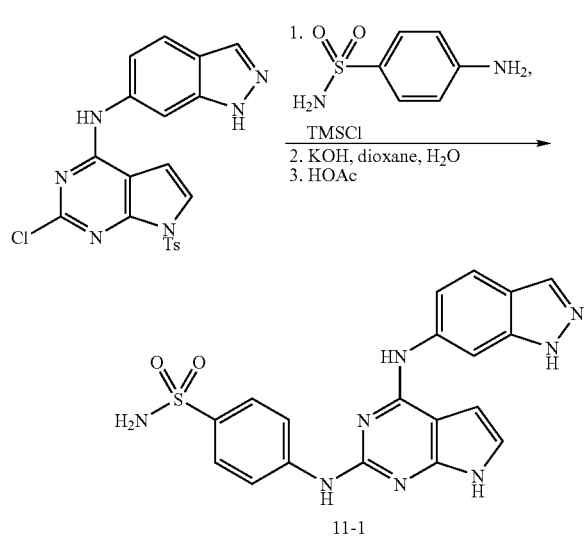

11-1

A mixture of 2-chloro-N-(1H-indazol-6-yl)-7-tosyl-7H-pyrrolo[2,3-d]pyrimidin-4-amine (150 mg, 0.34 mmol), sulfanilamide (125 mg, 0.73 mmol) and trimethylsilyl chloride (TMSCl) (0.100 mL, 0.79 mmol) inn-butyl alcohol (4 mL) was heated at 116° C. for 96 h. The mixture was then purified by HPLC to give 4-(4-(1H-indazol-6-ylamino)-7-tosyl-7H-pyrrolo[2,3-d]pyrimidin-2-ylamino)benzenesulfonamide (110 mg).

To a solution of 4-(4-(1H-indazol-6-ylamino)-7-tosyl-7H-pyrrolo[2,3-d]pyrimidin-2-ylamino)benzenesulfonamide (105 mg, 0.18 mmol) in dioxane (5 mL), aq. 1N KOH (1.50 mL, 1.50 mmol) was added. The mixture was then heated at 70° C. for 4 h. before it was concentrated in vacuo. The residue was then acidified with acetic acid (HOAc) (2.0 mL) and purified by HPLC to give the title compound (15 mg). MS 421.1 (M+H) (Compound 11-1).

Example 12

4-(4-(1H-indazol-6-ylamino)-7H-pyrrolo[2,3-d]pyrimidin-2-ylamino)benzamide

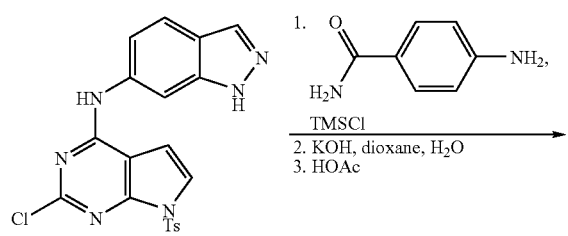

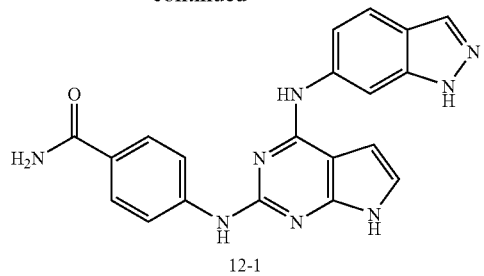

12-1

A mixture of 2-chloro-N-(1H-indazol-6-yl)-7-tosyl-7H-pyrrolo[2,3-d]pyrimidin-4-amine (150 mg, 0.34 mmol), 4-aminobenzamide (93 mg, 0.68 mmol) and trimethylsilyl chloride (TMSCl) (0.100 mL, 0.79 mmol) inn-butyl alcohol (4 mL) was heated at 116° C. for 96 h. The mixture was then purified by HPLC to give 4-(4-(1H-indazol-6-ylamino)-7-tosyl-7H-pyrrolo[2,3-d]pyrimidin-2-ylamino)benzamide (50 mg).

To a solution of 4-(4-(1H-indazol-6-ylamino)-7-tosyl-7H-pyrrolo[2,3-d]pyrimidin-2-ylamino)benzamide (50 mg, 0.093 mmol) in dioxane (3 mL), aq. 1N KOH (1.50 mL, 1.50 mmol) was added. The mixture was heated at 70° C. for 4 h. before it was concentrated in vacuo. The residue was then acidified with acetic acid (HOAc) (2.0 mL) and purified by HPLC to give the title compound (8 mg). MS 385.2 (M+H) (Compound 12-1).

Example 13

N4-(1H-indazol-6-yl)-N2-(4-(4-methylpiperazin-1-yl)phenyl)-7H-pyrrolo[2,3-d]pyrimidine-2,4-diamine

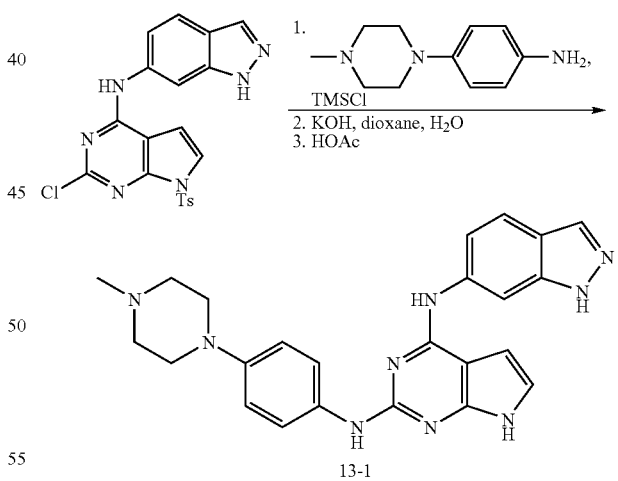

13-1

A mixture of 2-chloro-N-(1H-indazol-6-yl)-7-tosyl-7H-pyrrolo[2,3-d]pyrimidin-4-amine (200 mg, 0.456 mmol), 4-(N-methylpiperazinyl)aniline (88 mg, 0.46 mmol) and trimethylsilyl chloride (TMSCl) (0.375 mL, 2.97 mmol) in n-butyl alcohol (5 mL) was heated at 135° C. for 96 h. The mixture was then purified by HPLC to give N4-(1H-indazol-6-yl)-N2-(4-(4-methylpiperazin-1-yl)phenyl)-7-tosyl-7H-pyrrolo[2,3-d]pyrimidine-2,4-diamine (29 mg).

To a solution of N4-(1H-indazol-6-yl)-N2-(4-(4-methylpiperazin-1-yl)phenyl)-7-tosyl-7H-pyrrolo[2,3-d]pyrimidine-2,4-diamine (29 mg, 0.049 mmol) in methanol (MeOH) (2 mL), aq. 1N KOH (1.0 mL, 1.0 mmol) was added. The mixture was then heated at 60° C. for 4 h. before it was concentrated in vacuo. The residue was then acidified with acetic acid (HOAc) (2.0 mL) and purified by HPLC to give the title compound (10 mg). MS 440.2 (M+H) (Compound 13-1).

Example 14

1-(4-(4-(4-(1H-indazol-5-ylamino)-7H-pyrrolo[2,3-d]pyrimidin-2-ylamino)phenyl)piperazin-1-yl)ethanone and N4-(1H-indazol-5-yl)-N2-(4-(piperazin-1-yl)phenyl)-7H-pyrrolo[2,3-d]pyrimidine-2,4-diamine

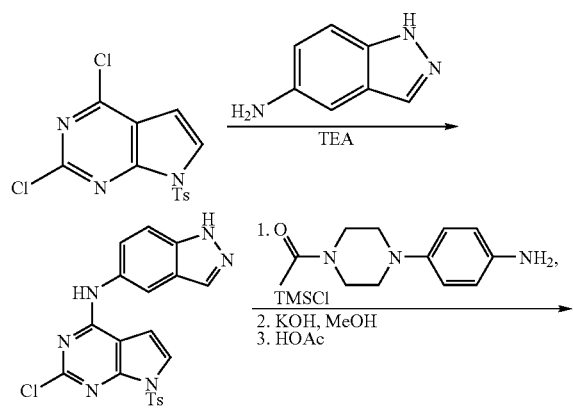

The title compounds were prepared analogously as described for Compounds 1-1 and 1-2 in Example 1. MS 468.1 (M+H) for 1-(4-(4-(4-(1H-indazol-5-ylamino)-7H-pyrrolo[2,3-d]pyrimidin-2-ylamino)phenyl)piperazin-1-yl) ethanone (Compound 14-1); MS 426.1 (M+H) for N4-(1H-indazol-6-yl)-N2-(4-(piperazin-1-yl)phenyl)-7H-pyrrolo[2, 3-d]pyrimidine-2,4-diamine (Compound 14-2).

Example 15

1-(4-(4-(4-(1H-indazol-6-ylamino)-5-methyl-7H-pyrrolo[2,3-d]pyrimidin-2-ylamino)phenyl)piperazin-1-yl)ethanone

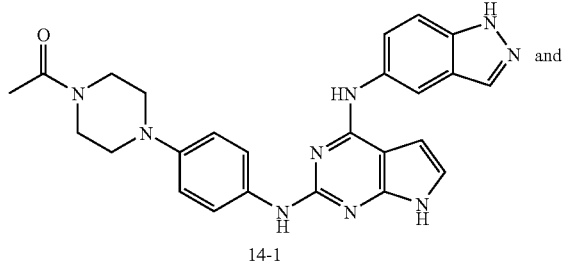

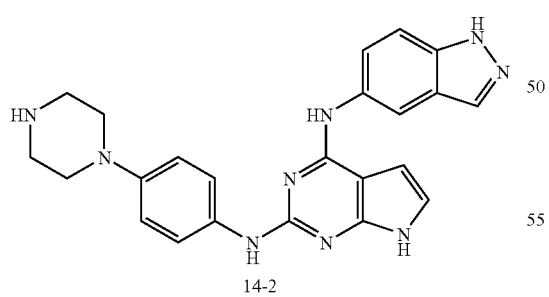

15-1

To a mixture of 2-chloropropionaldehyde dimethyl acetal (5.84 g, 42.1 mmol) in $H_2O$ (26 mL) was added conc. HCl (1 mL). After heating at 95° C. for 15 min (or until the solution turns homogenous), NaOAc (5.2 g) was added to neutralize the excess HCl. The resulting solution was then transferred to a separate flask containing a suspension of 6-aminouracil (4 g, 31.5 mmol) and NaOAc (2.6 g) in $H_2O$ (52 mL). After heating the mixture at reflux overnight, the reaction was cooled and the precipitates were collected by filtration to give 5-methyl-7H-pyrrolo[2,3-d]pyrimidine-2,4-diol (4.8 g, 94% yield).

A suspension of 5-methyl-7H-pyrrolo[2,3-d]pyrimidine-2,4-diol (2.4 g, 0.014 mol) in phenylphosphonic dichloride (PhPOCl$_2$) (8.5 mL) was heated at 185° C. for 5 h, and the resulting dark syrup was poured slowly into ice water. The black precipitates were filtered off and washed with ether, and the filtrate was then extracted with ether. The ether layers were combined and sequentially washed with saturated NaHCO$_3$ and brine before being dried over Na$_2$SO$_4$ and concentrated to give 2,4-dichloro-5-methyl-7H-pyrrolo[2,3-d] pyrimidine as a crude product (0.9 g, 31%).

To a suspension of 2,4-dichloro-5-methyl-7H-pyrrolo[2,3-d]pyrimidine (0.58 g, 2.86 mmol) in CH$_2$Cl$_2$ (6 mL) was added diisopropylethylamine (DIPEA) (0.56 mL, 3.14 mmol) and p-toluenesulfonyl chloride (TsCl) (0.57 g, 3.0 mmol), followed by dimethylaminopyridine (DMAP) (0.035 g, 0.286 mmol). After stirring at ambient temperature for 1 h, the solution was diluted with ethylacetate, and the organic layer was sequentially washed with 1N HCl, saturated NaHCO$_3$, and brine. The organic extract was then dried over Na$_2$SO$_4$ and concentrated to give a crude residue, which was purified by flash column (hexanes/ethyl acetate, 5:1) to yield 2,4-dichloro-5-methyl-7-tosyl-pyrrolo[2,3-d]pyrimidine (0.38 g, 38%).

To a solution of 2,4-dichloro-5-methyl-7-tosyl-pyrrolo[2,3-d]pyrimidine (0.36 g, 1 mmol) in n-butyl alcohol (3 mL) was added 6-aminoindazole (0.27 g, 2 mmol) and DIPEA (0.27 mL, 1.5 mmol) at room temperature. After heating at 90° C. for 4 h, the mixture was diluted with ethylacetate and the organic layer was sequentially washed with 1N HCl, saturated NaHCO$_3$, and brine. The organic extract was then dried over Na$_2$SO$_4$ and concentrated to give a crude residue, which was purified by flash column (Hex/EtOAc=1:1) to give 2-Chloro-N-(1H-indazol-6-yl)-5-methyl-7-tosyl-7H-pyrrolo[2,3-d]pyrimidin-4-amine (0.18 g).

To a mixture of 2-Chloro-N-(1H-indazol-6-yl)-5-methyl-7-tosyl-7H-pyrrolo[2,3-d]pyrimidin-4-amine (0.18 g, 0.4 mmol) and 1-(4-(4-aminophenyl)piperazin-1-yl)ethanone (0.22 g, 1 mmol) in n-butyl alcohol (2 mL) was added trimethylsilyl chloride (TMSCl) (0.026 mL, 0.2 mmol). After heating at 115° C. for 15 h, the mixture was purified by preparative HPLC to give 1-(4-(4-(4-(1H-indazol-6-ylamino)-5-methyl-7-tosyl-7H-pyrrolo[2,3-d]pyrimidin-2-ylamino)phenyl)piperazin-1-yl)ethanone (0.045 g).

To a solution of the above intermediate in methanol (2 mL) was added KOH (0.1 g) in H$_2$O (1 mL). After heating at 60° C. for 2 h, the mixture was purified by preparative HPLC to give 1-(4-(4-(4-(1H-indazol-6-ylamino)-5-methyl-7H-pyrrolo[2,3-d]pyrimidin-2-ylamino)phenyl)piperazin-1-yl)ethanone (0.006 g) MS (MH 482.2) (Compound 15-1).

Example 16

6-(2-(1H-indazol-6-ylamino)-7H-pyrrolo[2,3-d]pyrimidin-4-ylamino)-2,2-dimethyl-2H-benzo[b][1,4]oxazin-3(4H)-one

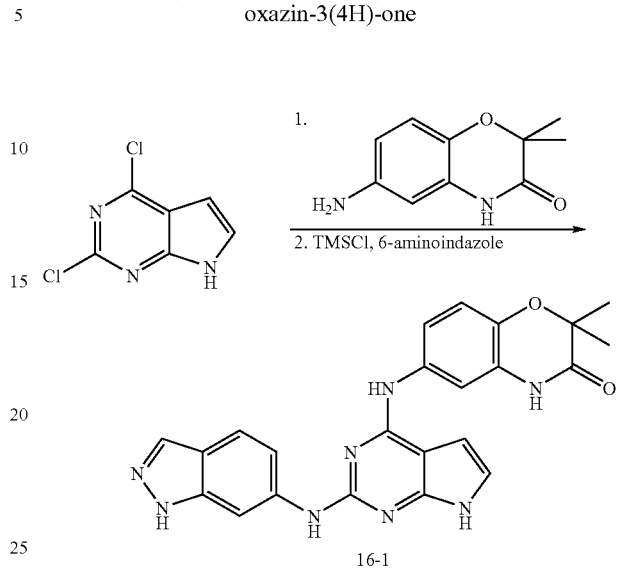

To a solution of 2,4-Dichloro-7H-pyrrolo[2,3-d]pyrimidine (0.056 g, 0.30 mmol) in dimethylsulfoxide (1 mL) was added DIPEA (0.12 mL, 0.60 mmol) and 6-amino-2,2-dimethyl-2H-benzo[b][1,4]oxazin-3(4H)-one (0.085 g, 0.44 mmol). After heating at 100° C. for 15 h, the mixture was diluted with ethylacetate and sequentially washed with saturated NaHCO$_3$ and brine. The organic extracts were dried over Na$_2$SO$_4$ and concentrated to give 6-(2-chloro-7H-pyrrolo[2,3-d]pyrimidin-4-ylamino)-2,2-dimethyl-2H-benzo[b][1,4]oxazin-3(4H)-one (0.05 g).

To a mixture of 6-(2-chloro-7H-pyrrolo[2,3-d]pyrimidin-4-ylamino)-2,2-dimethyl-2H-benzo[b][1,4]oxazin-3(4H)-one (0.050 g) inn-butyl alcohol (0.6 mL) was added 6-aminoindazole (0.028 g) and trimethylsilyl chloride (TMSCl) (0.013 mL). After heating at 115° C. for 15 h, the mixture was purified by preparative HPLC to give 6-(2-(1H-indazol-6-ylamino)-7H-pyrrolo[2,3-d]pyrimidin-4-ylamino)-2,2-dimethyl-2H-benzo[b][1,4]oxazin-3(4H)-one (0.004 g, MS [MH] 441.1) (Compound 16-1).

Example 17

N-(4-(4-(1H-benzo[D]imidazol-6-ylamino)-7H-pyrrolo[2,3-d]pyrimidin-2-ylamino)phenyl)-N-methylacetamide

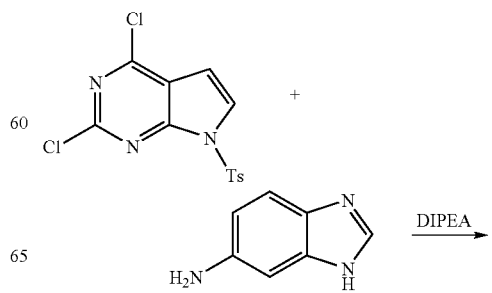

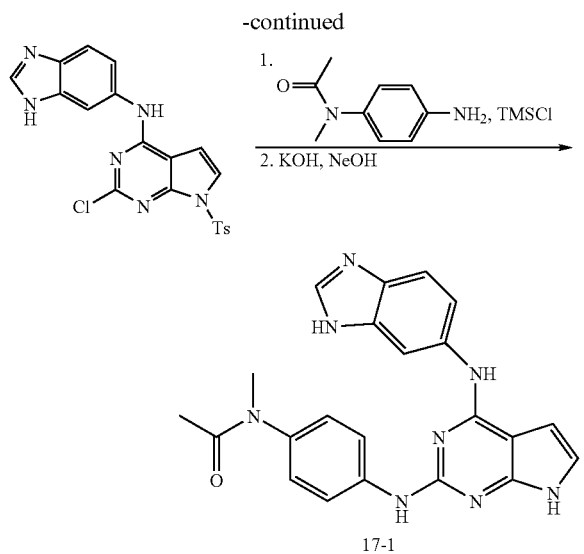

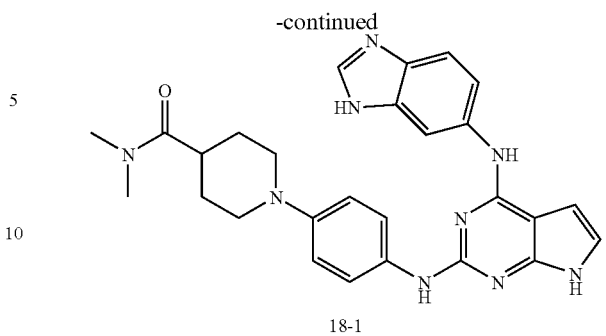

To a solution of 2,4-dichloro-7-tosyl-pyrrolo[2,3-d]pyrimidine (0.1 g, 0.28 mmol) in n-butyl alcohol (1 mL) was added 6-aminoindazole (0.043 g, 0.32 mmol) and DIPEA (0.057 mL, 0.32 mmol) at room temperature. After heating at 80° C. for 15 h, the mixture was diluted with ethyl acetate, and the organic layer was sequentially washed with 1N HCl, Sat NaHCO₃, and brine. The organic extract was dried over Na₂SO₄ and concentrated to give crude N-(1H-benzo[d]imidazol-6-yl)-2-chloro-7-tosyl-7H-pyrrolo[2,3-d]pyrimidin-4-amine (0.105 g).

To a mixture of N-(1H-benzo[d]imidazol-6-yl)-2-chloro-7-tosyl-7H-pyrrolo[2,3-d]pyrimidin-4-amine (0.1 g, 0.24 mmol) in n-butyl alcohol (1 mL) was added N-(4-aminophenyl)-N-methylacetamide (0.078 g, 0.48 mmol) and TMSCl (0.015 mL, 0.12 mmol). After heating at 115° C. for 2 days, the mixture was diluted with methanol (1 mL), and a solution of KOH (0.1 g) in H₂O (0.5 mL) was added. After heating at 60° C. for an additional 2 h, the mixture was purified by preparative HPLC to give N-(4-(4-(1H-benzo[d]imidazol-6-ylamino)-7H-pyrrolo[2,3-d]pyrimidin-2-ylaminophenyl)-N-methylacetamide (0.033 g, MS (MH 413.2) (Compound 17-1).

Example 18

1-(4-(4-(1H-benzo[d]imidazol-6-ylamino)-7H-pyrrolo[2,3-d]pyrimidin-2-ylamino)phenyl)-N,N-dimethylpiperidine-4-carboxamide

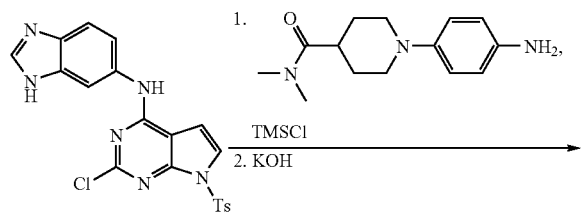

To a mixture of N-(1H-benzo[d]imidazol-6-yl)-2-chloro-7-tosyl-7H-pyrrolo[2,3-d]pyrimidin-4-amine (0.1 g, 0.24 mmol) in n-butyl alcohol (1 mL) was added 1-(4-aminophenyl)-N,N-dimethylpiperidine-4-carboxamide (0.11 g, 0.44 mmol) and TMSCl (0.014 mL, 0.11 mmol). After heating at 115° C. for 15 h, the mixture was diluted with MeOH (1 mL), and a solution of KOH (0.1 g) in H₂O (0.5 mL) was added. After heating at 60° C. for 2 h, the mixture was purified by preparative HPLC to give 1-(4-(4-(1H-benzo[d]imidazol-6-ylamino)-7H-pyrrolo[2,3-d]pyrimidin-2-ylaminophenyl)-N,N-dimethylpiperidine-4-carboxamide (0.02 g, MS (MH 496.3) (Compound 18-1).

Example 19

N4-(benzo[D]thiazol-5-yl)-N2-(1H-indazol-6-yl)-7H-pyrrolo[2,3-d]pyrimidine-2,4-diamine

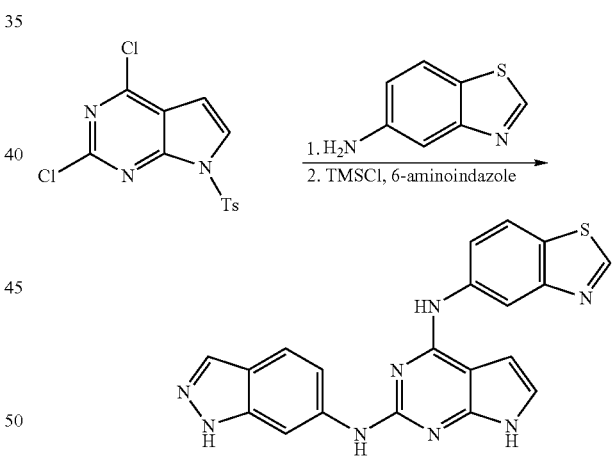

To a solution of 2,4-dichloro-7-tosyl-pyrrolo[2,3-d]pyrimidine (0.1 g, 0.28 mmol) in n-butyl alcohol (0.8 mL) was added 5-aminobenzothiazole (0.046 g, 0.31 mmol) and DIPEA (0.1 mL, 0.56 mmol) at room temperature. After heating at 90° C. for 3 h, the mixture was diluted with H₂O, and the precipitates were collected by filtration to give N-(2-chloro-7-tosyl-7H-pyrrolo[2,3-d]pyrimidin-4-yl)benzothiazol-5-amine (0.19 g).

To a mixture of the above intermediate in n-butyl alcohol (1 mL) was added 6-aminoindazole (0.056 g, 0.42 mmol) and TMSCl (0.018 mL, 0.14 mmol). After heating at 115° C. for 15 h, the mixture was purified by preparative HPLC to give N4-(benzo[d]thiazol-5-yl)-N2-(1H-indazol-6-yl)-7-tosyl- 7H-pyrrolo[2,3-d]pyrimidine-2,4-diamine, which was diluted with methanol (1 mL), and a solution of KOH (0.1 g) in H₂O (0.5 mL) was added. After heating at 60° C. for 2 h, the mixture was purified by preparative HPLC to give N4-(benzo[d]thiazol-5-yl)-N2-(1H-indazol-6-yl)-7H-pyrrolo[2,3-d]pyrimidine-2,4-diamine (0.004 g, MS (MH 399.1) (Compound 19-1).

Example 20

N4-(benzo[d]thiazol-6-yl)-N2-(1H-indazol-6-yl)-7H-pyrrolo[2,3-d]pyrimidine-2,4-diamine

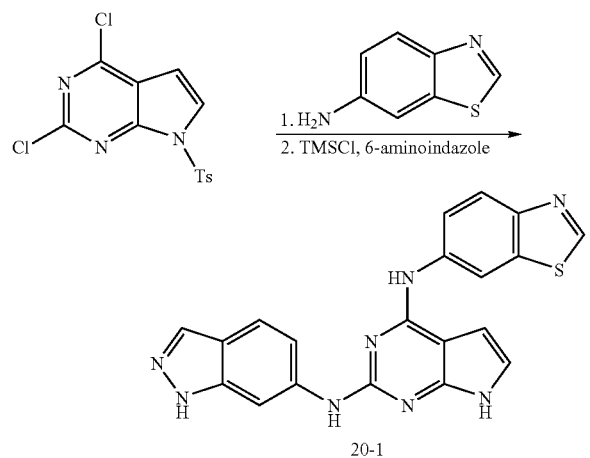

20-1

To a solution of 2,4-dichloro-7-tosyl-pyrrolo[2,3-d]pyrimidine (0.1 g, 0.28 mmol) in n-butyl alcohol (0.8 mL) was added 6-aminobenzothiazole (0.046 g, 0.31 mmol) and DIPEA (0.1 mL, 0.56 mmol) at room temperature. After heating at 90° C. for 3 h, the mixture was diluted with H₂O, and the precipitates were collected by filtration to give N-(2-chloro-7-tosyl-7H-pyrrolo[2,3-d]pyrimidin-4-yl)benzolthiazol-5-amine (0.19 g).

To a mixture of the above intermediate in n-butyl alcohol (1 mL) was added 6-aminoindazole (0.056 g, 0.42 mmol) and TMSCl (0.018 mL, 0.14 mmol). After heating at 115° C. for 15 h, the mixture was purified by preparative HPLC to give N4-(benzo[d]thiazol-6-yl)-N2-(1H-indazol-6-yl)-7-tosyl-7H-pyrrolo[2,3-d]pyrimidine-2,4-diamine, which was diluted with MeOH (1 mL), and a solution of KOH (0.1 g) in H₂O (0.5 mL) was added. After heating at 60° C. for 2 h, the mixture was purified by preparative HPLC to give N4-(benzo[d]thiazol-6-yl)-N2-(1H-indazol-6-yl)-7H-pyrrolo[2,3-d]pyrimidine-2,4-diamine (0.004 g, MS (MH 399.2) (Compound 20-1).

Example 21

1-(4-(4-(4-(1H-indazol-6-ylamino)-5-ethyl-7H-pyrrolo[2,3-d]pyrimidin-2-ylamino)phenyl)piperazin-1-yl)ethanone

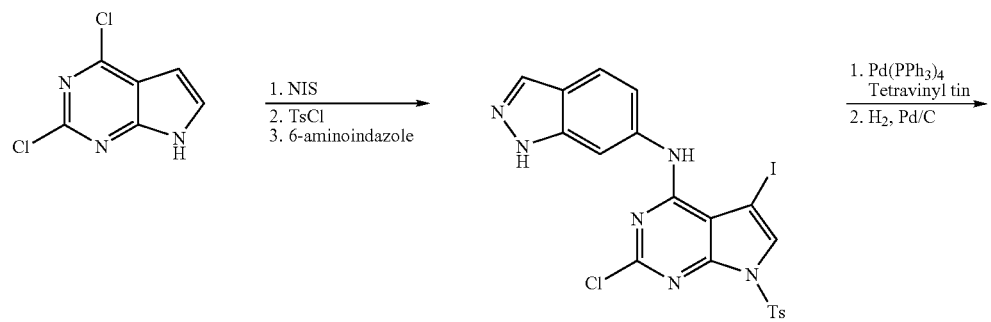

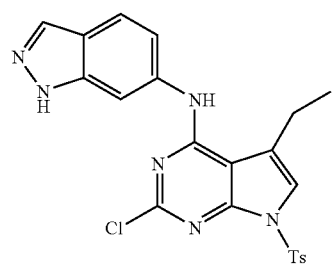

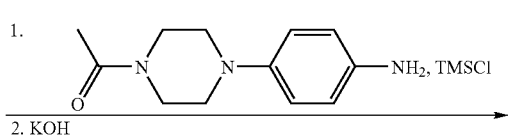

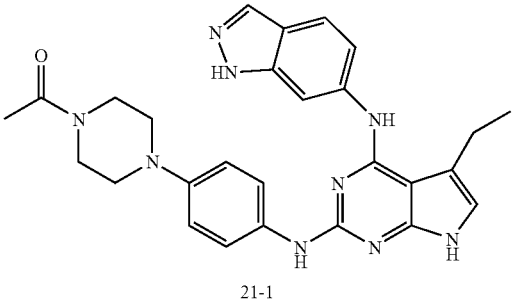

21-1

To a suspension of 2,4-dichloro-7H-pyrrolo[2,3-d]pyrimidine (2.0 g, 10.6 mmol) in CH₂Cl₂ (32 mL) was added N-iodosuccinimide (NIS) (2.4 g, 10.6 mmol) at room temperature. After stirring for 1 h, the resulting precipitates were collected by filtration to give 2,4-dichloro-5-iodo-7H-pyrrolo[2,3-d]pyrimidine (1.8 g).

To a mixture of 2,4-dichloro-5-iodo-7H-pyrrolo[2,3-d]pyrimidine (1.80 g, 5.73 mmol) in CH₂Cl₂ (20 mL) was added p-toluenesulfonyl chloride (TsCl) (1.09 g, 5.73 mmol) and triethylamine (TEA) (1.60 mL, 11.46 mmol), followed by dimethylaminopyridine (DMAP) (70 mg, 0.573 mmol). After stirring for 1 h at room temperature, the solution was concentrated, and the residue was partitioned between ethyl acetate and H₂O. The organic layer was separated, washed sequentially with 1N HCl and 5% NaHCO₃. The organic extracts were dried over Na₂SO₄ and concentrated to give 2,4-dichloro-5-iodo-7-tosyl-7H-pyrrolo[2,3-d]pyrimidine (2.0 g).

To a mixture of 2,4-dichloro-5-iodo-7-tosyl-7H-pyrrolo[2,3-d]pyrimidine (1.5 g, 3.2 mmol) in n-butyl alcohol (12 mL) was added 6-aminoindazole (0.47 g, 3.52 mol) and DIPEA (0.86 mL, 4.80 mmol). After heating at 45° C. for 15 h, the mixture was cooled to room temperature, and the resulting precipitates were collected by filtration to give 2-chloro-N-(1H-indazol-6-yl)-5-iodo-7-tosyl-7H-pyrrolo[2,3-d]pyrimidin-4-amine (1.1 g).

To a solution of 2-chloro-N-(1H-indazol-6-yl)-5-iodo-7-tosyl-7H-pyrrolo[2,3-d]pyrimidin-4-amine (0.45 g, 0.8 mmol) in dimethylformamide (2.0 mL) was added tetravinyltin (0.29 mL, 1.6 mmol) and tetrakis(triphenylphosphine)palladium(0) (Pd(PPh₃)₄) (0.092 g, 0.08 mmol). After degassing, the mixture was heated at 60° C. for 15 h. before it was diluted with EtOAc, and washed sequentially with Sat. NaHCO₃ and brine. The organic extract was dried over Na₂SO₄ and concentrated to give a crude residue. Purification by flash column chromatography (Hexane/EtOAc=1:1) gave 2-chloro-N-(1H-indazol-6-yl)-5-vinyl-7-tosyl-7H-pyrrolo[2,3-d]pyrimidin-4-amine (0.11 g).

To a solution of 2-chloro-N-(1H-indazol-6-yl)-5-vinyl-7-tosyl-7H-pyrrolo[2,3-d]pyrimidin-4-amine (0.11 g) in ethylacetate (5 mL) was added palladium on carbon (Pd/C) (0.1 g). The flask was then charged with H₂. After 3 h, the Pd/C was filtered off, and the filtrate was concentrated to give 2-chloro-N-(1H-indazol-6-yl)-5-ethyl-7-tosyl-7H-pyrrolo[2,3-d]pyrimidin-4-amine (84 mg).

To a mixture of 2-Chloro-N-(1H-indazol-6-yl)-5-ethyl-7-tosyl-7H-pyrrolo[2,3-d]pyrimidin-4-amine (0.08 g, 0.17 mmol) and 1-(4-(4-aminophenyl)piperazin-1-yl)ethanone (0.075 g, 0.34 mmol) in n-butyl alcohol (2 mL) was added TMSCl (0.011 mL, 0.086 mmol). After heating at 115° C. for 48 h, the mixture was purified by preparative HPLC to give 1-(4-(4-(4-(1H-indazol-6-ylamino)-5-methyl-7-tosyl-7H-pyrrolo[2,3-d]pyrimidin-2-ylamino)phenyl)piperazin-1-yl)ethanone (0.02 g).

To a solution of the above intermediate in MeOH (0.5 mL) and p-dioxane (1 mL) was added KOH (0.1 g) in H₂O (0.5 mL). After heating at 60° C. for 1 h, the mixture was purified by preparative HPLC to give 1-(4-(4-(4-(1H-indazol-6-ylamino)-5-ethyl-7H-pyrrolo[2,3-d]pyrimidin-2-ylamino)phenyl)piperazin-1-yl)ethanone (0.002 g) MS (MH 496.2) (Compound 21-1).

Example 22

N4-(1-methyl-1H-indazol-6-yl)-N2-(4-(piperazin-1-yl)phenyl)-7H-pyrrolo[2,3-d]pyrimidine-2,4-diamine and 1-(4-(4-(4-(1-methyl-1H-indazol-6-ylamino)-7H-pyrrolo[2,3-d]pyrimidin-2-ylamino)phenyl)piperazin-1-yl)ethanone

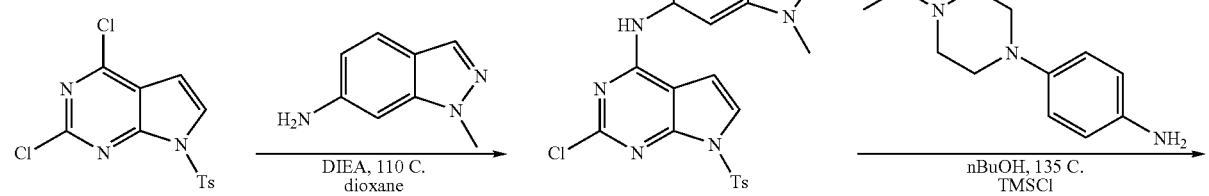

-continued

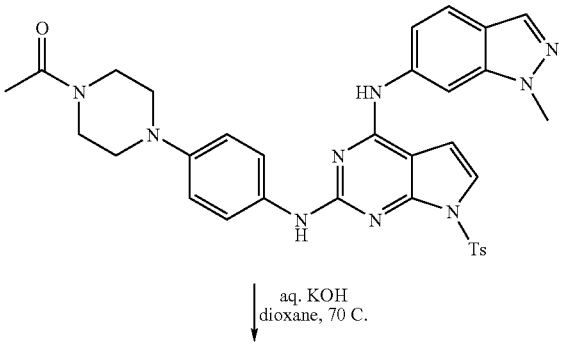

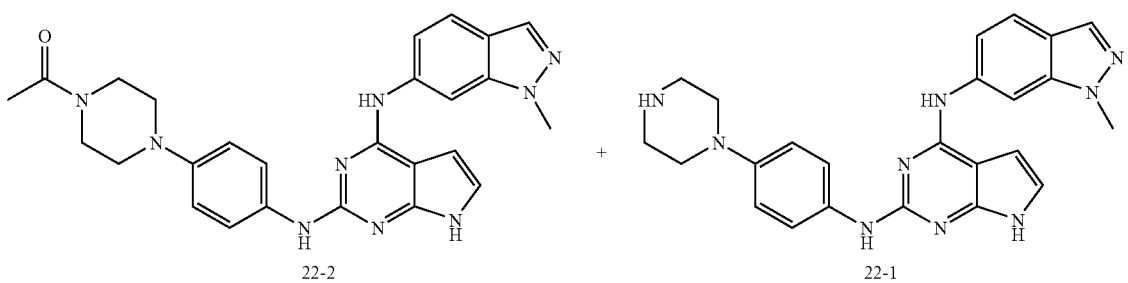

A solution of 2,4-dichloro-7-tosyl-7H-pyrrolo[2,3-d]pyrimidine (200 mg, 0.585 mmol), 1-methyl-indazol-6-ylamine (86 mg, 0.585 mmol) and DIEA (0.250 mL, 1.44 mmol) in dioxane (5 mL) was stirred at 110° C. for 20 h. EtOAc and H₂O were added. The organic phase was separated, washed with 1N HCl, then with 5% NaHCO₃, dried over Na₂SO₄, concentrated in vacuo to give 2-chloro-N-(1-methyl-1H-indazol-6-yl)-7-tosyl-7H-pyrrolo[2,3-d]pyrimidin-4-amine (216 mg).

A mixture of 2-chloro-N-(1-methyl-1H-indazol-6-yl)-7-tosyl-7H-pyrrolo[2,3-d]pyrimidin-4-amine (108 mg, 0.239 mmol), 1-(4-(4-aminophenyl)piperazin-1-yl)ethanone (78 mg, 0.356 mmol) and TMSCl (0.100 mL, 0.791 mmol) in nBuOH (2 mL) was stirred at 135° C. for 20 h. nBuOH was removed in vacuo. The residue was purified by HPLC to give 1-(4-(4-(4-(1-methyl-1H-indazol-6-ylamino)-7H-pyrrolo[2,3-d]pyrimidin-2-ylamino)phenyl)piperazin-1-yl)ethanone (30 mg).

To a solution of 1-(4-(4-(4-(1-methyl-1H-indazol-6-ylamino)-7H-pyrrolo[2,3-d]pyrimidin-2-ylamino)phenyl) piperazin-1-yl)ethanone (30 mg, 0.047 mmol) in dioxane (2 mL), aq. 1N KOH (2 mL, 2.00 mmol) was added. The mixture was stirred at 70° C. for 3 h. HOAc (0.3 mL) was added. The mixture was purified by HPLC to give N4-(1-methyl-1H-indazol-6-yl)-N2-(4-(piperazin-1-yl)phenyl)-7H-pyrrolo[2,3-d]pyrimidine-2,4-diamine (3 mg), MS 440.3 (M+H) (Compound 22-1); and 1-(4-(4-(4-(1-methyl-1H-indazol-6-ylamino)-7H-pyrrolo[2,3-d]pyrimidin-2-ylamino)phenyl) piperazin-1-yl)ethanone (7 mg), MS 482.3 (M+H) (Compound 22-2).

Example 23

4-(4-(1-methyl-1H-indazol-6-ylamino)-7H-pyrrolo[2,3-d]pyrimidin-2-ylamino)benzamide

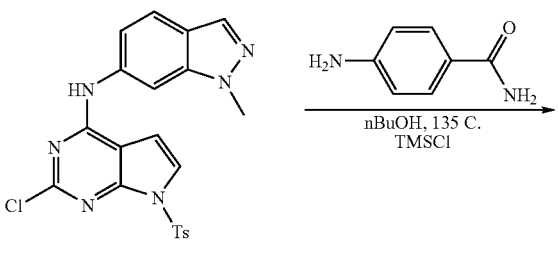

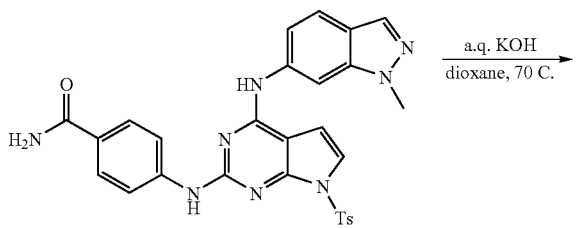

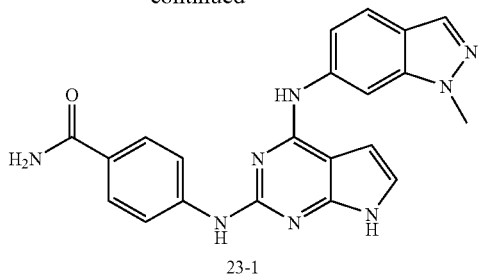

23-1

A mixture of 2-chloro-N-(1-methyl-1H-indazol-6-yl)-7-tosyl-7H-pyrrolo[2,3-d]pyrimidin-4-amine (90 mg, 0.20 mmol), 4-aminobenzamide (55 mg, 0.40 mmol) and TMSCl (0.200 mL, 1.58 mmol) in nBuOH (2 mL) was stirred at 135° C. for 44 h. nBuOH was removed in vacuo. The residue was purified by HPLC to give 4-(4-(1-methyl-1H-indazol-6-ylamino)-7-tosyl-7H-pyrrolo[2,3-d]pyrimidin-2-ylamino)benzamide (12 mg).

To a solution of 4-(4-(1-methyl-1H-indazol-6-ylamino)-7-tosyl-7H-pyrrolo[2,3-d]pyrimidin-2-ylamino)benzamide (12 mg, 0.022 mmol) in dioxane (2 mL), aq. 1N KOH (2 mL, 2.00 mmol) was added. The mixture was stirred at 70° C. for 20 h. HOAc (1.0 mL) was added. The mixture was purified by HPLC to give the titled compound (2 mg). MS 399.2 (M+H) (Compound 23-1).

Example 24

6-(4-(1'-methyl-1H-indazol-5-ylamino)-7H-pyrrolo[2,3-d]pyrimidin-2-ylamino)-3,4-dihydroquinolin-2(1H)-one

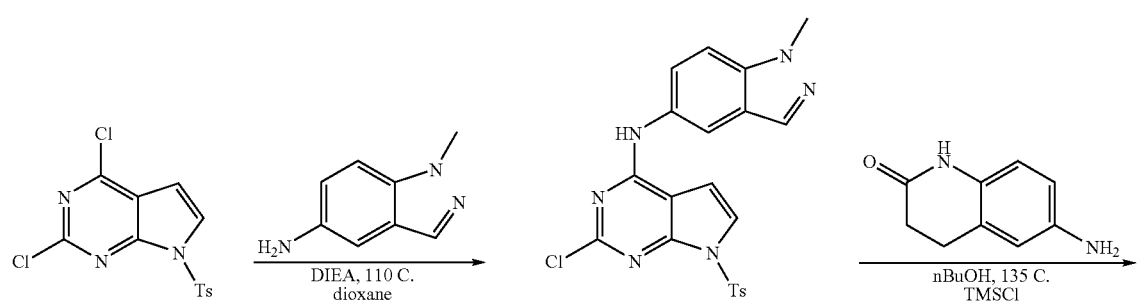

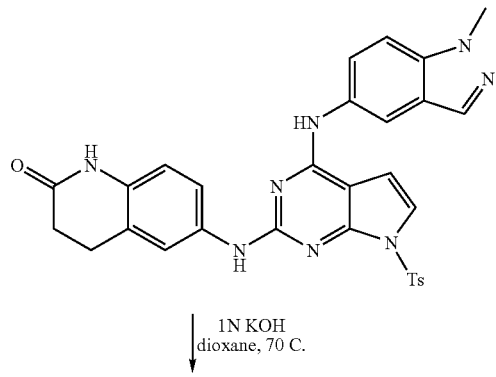

1N KOH
dioxane, 70 C.

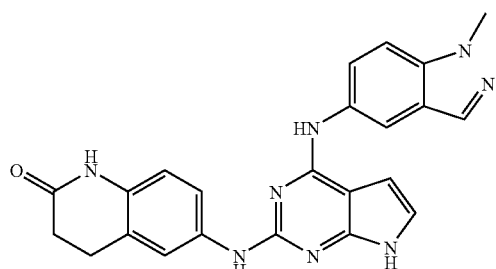

24-1

A solution of 2,4-dichloro-7-tosyl-7H-pyrrolo[2,3-d]pyrimidine (275 mg, 0.804 mmol), 1-methyl-indazol-5-ylamine (118 mg, 0.803 mmol) and DIEA (0.350 mL, 2.01 mmol) in dioxane (7 mL) was stirred at 110° C. for 20 h. EtOAc and H₂O were added. The organic phase was separated, washed with 1N HCl, then with 5% NaHCO₃, dried over Na₂SO₄, concentrated in vacuo to give 2-chloro-N-(1-methyl-1H-indazol-5-yl)-7-tosyl-7H-pyrrolo[2,3-d]pyrimidin-4-amine (316 mg).

A mixture of 2-chloro-N-(1-methyl-1H-indazol-5-yl)-7-tosyl-7H-pyrrolo[2,3-d]pyrimidin-4-amine (1158 mg, 0.349 mmol), 6-amino-3,4-dihydroquinolin-2(1H)-one (113 mg, 0.697 mmol) and TMSCl (0.300 mL, 2.37 mmol) in nBuOH (3 mL) was stirred at 135° C. for 44 h. nBuOH was removed in vacuo. The residue was purified by HPLC to give 6-(4-(1-methyl-1H-indazol-5-ylamino)-7-tosyl-7H-pyrrolo[2,3-d]pyrimidin-2-ylamino)-3,4-dihydroquinolin-2(1H)-one (25 mg).

To a solution of 6-(4-(1-methyl-1H-indazol-5-ylamino)-7-tosyl-7H-pyrrolo[2,3-d]pyrimidin-2-ylamino)-3,4-dihydroquinolin-2(1H)-one (25 mg, 0.043 mmol) in dioxane (2 mL), aq. 1N KOH (2 mL, 2.00 mmol) was added. The mixture was stirred at 70° C. for 4 h. HOAc (1.0 mL) was added. The mixture was purified by HPLC to give the titled compound (3 mg). MS 425.2 (M+H) (Compound 24-1).

Example 25

4-(4-(1-methyl-1H-indazol-5-ylamino)-7H-pyrrolo[2,3-d]pyrimidin-2-ylamino)benzamide

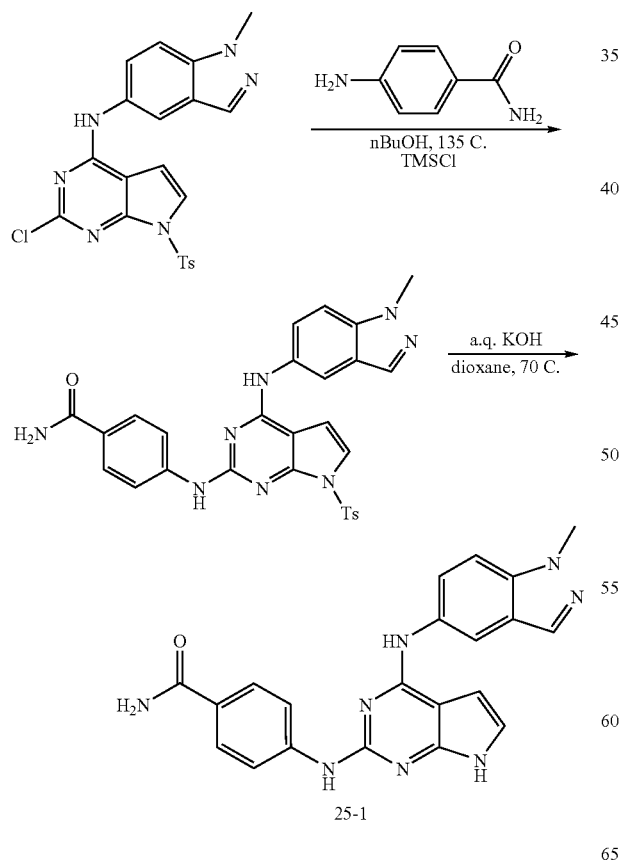

A mixture of 2-chloro-N-(1-methyl-1H-indazol-5-yl)-7-tosyl-7H-pyrrolo[2,3-d]pyrimidin-4-amine (158 mg, 0.349 mmol), 4-aminobenzamide (100 mg, 0.735 mmol) and TMSCl (0.300 mL, 2.37 mmol) in nBuOH (3 mL) was stirred at 135° C. for 20 h. nBuOH was removed in vacuo. The residue was purified by HPLC to give 4-(4-(1-methyl-1H-indazol-5-ylamino)-7-tosyl-7H-pyrrolo[2,3-d]pyrimidin-2-ylamino)benzamide (40 mg).

To a solution of 4-(4-(1-methyl-1H-indazol-5-ylamino)-7-tosyl-7H-pyrrolo[2,3-d]pyrimidin-2-ylamino)benzamide (40 mg, 0.072 mmol) in dioxane (2 mL), aq. 1N KOH (1.8 mL, 1.80 mmol) was added. The mixture was stirred at 70° C. for 20 h. HOAc (1.0 mL) was added. The mixture was purified by HPLC to give the titled compound (7 mg). MS 399.2 (M+H) (Compound 25-1).

Example 26

4-(4-(1H-indazol-4-ylamino)-7H-pyrrolo[2,3-d]pyrimidin-2-ylamino)benzamide

4-Aminoindazole

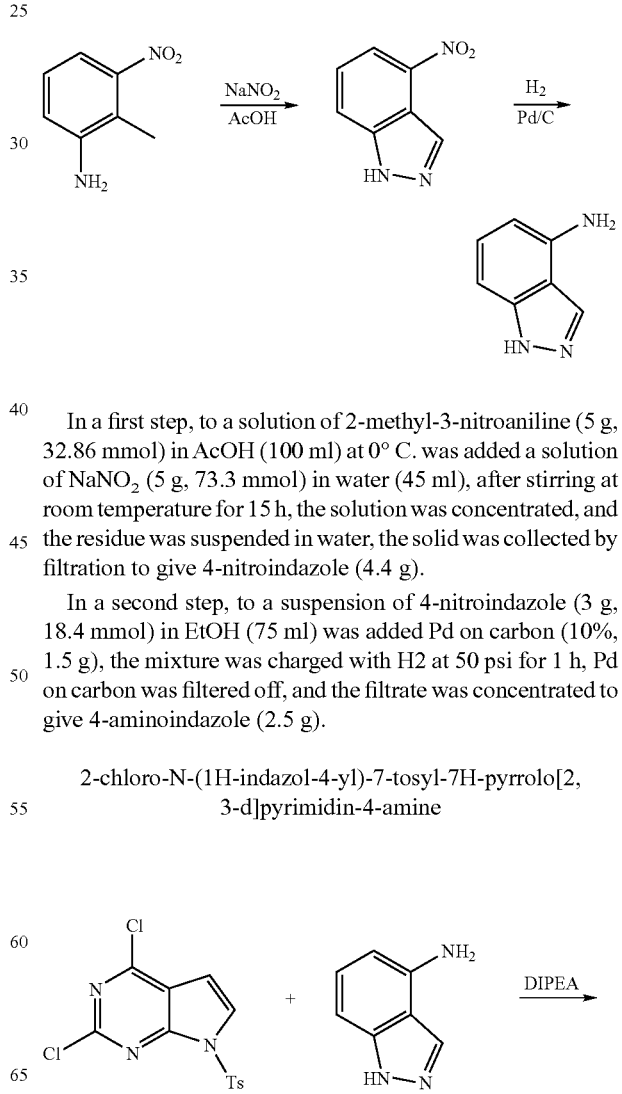

In a first step, to a solution of 2-methyl-3-nitroaniline (5 g, 32.86 mmol) in AcOH (100 ml) at 0° C. was added a solution of NaNO₂ (5 g, 73.3 mmol) in water (45 ml), after stirring at room temperature for 15 h, the solution was concentrated, and the residue was suspended in water, the solid was collected by filtration to give 4-nitroindazole (4.4 g).

In a second step, to a suspension of 4-nitroindazole (3 g, 18.4 mmol) in EtOH (75 ml) was added Pd on carbon (10%, 1.5 g), the mixture was charged with H2 at 50 psi for 1 h, Pd on carbon was filtered off, and the filtrate was concentrated to give 4-aminoindazole (2.5 g).

2-chloro-N-(1H-indazol-4-yl)-7-tosyl-7H-pyrrolo[2,3-d]pyrimidin-4-amine

-continued

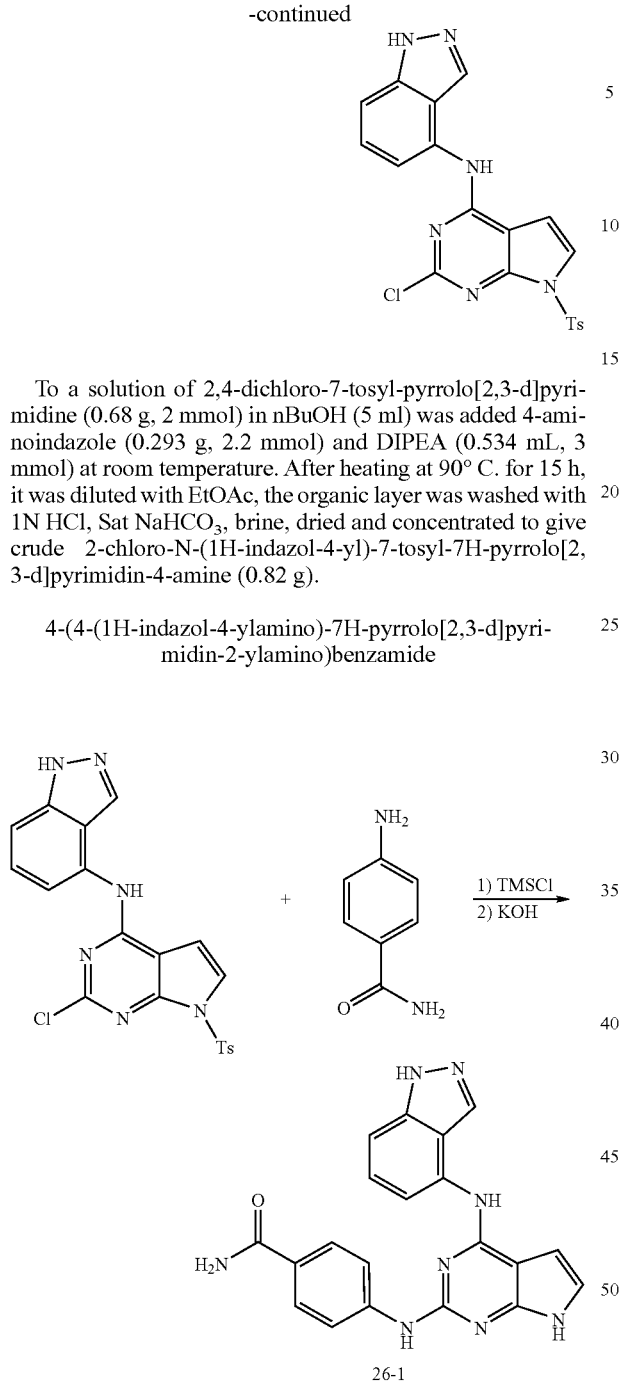

To a solution of 2,4-dichloro-7-tosyl-pyrrolo[2,3-d]pyrimidine (0.68 g, 2 mmol) in nBuOH (5 ml) was added 4-aminoindazole (0.293 g, 2.2 mmol) and DIPEA (0.534 mL, 3 mmol) at room temperature. After heating at 90° C. for 15 h, it was diluted with EtOAc, the organic layer was washed with 1N HCl, Sat NaHCO₃, brine, dried and concentrated to give crude 2-chloro-N-(1H-indazol-4-yl)-7-tosyl-7H-pyrrolo[2,3-d]pyrimidin-4-amine (0.82 g).

4-(4-(1H-indazol-4-ylamino)-7H-pyrrolo[2,3-d]pyrimidin-2-ylamino)benzamide

To a mixture of 2-chloro-N-(1H-indazol-4-yl)-7-tosyl-7H-pyrrolo[2,3-d]pyrimidin-4-amine (0.12 g, 0.27 mmol) and 4-aminobenzamide (0.055 g, 0.4 mmol) in nBuOH (1 ml) was added TMSCl (0.017 ml, 0.14 mmol). After heating at 120° C. for 24 h, the mixture was purified by preparative HPLC to give 4-(4-(1H-indazol-4-ylamino)-7-tosyl-pyrrolo[2,3-d]pyrimidin-2-ylamino)benzamide (0.016 g).

To a solution of the above intermediate in MeOH (0.5 mL) was added KOH (0.1 g) in H2O (0.5 mL). After heating at 60° C. for 1 h, it was purified by prep HPLC to give 4-(4-(1H-indazol-4-ylamino)-7H-pyrrolo[2,3-d]pyrimidin-2-ylamino)benzamide (0.01 g, MS (MH 385.4)) (Compound 26-1)

Example 27

1-(4-(4-(4-(1H-indazol-4-ylamino)-7H-pyrrolo[2,3-d]pyrimidin-2-ylamino)phenyl)piperazin-1-yl)ethanone

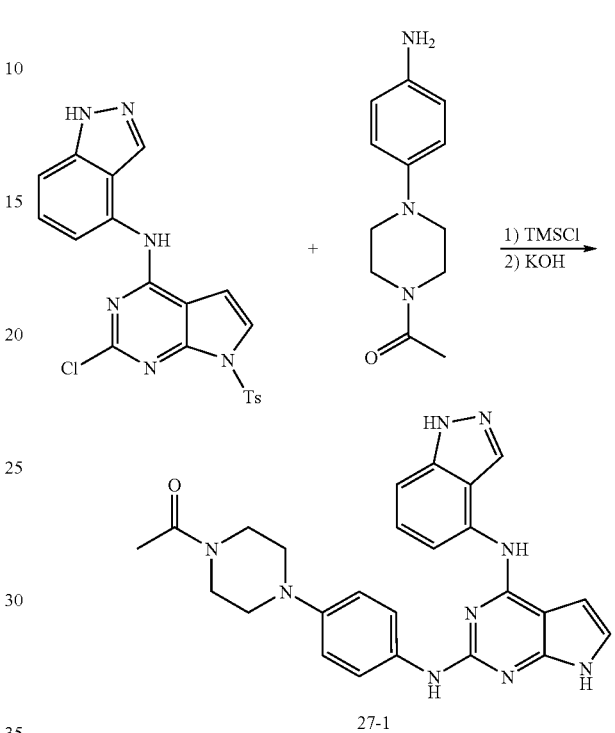

To a mixture of 2-chloro-N-(1H-indazol-4-yl)-7-tosyl-7H-pyrrolo[2,3-d]pyrimidin-4-amine (0.12 g, 0.27 mmol) and 1-(4-(4-aminophenyl)piperazin-1-yl)ethanone (0.12 g, 0.54 mmol) in nBuOH (2 ml) was added TMSCl (0.017 mL, 0.14 mmol). After heating at 115° C. for 24 h, the mixture was purified by preparative HPLC to give 1-(4-(4-(4-(1H-indazol-4-ylamino)-7-tosyl-7H-pyrrolo[2,3-d]pyrimidin-2-ylamino)phenyl)piperazin-1-yl)ethanone.

To a solution of the above intermediate in MeOH (3 ml) was added KOH (0.1 g) in H2O (1.5 ml). After heating at 60° C. for 1 h, it was purified by prep HPLC to give 1-(4-(4-(4-(1H-indazol-4-ylamino)-5-ethyl-7H-pyrrolo[2,3-d]pyrimidin-2-ylamino)phenyl)-piperazin-1-yl)ethanone (0.017 g, MS (MH 468.4)) (Compound 27-1).

Example 28

Activity of Representative Compounds in Biological Assays

Inhibition of Syk Tyrosine Phosphorylation Activity

Potency of candidate molecules for inhibiting Syk tyrosine phosphorylation activity was also assessed by measuring the ability of a test compound to inhibit Syk-mediated tyrosine phosphorylation of a Syk-specific substrate. Syk tyrosine phosphorylation activity was measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit Syk tyrosine phosphorylation activity, molecules were reconstituted in 30% DMSO and serially diluted 1:3 with the final dilution containing DMSO in the absence of the candidate molecule. The final DMSO concentration in the assay was 3%. Kinase assays were performed as a two-part reaction. The first reaction was a kinase reaction which comprised a candidate molecule, full length active recombinant Syk enzyme (Cell Signaling Technology, Danvers, Mass.) and biotin-labeled Syk-specific substrate biotin-DEEDYESP-OH while the second reaction involved termination of the kinase reaction and the simultaneous addition of the detection reagents-europium-labeled anti-phosphotyrosine reagent (Eu-W1024-PY100, Perkin Elmer, Boston, Mass.) and Streptavidin-Allophycocyanin detection reagent (SA-APC, Prozyme, San Leandro, Calif.).

The kinase reaction was performed in a black U-bottom 96-well microtitre plate. The final reaction volume was 50 μL and contained a final concentration of 1 nM active Syk enzyme, 550 nM Syk-substrate, and 100 μM ATP diluted in a buffer containing 50 mM Tris pH 7.5, 5 mM $MgCl_2$, and 1 mM dithiothreitol. The reaction was allowed to proceed for 1 hour at room temperature. The stop buffer contained 100 mM Tris pH 7.5, 300 mM NaCl, 20 mM EDTA, 0.02% Brij35, and 0.5% bovine serum albumin. The detection reagents were added to the reaction mixture at the following dilutions—1:500 for Eu-W1024-PY100 and 1:250 for SA-APC. The kinase reaction was terminated by the addition of 50 μL stop buffer containing the detection reagents. The detection was allowed to proceed for 1 hr at room temperature. Detection of the phosphorylated substrate in the absence and presence of inhibitors was measured in the TR-FRET instrument, Analyst HT, (Molecular Probes, Sunnyvale, Calif.) and the condition for measurements were set up using Criterion Host Release 2.0 (Molecular Probes, Sunnyvale, Calif.). The settings used were as follows: excitation 360 nm, emission 665-7.5 nm, beam splitter 350 nm 50/50, flash 100 pulses, delay 60 us, integration 400 us, z-height 2 mm. Inhibition of Syk-tyrosine kinase activity was calculated as the maximum response observed in the presence of inhibitor, compared to that in the absence of inhibitor. $IC_{50}$s were then derived by non-linear regression analysis.

Each of the compounds of Examples 1-27 were assayed for inhibition of Syk trosine phosphorylation activity as described above and found to have $IC_{50}$ values of less than 1 μM.

Convulxin-Induced Aggregation Assay

For preparation of human platelet-rich plasma (PRP) for aggregation assays, human venous blood was collected from healthy, drug-free volunteers into 0.38% sodium citrate (0.013 M, pH 7.0 final). PRP was prepared by centrifugation of whole blood at 160×g for 20 minutes at room temperature. The PRP layer was removed, transferred to a new tube, and the platelet count was adjusted, if necessary, to achieve a platelet concentration of ~3×10$^8$ platelets/mL using platelet-poor plasma (PPP). PPP was prepared by centrifugation of the remaining blood sample (after removal of PRP) for 20 minutes at 800×g. This preparation of PRP may be subsequently used for aggregation assays in either a 96-well plate or standard cuvette aggregometry.

Inhibition of Convulxin-induced aggregation was determined by cuvette light transmittance aggregation assays. Serial dilutions (1:2) of test compounds were prepared in 30% DMSO in a 96-well V-bottom plate (final DMSO concentration in the cuvette was 0.3%). The test compound (5 μl of serial dilutions in DMSO) was preincubated with PRP for 20 minutes prior to initiation of the aggregation reactions, which were performed in a ChronoLog aggregometer by addition of agonist (125-250 ng/mL Convulxin) to 495 μL of PRP at 37° C. The aggregation reaction was recorded for 4 minutes, and the maximum extent of aggregation was determined by the difference in extent of aggregation at baseline, compared to the maximum aggregation that occurred during the 4 minute period of the assay. Inhibition of aggregation was calculated as the maximum aggregation observed in the presence of inhibitor, compared to that in the absence of inhibitor. $IC_{50}$s were derived by non-linear regression analysis.

Example compounds 1-1, 1-2, 2-1, 2-2, 6-1, 7-1, 8-1, 8-2, 9-1, 10-1, 10-2, 11-1, 12-1, 13-1, 14-1, 15-1, 17-1, 18-1, 19-1, 20-1, 22-1, 22-2 and 25-1 were assayed for inhibition of convulxin-induced aggregation of platelet rich plasma by the cuvette light transmittance aggregation assay described above and were found to have $IC_{50}$ values of less than or equal to 50 μM.

Inhibition of Convulxin-induced aggregation may also be determined in 96-well flat-bottom microtiter plates using a microtiter plate shaker and plate reader similar to the procedure described by Frantantoni et al. (*Am. J. Clin. Pathol.* 94, 613, 1990). All steps are performed at room temperature. The total reaction volume of 0.2 mL/well includes 190 μl of PRP (~3×10$^8$ platelets/mL, see above), and 5 μl of either serial dilution of test compounds in 30% DMSO or buffer (for control wells). After a 20 minute preincubation at room temperature, 5 μl of 320 ng/mL Convulxin agonist solution is added to each well to give a final concentration of 8 ng/mL Convulxin. The plates are then agitated for 5 minutes on a microtiter plate shaker and the 5 minute reading is obtained in the microtitre plate reader (Softmax, Molecular Devices, Menlo Park, Calif.). Aggregation is calculated from the decrease of optical density (OD) at 650 nm at t=5 minutes. $IC_{50}$s may then be derived by non-linear regression analysis.

Inhibition of GPVI-Mediated Platelet Function In Vitro

The ability for candidate molecules to inhibit Syk-mediated platelet functions may be tested by measuring the inhibition of the GPVI-specific agonist Convulxin-induced human platelet calcium mobilization or aggregation. Calcium-mobilization is assessed in human washed platelets in a 96-well microtiter format. Aggregation is assessed in a 96-well microtiter assay (see generally the procedures in Jantzen, H. M. et al., *Thromb. Haemost.* 81: 111-117, 1999), or by standard cuvette light transmittance aggregometry using human platelet-rich plasma (PRP) as described above.

Inhibition of Convulxin-Mediated Platelet Calcium Mobilization In Vitro

Inhibition of Convulxin-induced calcium mobilization was determined in human washed platelets using the FLIPR Calcium 3 Assay Kit (Molecular Devices, Sunnyvale, Calif.). For preparation of washed platelets, human venous blood was collected from healthy, drug-free volunteers into ACD (85 mM sodium citrate, 111 mM glucose, 71.4 mM citric acid) containing $PGI_2$ (1.25 mL ACD containing 0.2 μM $PGI_2$ final; $PGI_2$ from Sigma, St. Louis, Mo.). Platelet-rich plasma (PRP) was prepared by centrifugation at 160×g for 20 minutes at room temperature. Washed platelets were prepared by centrifuging PRP for 10 minutes at 730×g and resuspending the platelet pellet in CGS (13 mM sodium citrate, 30 mM glucose, 120 mM NaCl; 2 mL CGS/10 mL original blood volume). The wash in CGS was repeated a second time, the platelets were collected by centrifugation at 730 g for 10 minutes and resuspended at a concentration of $3 \times 10^8$ platelets/mL in Hepes-Tyrode's buffer (10 mM Hepes, 138 mM NaCl, 5.5 mM glucose, 2.9 mM KCl, 12 mM $NaHCO_3$, pH 7.4). This platelet suspension was allowed to rest for 45 minutes at room temperature before use in calcium mobilization assays.

For 96-well plate calcium-mobilization experiments, equal volumes of $3 \times 10^8$ washed platelets/mL were incubated with equal volumes of Calcium-3 Assay Reagent A resuspended in 1× Hank's Balanced Salt Solution, pH 7.4, 20 mM Hepes buffer. The total reaction volume of 0.2 mL/well included $1.5 \times 10^8$/mL washed platelet/Calcium-3 Assay reagent A mix, 10 µM Eptifibatide (Millennium Pharmaceuticals Inc, Cambridge, Mass.) and serial dilutions (1:3) of test compounds in 0.75% DMSO. DMSO alone was added to 1 well of each 8 set to allow for a maximal calcium-mobilization reading. After a 20 minute preincubation at room temperature, the 96-well microplate reader was loaded into the FlexStation (Molecular Devices, Sunnyvale, Calif.). The FlexStation experimental conditions for measuring calcium mobilization were set up using SOFTMax Pro. The settings used were as follows: Fluorescence parameters-assay mode: flex, excitation 485 nM, 525 nM with a cut-off of 515 nM; Parameters—PMT sensitivity-6, pipette height 230 µl, read time 2 minutes and 40 seconds, read intervals 2 seconds, temperature-23-25° C. After 18 seconds of baseline reading, calcium mobilization was initiated by the addition of Convulxin to a final concentration of 125 ng/mL. Inhibition of calcium mobilization was calculated as the maximum response observed in the presence of inhibitor, compared to that in the absence of inhibitor. $IC_{50}$s were then derived by non-linear regression analysis.

Example compounds 1-1, 1-2, 2-2, 3-1, 4-1, 8-1, 8-2, 9-1 and 16-1 were assayed for inhibition of convulxin-mediated platelet calcium mobilization in vitro as described above and found to have $IC_{50}$ values of less than 1 µM.

Syk Activity in Intact Non-Hodgkin's Lymphoma Cell Lines

Intracellular phospho-flow cytometry may be used to test compound inhibition of Syk activity in intact non-Hodgkin's lymphoma cell lines Ramos and SUDHL-6. $10 \times 10^6$ cells in log phase growth are aliquoted; Syk kinase is activated by incubating cells for 10 minutes with 3 µg/ml antibody specific to the B-cell receptor. Directly following, cells are fixed in 1% paraformaldehyde for 5 minutes at room temperature, washed in phosphate buffered saline, and then permeablized by incubation for 2 hours in ice cold methanol. Cells are again washed in phosphate buffered saline, then incubated for 30 minutes with antibody specific for phosphorylated Erk (Y204) and BLNK (Y84), which are indicators of Syk kinase activity, and phosphorylated Syk (Y352), a measure of Src family kinase activity. All antibodies used may be purchased from BD Pharmingen (San Jose, Calif.). After incubation with antibodies, cells are again washed and subjected to flow cytometry.

Anti-Proliferative Effects on Non-Hodgkin's Lymphoma B Cell Lines

The anti-proliferative effects of compounds on non-Hodgkin's lymphoma B-cell lines SUDHL-4, SUDHL-6, and Toledo may also be assessed. SUDHL-4 and SUDHL-6 require B-cell receptor signaling for growth and survival, while the Toledo cell line (serving here as a negative control) does not. Cells are aliquoted into each well of a 96-well plate and incubated with increasing concentrations of compound for 72 hours, after which cell survival and proliferation is determined using the MTT assay (Chemicon International, Inc., Temecula, Calif.) following protocols supplied by the manufacturer.

Induction of Apoptosis in Non-Hodgkin's Lymphoma B Cell Lines

Induction of apoptosis in non-Hodgkin's lymphoma B-cell lines SUDHL-4, SUDHL-6, and Toledo may be assessed by measuring the apoptotis marker Caspase 3. Cells are incubated with 1, 3, or 10 µM compound for 24, 48, and 72 hours. At the conclusion of each time point, cells are processed for flow cytometry analysis using the Monoclonal Rabbit Anti-Active Caspase-3 Antibody Kit and related protocols (BD Pharmingen). Data may be presented as the percent of total cells undergoing apoptosis following incubation with compounds under the indicated conditions.

B Cell Activation

Syk activity is not only required for B-cell signaling, proliferation, and survival, as shown, but is also critical for cellular activation upon cross-linking of the B-cell receptor. B-cell activation leads to increased cell surface expression of several proteins involved in cell signaling, antigen presentation, and adhesion. Among these, CD80, CD86, and CD69 are commonly measured to determine B-cell activation status. Therefore, primary mouse B-cells isolated from spleen may be aliquoted and incubated with increasing concentrations of compound (0.05 to 2 µM) in the presence of goat anti-mouse IgD (eBiosciences, Inc., San Diego, Calif.) for 20 hours to cross-link the B-cell receptor. Following, cells are washed and incubated for 30 minutes on ice with antibodies specific for the CD80, CD86, and CD69 B-cell activation markers. B-cells are identified from the pooled population by staining with the B-cell marker CD45RO. All antibodies may be purchased from BD Pharmingen.

Calcium Flux Assay in Ramos Cells Induced by BCR Cross-Linking

Ramos cells (2G6.4C10, Burkitt's lymphoma, ATCC Item Number: CRL-1923) are sub-cultured at $5 \times 10^5$ cells/ml in fresh medium 3 or 4 days ahead of experiments. Cells are harvest and re-suspend in fresh medium at $8 \times 10^6$ cells/ml before dye-loading. An equal volume of Calcium 3 loading dye (Molecular Device) is added and mixed into cell suspension. Loading cells are dispensed in a 96 well plate and incubated 30 min. Compounds are then added in the dye-loaded cells and incubated for another 30 min., and spun down at 1000 rpm for 3 min before fluorescence measurement in FlexStation. BCR stimulation is carried out by the addition of 5 µg/ml antibody (AffiniPure F(ab')$_2$ fragment Donkey anti-human IgM, Jackson ImmunoResearch Laboraotries).

Calcium Flux Assay in Jurkat Cells Induced by TCR Cross-Linking

This protocol is very similar to B-cell calcium flux as described above. The only differences are that T cells (clone E6-1, Acute T cell Leukemia, ATCC Item Number: Tib-152) and anti-human CD3 (Functional Grade Purified anti-human CD3, clone OKT3, eBioscience, No. 16-0037) replace B-cells and anti-human IgM. Cell density is kept the same but antibody concentration is used at 100 ng/ml.

IL-2 Secretion in Jurkat Cells Induced by TCR Cross-Linking

Jurkat cell propagation and compound incubation procedures are the same as in Jurkat calcium flux assay as described above. Antibody (anti CD3, OKT3) is coated onto a fresh plate (without cells) at 100 ng/well. Cells are suspended at $8 \times 10^6$ cells/ml and incubated with compounds for 30 min in a separate plate. At the end of incubation, cells are transferred to the antibody-coated plate and incubated for 16 hours. 100 µl of cell medium after incubation is used for IL-2 measurement after incubation. IL-2 level is determined using an IL-2 ELISA kit (Human IL-2 ELISA kit II, BD Bioscience, No. 550611).

Inhibition of Platelet Clearance in a Mouse Model of Immune-Mediated Thrombocytopenia Immune-mediated thrombocytopenia is caused by antibodies directed against platelet surface glycoproteins, antibodies against drug-containing complexes on the platelet surface, or by antibody-coated cells or immune complexes that interact with the platelet surface. Compounds are evaluated for their ability to inhibit platelet clearance in a mouse model of antibody-mediated thrombocytopenia. In this model, a rapid clearance of circulating platelets (approximately 50%) results from the intravenous administration of a rat anti-mouse GPIIb (clone MWReg30) antibody (BD Biosciences, Pharmingen). To evaluate capacity for inhibition of platelet clearance, compounds are suspended into 0.5% methycellulose in water and administered via oral gavage (100 ul/mouse) at a time prior to antibody injection when the compound would achieve maximum plasma concentration (typically 1-2 hours). At 4 and 8 hours after injection of antibody, terminal blood samples are obtained from groups of vehicle and test article treated mice (n=5-10 mice/group) via cardiac puncture. Blood is anticoagulated using trisodium citrate or EDTA. Whole blood samples are measured for platelet counts on a hematology analyzer (Hemavet, Drew Scientific). Remaining blood is processed for plasma and compound concentrations measured by mass spectrometry. Platelet clearance is determined by measuring the difference in platelet number between the average non-antibody treatment group and animals administered the rat anti-mouse GPIIb antibody. Inhibition of platelet clearance is determined by comparing the difference between platelet clearance of vehicle and compound treated animals.

Inhibition of Inflammatory Response in a Mouse Model of Collagen Antibody Induced Arthritis The inhibitory activity of select compounds may be investigated in a mouse model of collagen antibody induced arthritis (CAIA). Collagen induced arthritis is mediated by autoantibodies to type II collagen and complement, thus arthritis can be induced by administration of polyclonal antibodies or a mixture of monoclonal antibodies to type II collagen. The CAIA model (Chondrex, Inc., Redmond, Wash.) uses a mixture of 4 clones which recognize individual epitopes clustered within an 83 amino acid peptide fragment of type II collagen. These epitopes share common amino acid sequences with many different species of type II collagen including chicken, mouse, rat, bovine, porcine, monkey and human. The model utilizes a monoclonal antibody cocktail followed by bacterial lipopolysaccharide (LPS) to induce a severe and consistent arthritis in mice within 7 days. This model was developed based on the hypothesis that bacterial toxins absorbed through the gastrointestinal tract play a synergistic and pathologic role with autoantibodies to type II collagen in triggering arthritis in patients with Rheumatoid Arthritis.

For these experiments, the monoclonal antibody cocktail (Lot # OC-708) is injected intravenously via tail vein at a dose of 4 mg/mouse (40 mg/ml) on day 0 followed by intraperitoneal injection of LPS diluted into normal saline at a dose of 25 ug/mouse in 8 week old, female Balb/C mice (Charles River, Inc.). Dosing of test articles is started just before or after the IV injection of antibody cocktail. Compounds are suspended into 0.5% methylcellulose in water and administered via oral gavage (100 ul/mouse) daily for the duration of the 7-10 day study. Clinical inflammation scores are obtained daily. Inhibition of clinical inflammation scores is determined based on the difference between vehicle and test article treated mice at the end of the experiment. Plasma concentrations represent peak concentration at 1 hour post last dose on the day of study termination.

JAK3/STAT6 Cellular Assay

Stimulation of Ramos B-cells by IL-4 leads to signaling through JAK1/JAK3 resulting in phosphorylation of STAT6 (signal transducers and activators of transcription). The effect of compounds on inhibition of JAK3 and/or JAK1 can be assessed by measuring the amount of phosphorylated STAT6. This may be performed by Western blotting and/or intracellular flow cytometry using a specific phospho-STAT6 antibody. Data describing compound inhibition of IL-4 induced STAT-6 phosphorylation (measured by intracellular flow cytometry) for Compound 1-1 (Example 1) is presented in the following table.

TABLE

| µM Cpd. 1-1 | % Inhibition |
| --- | --- |
| 2 | 49 |
| 1 | 41 |
| 0.5 | 33 |
| 0.25 | 22 |
| 0.125 | 6 |
| 0.05 | 0 |

For the data in the above Table, Ramos B-cells were pre-treated for 1 hour with increasing concentrations of Compound 1-1, as indicated prior to addition of IL-4. Cells were incubated with IL-4 for 10 minutes, and then subjected to intracellular flow cytometry to measure the percent inhibition of IL-4 induced Stat-6, as shown.

For Western blotting, Ramos B-cells are suspended in 10 mM Hepes-buffered RPMI media ($2 \times 10^7$ cells/ml). Cells (90 µl) are incubated with 10 µl 3.3 µg/ml interleukin 4 (R & D Systems Inc, cat #204-IL; final concentration: 0.33 µg/ml). Incubations are for 10 min at 37° C. in the absence or presence of 2 µl compound diluted in 30% DMSO. Reactions are terminated by the addition of an equal volume of 2× lysis buffer (100 mM TRIS-HCl pH 8.0, 2% Triton-X-100, 5 mM EDTA, 250 mM NaCl, 20% glycerol, 1.25 mM PMSF, 5 mM sodium orthovandate, 5 mM β-glycerophosphate, mini complete EDTA protease inhibitor cocktail (Sigma).

Samples are incubated with 1 µl of the nuclease, benzonase (Novagen, cat #71205-3) for 1 hour, room temperature and then 50 µl 5× loading buffer (330 mM TRIS pH 6.8, 9.5% SDS, 34% glycerol, 0.01% bromophenol blue, 10% beta-mercaptoethanol) is added.

Cell lysates (15 µL) are subjected to SDS-PAGE (Novex 4-12% TRIS-glycine gels, Invitrogen) under reducing conditions, followed by electroblot-transfer onto nitrocellulose membranes. Membranes are then incubated in Zymed blocking buffer (Invitrogen) for 1 hr at room temperature (RT) then overnight at 4° C. with 1:500 anti phosphotyrosine-STAT6 (Cell Signaling Technology, cat #9364) primary antibody in Zymed blocking buffer. Following 5×10 min washes with Tris-buffered saline, 0.25% NP40 (TBSN), blots are incubated for 1 hr at room temperature in the presence of 1:10,000 HRP-conjugated donkey anti-rabbit secondary antibody (Amersham Biosciences, cat #NA934V) in Zymed blocking buffer. After 4×10 min TBSN washes, blots are visualized by ECL (Pierce Western Lightening, Perkin Elmer cat #NEL101). In order to determine total β3 content, blots are stripped, washed 4× with TBSN, and re-probed with 1:2000 C3A antibody in block buffer overnight at 4° C. After 4×10 min TBSN washes, blots are incubated with 1:10,000 goat anti-mouse secondary antibody in blocking buffer, washed 4 more times with TBSN and exposed to Western Lightening reagent. Levels of stimulation over background and the extent of inhibition of compound are determined by densitometry.

Inhibition of JAK Kinase Activity Assay for Ramos B-cell Line Stimulated with IL-4

The in vitro and in vivo human JAK kinase activities of the inventive compounds may be evaluated by various procedures known in the art, such as a test for their ability to inhibit the activity of human plasma JAK kinase. The affinities for human JAK kinase inhibition exhibited by the inventive compounds can be measured by an $IC_{50}$ value (in nM). The $IC_{50}$ value is the concentration (in nM) of the compound required to provide 50% inhibition of human JAK kinase activity. The smaller the $IC_{50}$ value, the more active (potent) is a compound for inhibiting JAK kinase activity.

An in vitro assay for detecting and measuring inhibition activity against JAK kinase is as follows:

The activity of the compounds for JAK kinases is confirmed in cellular assays designed to test for JAK inhibition. Briefly, JAK inhibition is tested in human Ramos B-cells activated with cytokine IL-4. Twenty to 24 hours post stimulation, the cells are stained for upregulation of CD23 and analyzed by FACS. Stimulation of the B-cells with IL-4 leads to the activation of the JAK/STAT pathway through phosphorylation of the JAK kinase JAK1 and JAK3, which in turn phosphorylate and activate transcription of factors STAT-5 and STAT-6. The low-affinity IgE receptor (CD23) is upregulated by activated STAT-5.

For the assay, human Ramos B-cells (ATCC, Catalog No. CRL-1596) are cultured in RPMI 1640 medium (Cellgro, Catalog No. 10-040-CM) containing 10% fetal bovine serum (JRH, Catalog No 12106-500M) according to the propagation protocol supplied with the cells, and maintained at a density of approximately $3.5×10^5$ cells/ml. The day before the assay, the cells are diluted to $3.5×10^5$ cells/ml to insure they are in the logarithmic growth phase. The cells are spun down, and suspended in RPMI 1640 medium (Cellgro, MediaTech, Inc., Herndon, Va., Cat No. 10-040-CM) containing 5-10% fetal bovine serum (FBS), heat inactivated (JRH Biosciences, Inc, Lenexa, Kans., Cat No. 12106-500M) according to ATCC propagation protocol. Cells are maintained at a density of $3.5×10^{4-5}$ cells/ml. The day before the experiment, Ramos B-cells are diluted to $3.5×10^5$ cells/mL to ensure that they are in a logarithmic growth phase and aliquots dispensed into a 96-well tissue culture plate. Cells are incubated with test compound (dissolved in DMSO) or DMSO (control) for 1 hr at 37° C. and then stimulated with IL-4 (Pepotech, Catalog No. 200-04) for 20-24 hours (final concentration is 50 Units/ml).

Cells are spun down and suspended in RPMI with 5% serum. $5×10^4$ cells are used per point in a 96-well tissue culture plate. Cells are pre-incubated with compound or DMSO (Sigma-Aldrich, St. Louis, Mo., Catalog No. D2650) vehicle control for 1 hour in a 37° C. incubator. Cells are then stimulated with IL-4 (Peprotech Inc., Rocky Hill, N.J., Cat No. 200-04) for a final concentration of 50 units/mL for 20-24 hours. Cells are then spun down and stained with anti-CD23-PE (BD Pharmingen, San Diego, Calif., Catalog No. 555711) and analyzed by FACS. Detection is performed using a BD LSR I System Flow Cytometer, purchased from Becton Dickinson Biosciences of San Jose, Calif.

Primary Human T-cell Proliferation Assay Stimulated with IL-2

Primary human T-cells derived from peripheral blood and pre-activated through stimulation of the T-cell receptor and CD28 proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells are prepared as follows. Whole blood is obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface are recovered and washed twice with 5 volumes of PBS. The cells are resuspended in Yssel's medium (Gemini Bio-products, Woodland, Calif., Catalog #400-103) containing 40 U/mL recombinant IL2 (R and D Systems, Minneapolis, Minn., Catalog #202-IL (20 µg)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells are stimulated for 3 to 4 days, then transferred to a fresh flask and maintained in RPMI with 10% FBS and 40 U/mL IL-2.

Primary T-cells are washed twice with PBS to remove the IL-2 and resuspended in Yssel's medium at $2×10^6$ cells/mL. 50 µL of cell suspension containing 80 U/mL IL-2 is added to each well of a flat bottom 96 well black plate. For the unstimulated control, IL-2 is omitted from the last column on the plate. Compounds are serially diluted in dimethyl sulfoxide (DMSO, 99.7% pure, cell culture tested, Sigma-Aldrich, St. Louis, Mo., Catalog No. D2650) from 5 mM in 3-fold dilutions and then diluted 1:250 in Yssel's medium. 50 µL of 2× compound is added per well in duplicate and the cells are allowed to proliferate for 72 hours at 37° C.

ITP Material and Methods

Immune-mediated thrombocytopenia is caused by antibodies directed against platelet surface glycoproteins, antibodies against drug-containing complexes on the platelet surface, or by antibody-coated cells or immune complexes that interact with the platelet surface. Compounds may be evaluated for their ability to inhibit platelet clearance in a mouse model of antibody-mediated thrombocytopenia. In this model, a rapid clearance of circulating platelets (approximately 50%) results from the intravenous administration of a rat anti-mouse GPIIb (clone MWReg30) antibody (BD Biosciences, Pharmingen). To evaluate capacity of inhibition of platelet clearance, compounds are suspended into 0.5% methylcellulose in water and administered via oral gavage (100 ul/mouse) at a time prior to antibody injection when the compound would achieve maximum plasma concentration (typically 1-2 hours based on separate pharmacokinetic experiments for individual compounds). At 4 and 8 hours after injection of antibody, terminal blood samples are obtained from groups of vehicle and test article treated mice (n=5-10 mice/group) via cardiac puncture. Blood is anticoagulated using trisodium citrate or EDTA. Whole blood samples are measured for platelet counts on a hematology analyzer (Hemavet, Drew Scientific). Remaining blood is processed for plasma and compound concentrations measured by mass spectrometry.

Platelet clearance is determined by measuring the difference in platelet number between the average non-antibody treatment group and animals administered the rat anti-mouse GPIIb antibody. Inhibition of platelet clearance is determined by comparing the difference between platelet clearance of vehicle and compound treated animals.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (I):

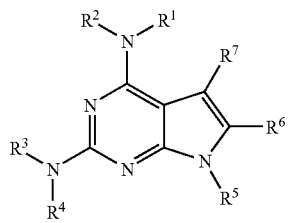

(I)

or a pharmaceutically acceptable salt thereof, wherein $R^1$ is structure (a), (b), (c) or (d):

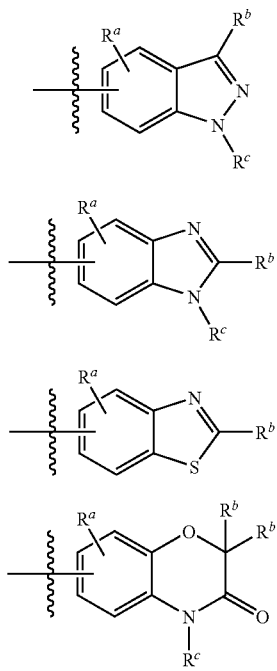

$R^a$ and $R^b$ are independently hydrogen, halogen, alkyl, aryl, heterocycle, —CN, —NO$_2$, —OR, —SR, —NRR, —C(=O)R —C(=O)OR, —NHC(=O)OR, or —SO$_2$NRR; and $R^c$ is hydrogen, alkyl, —S(O)R or —(SO$_2$)R;

R is, at each occurrence, independently hydrogen, alkyl, or aryl;

$R^2$ is hydrogen or alkyl;

$R^3$ is optionally substituted aryl or optionally substituted heterocycle;

$R^4$ is hydrogen or alkyl;

$R^5$ is hydrogen or lower alkyl; and $R^6$ and $R^7$ are independently hydrogen, halogen, cyano, lower alkyl, aryl or heterocycle.

2. The compound of claim 1 wherein $R^1$ is structure (a), and the compound has the following structure (II):

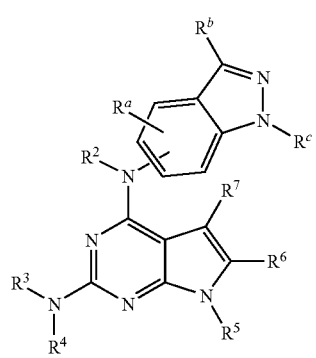

(II)

or a pharmaceutically acceptable salt thereof.

3. The compound of claim 1 wherein $R^1$ is structure (b), and the compound has the following structure (III):

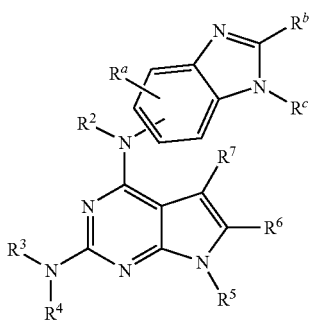

(III)

or a pharmaceutically acceptable salt thereof.

4. The compound of claim 1 wherein $R^1$ is structure (c), and the compound has the following structure (IV):

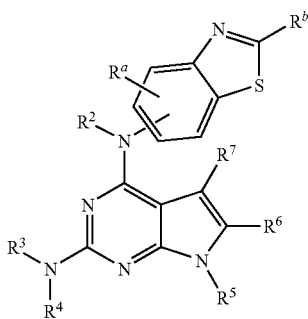

(IV)

or a pharmaceutically acceptable salt thereof.

5. The compound of claim 1 wherein $R^1$ is structure (d), and the compound has the following structure (V):

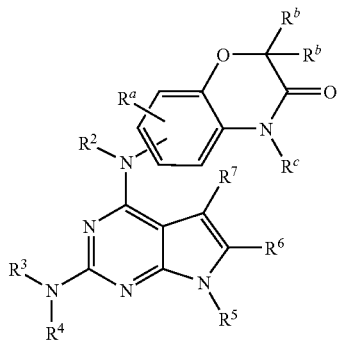

or a pharmaceutically acceptable salt thereof.

6. The compound of claim 2 wherein $R^a$, $R^c$, $R^2$, $R^4$, $R^5$ and $R^6$ are hydrogen, and the compound has the following structure (VI):

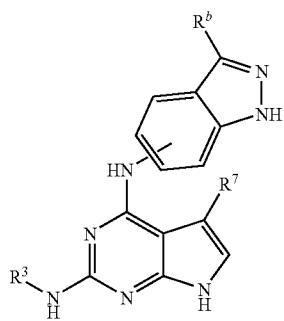

or a pharmaceutically acceptable salt thereof.

7. The compound of claim 3 wherein $R^a$, $R^c$, $R^2$, $R^4$, $R^5$ and $R^6$ are hydrogen, and the compound has the following structure (VII):

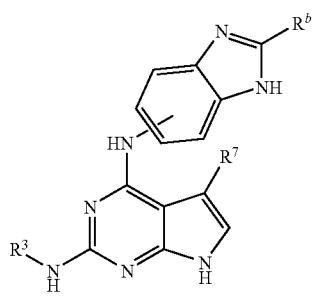

or a pharmaceutically acceptable salt thereof.

8. The compound of claim 4 wherein $R^a$, $R^c$, $R^2$, $R^4$, $R^5$ and $R^6$ are hydrogen, and the compound has the following structure (VIII):

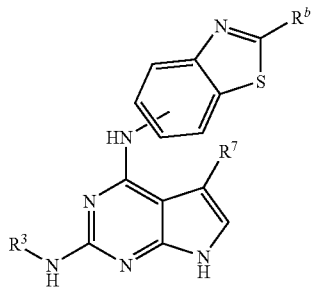

or a pharmaceutically acceptable salt thereof.

9. The compound of claim 5 wherein $R^a$, $R^c$, $R^2$, $R^4$, $R^5$ and $R^6$ are hydrogen, and the compound has the following structure (IX):

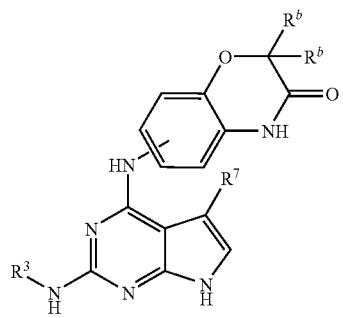

or a pharmaceutically acceptable salt thereof.

10. The compound of claim 1 wherein $R^3$ is an optionally substituted phenyl group, and the compound has the following structure (X):

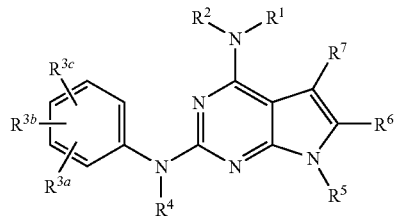

or a pharmaceutically acceptable salt thereof, wherein
$R^{3a}$, $R^{3b}$ and $R^{3c}$ are independently hydrogen, halogen, cyano, optionally substituted alkyl, optionally substituted aryl, optionally substituted heterocycle, —COOR$^8$, —COR$^8$, —CONR$^8{}_2$, —NR$^8$C(=O)R$^8$, —NR$^8$COOR$^8$, —OR$^8$, —SO$_n$R$^8$, —SO$_n$NR$^8{}_2$, —NR$^8$S(O)$_n$R$^8$, and —SO$_n$R$^9$, wherein
$R^8$ is, at each occurrence, independently hydrogen or an optionally substituted alkyl group;
$R^9$ is an optionally substituted heterocycle group; and
n is 0, 1 or 2; or
any two of $R^{3a}$, $R^{3b}$ and $R^{3c}$ when attached to adjacent atoms of the phenyl group are taken together with the carbon atoms to which they are attached to form an optionally substituted fused heterocylic ring, or an optionally substituted fused carbocyclic ring.

11. The compound of claim 10 wherein at least one of $R^{3a}$, $R^{3b}$ and $R^{3c}$ is:

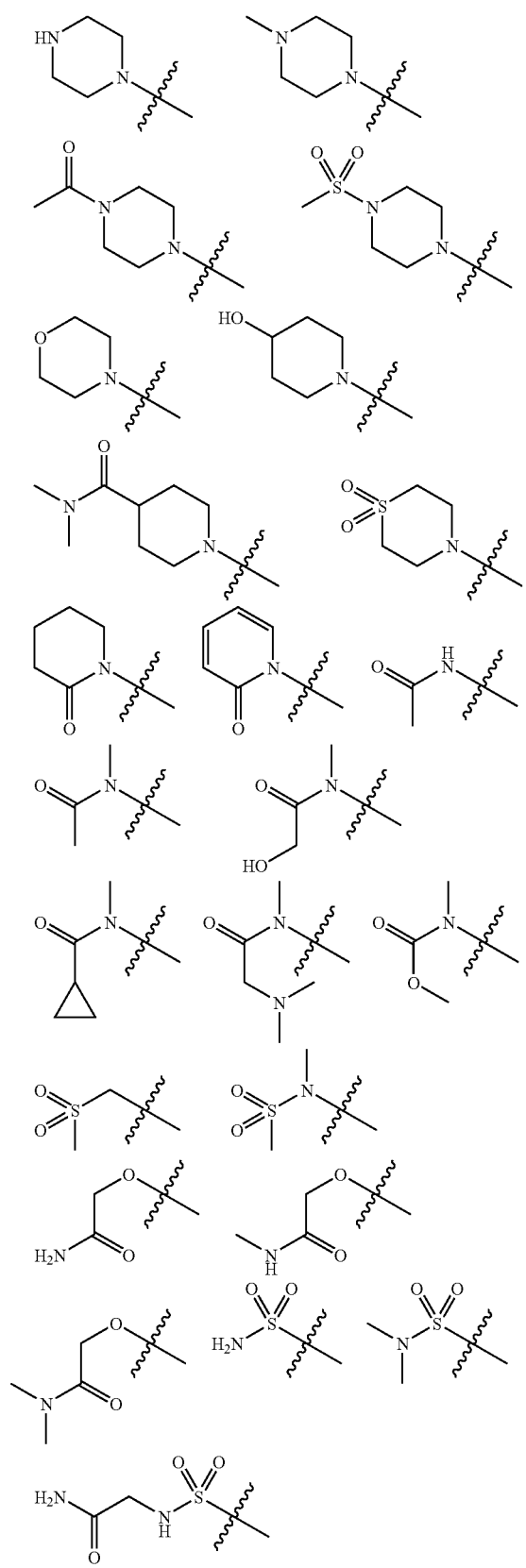
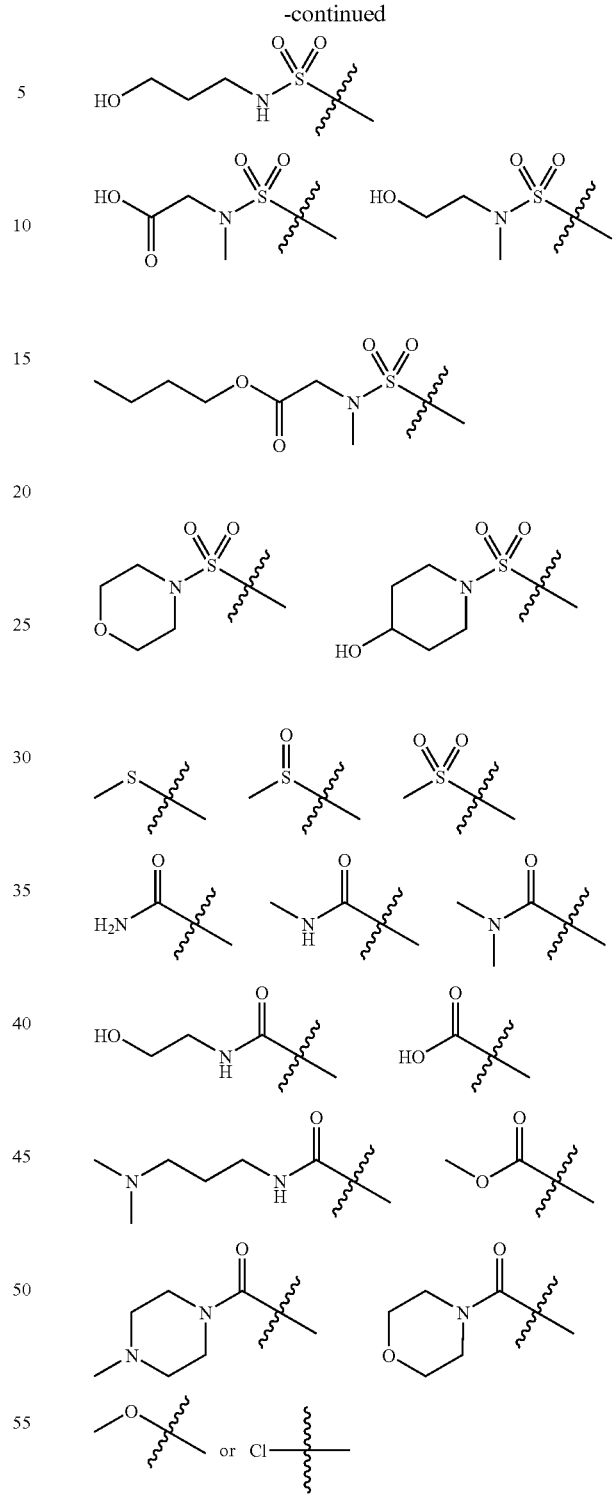

or a pharmaceutically acceptable salt thereof.

12. The compound of claim 10 wherein $R^{3b}$ and $R^{3c}$ are attached to adjacent atoms of the phenyl group and taken together with the carbon atoms to which they are attached to form an optionally substituted, fused heterocylic ring, or an optionally substituted, fused carbocyclic ring, and the compound has one the following structures (XI) or (XII):

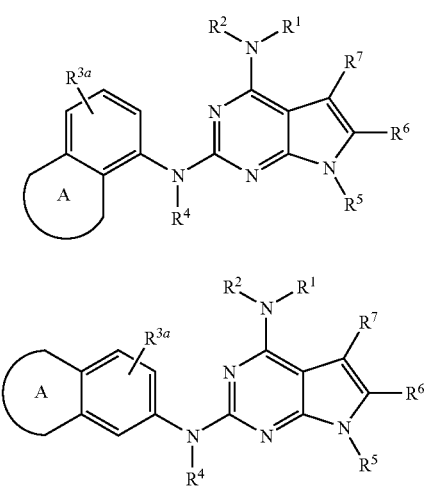
or a pharmaceutically acceptable salt thereof, wherein
A is an optionally substituted heterocyclic ring or an optionally substituted carbocyclic ring.
13. The compound of claim 12 wherein the group
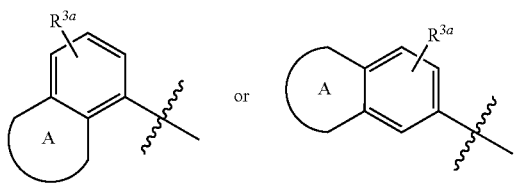
has the structure:
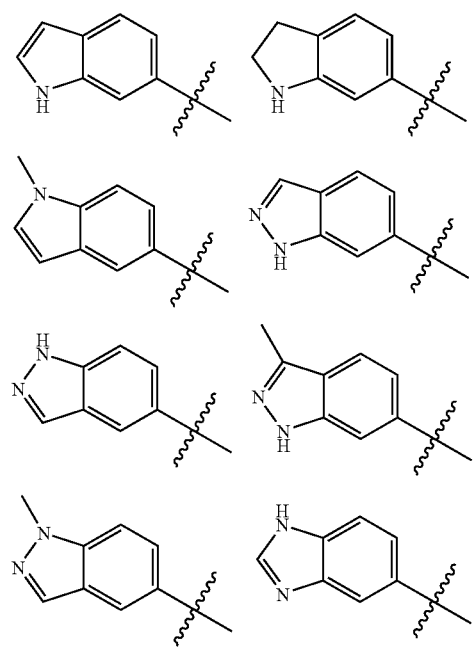
-continued
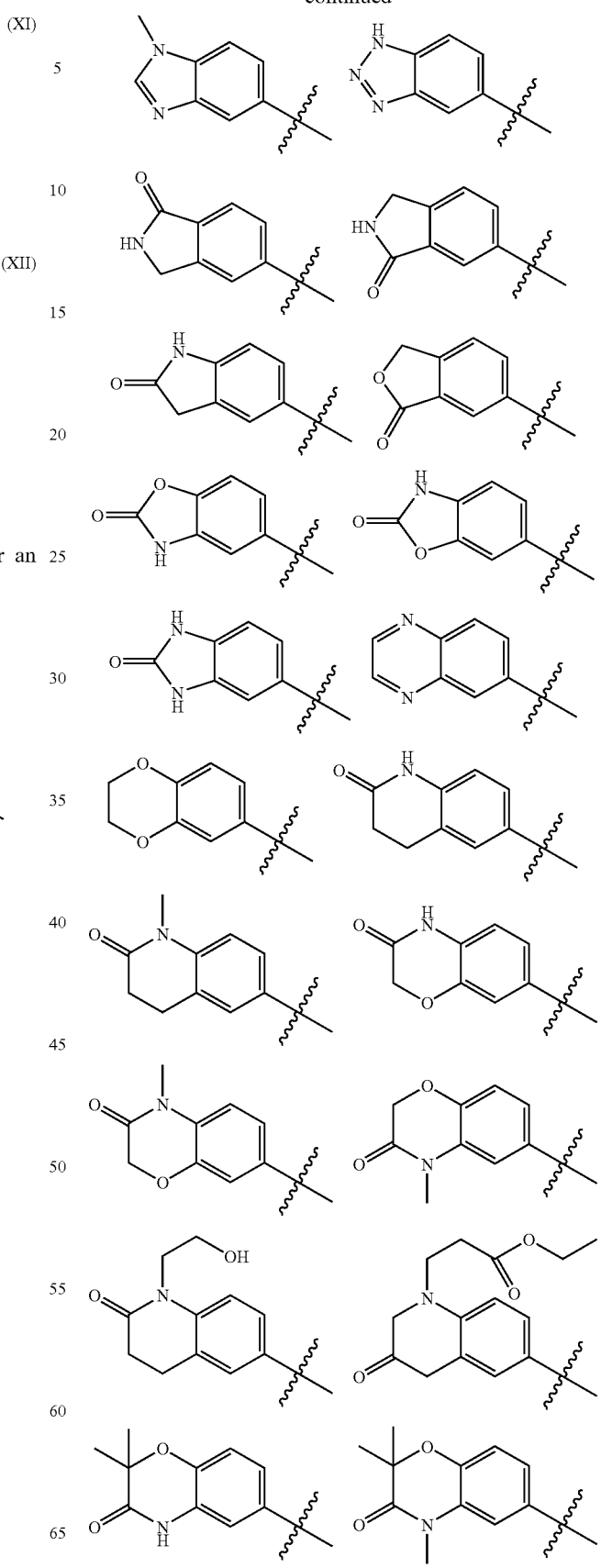

-continued

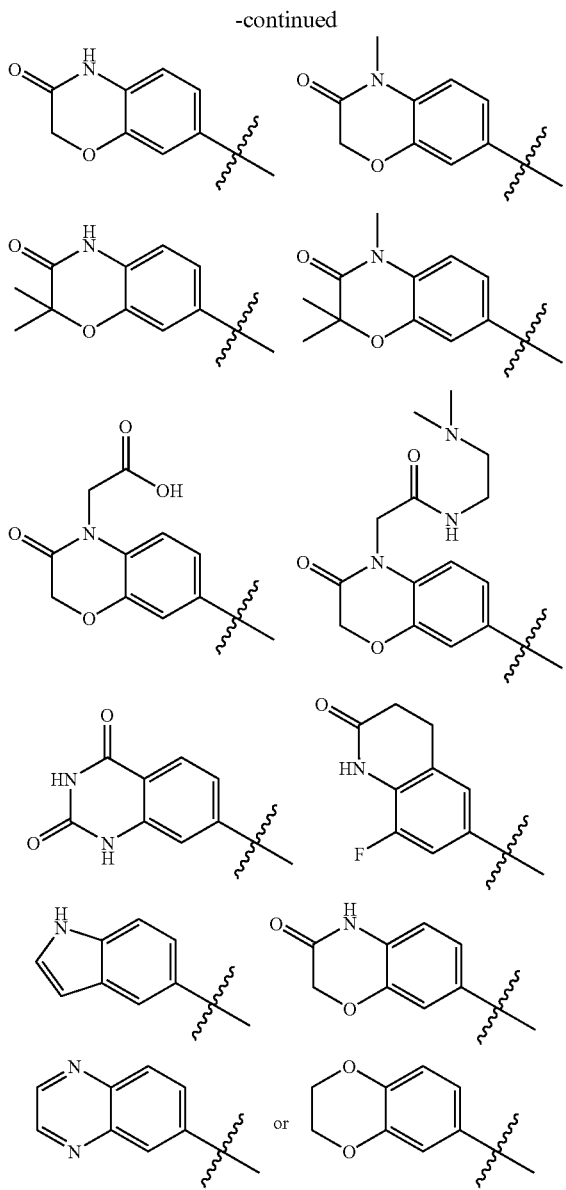

or a pharmaceutically acceptable salt thereof.

14. The compound of claim 1 wherein $R^3$ is an optionally substituted heterocycle group, and the compound has the following structure (XIII):

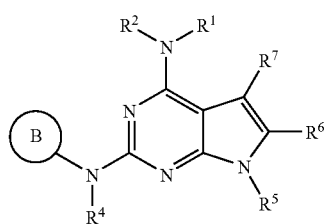

(XIII)

or a pharmaceutically acceptable salt thereof, wherein

B is the optionally substituted heterocycle group.

15. The compound of claim 14 wherein B is an optionally substituted pyridine group or an optionally substituted pyrimidine group.

16. The compound of claim 1 wherein the compound is: 1-(4-(4-(4-(1H-indazol-6-ylamino)-7H-pyrrolo[2,3-d]pyrimidin-2-ylamino)phenyl)piperazin-1-yl)ethanone, N4-(1H-indazol-6-yl)-N2-(4-(piperazin-1-yl)phenyl)-7H-pyrrolo[2,3-d]pyrimidine-2,4-diamine, 1-(4-(4-(4-(3-methyl-1H-indazol-6-ylamino)-7H-pyrrolo[2,3-d]pyrimidin-2-ylamino)phenyl)piperazin-1-yl)ethanone, N4-(3-methyl-1H-indazol-6-yl)-N2-(4-(piperazin-1-yl)phenyl)-7H-pyrrolo[2,3-d]pyrimidine-2,4-diamine, 6,6'-(7H-pyrrolo[2,3-d]pyrimidine-2,4-diyl)bis(azanediyl)bis(2,2-dimethyl-2H-benzo[b][1,4]oxazin-3(4H)-one, N2,N4-di(1H-indazol-6-yl)-7H-pyrrolo[2,3-d]pyrimidine-2,4-diamine, $N^4$-(1H-benzo[d]imidazol-6-ylamino)-$N^2$-(1H-indazoyl-6-yl)-7H-pyrrolo[2,3-d]pyrimidin-2,4-diamine, N-(4-(4-(1H-indazol-6-ylamino)-7H-pyrrolo[2,3-d]pyrimidin-2-ylamino)phenyl)-N-methylacetamide, 1-(4-(4-(1H-indazol-6-ylamino)-7H-pyrrolo[2,3-d]pyrimidin-2-ylamino)phenyl)piperidin-4-ol, N4-(1H-indazol-6-yl)-N2-(4-(4-(methylsulfonyl)piperazin-1-yl)phenyl)-7H-pyrrolo[2,3-d]pyrimidine-2,4-diamine, N4-(1-(methylsulfonyl)-1H-indazol-6-yl)-N2-(4-(4-(methylsulfonyl)piperazin-1-yl)phenyl)-7H-pyrrolo[2,3-d]pyrimidine-2,4-diamine, N4-(1H-indazol-6-yl)-N2-(4-(methylsulfonyl)phenyl)-7H-pyrrolo[2,3-d]pyrimidine-2,4-diamine, N4-(1H-indazol-6-yl)-N2-(4-(methylsulfinyl)phenyl)-7H-pyrrolo[2,3-d]pyrimidine-2,4-diamine, N4-(1H-indazol-6-yl)-N2-(4-(methylthio)phenyl)-7H-pyrrolo[2,3-d]pyrimidine-2,4-diamine, 4-(4-(1H-indazol-6-ylamino)-7H-pyrrolo[2,3-d]pyrimidin-2-ylamino)benzenesulfonamide, 4-(4-(1H-indazol-6-ylamino)-7H-pyrrolo[2,3-d]pyrimidin-2-ylamino)benzamide, N4-(1H-indazol-6-yl)-N2-(4-(4-methylpiperazin-1-yl)phenyl)-7H-pyrrolo[2,3-d]pyrimidine-2,4-diamine, 1-(4-(4-(4-(1H-indazol-5-ylamino)-7H-pyrrolo[2,3-d]pyrimidin-2-ylamino)phenyl)piperazin-1-yl)ethanone and N4-(1H-indazol-5-yl)-N2-(4-(piperazin-1-yl)phenyl)-7H-pyrrolo[2,3-d]pyrimidine-2,4-diamine, 1-(4-(4-(4-(1H-indazol-6-ylamino)-5-methyl-7H-pyrrolo[2,3-d]pyrimidin-2-ylamino)phenyl)piperazin-1-yl)ethanone, 6-(2-(1H-indazol-6-ylamino)-7H-pyrrolo[2,3-d]pyrimidin-4-ylamino)-2,2-dimethyl-2H-benzo[b][1,4]oxazin-3(4H)-one, N-(4-(4-(4-(H-benzo[d]imidazol-6-ylamino)-7H-pyrrolo[2,3-d]pyrimidin-2-ylaminophenyl)-N-methylacetamide, 1-(4-(4-(1H-benzo[d]imidazol-6-ylamino)-7H-pyrrolo[2,3-d]pyrimidin-2-ylaminophenyl)-N,N-dimethylpiperidine-4-carboxamide, N4-(benzo[d]thiazol-5-yl)-N2-(1H-indazol-6-yl)-7H-pyrrolo[2,3-d]pyrimidine-2,4-diamine, N4-(benzo[d]thiazol-6-yl)-N2-(1H-indazol-6-yl)-7H-pyrrolo[2,3-d]pyrimidine-2,4-diamine or 1-(4-(4-(4-(1H-indazol-6-ylamino)-5-ethyl-7H-pyrrolo[2,3-d]pyrimidin-2-ylamino)phenyl)piperazin-1-yl)ethanone, N4-(1-methyl-1H-indazol-6-yl)-N2-(4-(piperazin-1-yl)phenyl)-7H-pyrrolo[2,3-d]pyrimidine-2,4-diamine, 1-(4-(4-(4-(1-methyl-1H-indazol-6-ylamino)-7H-pyrrolo[2,3-d]pyrimidin-2-ylamino)phenyl)piperazin-1-yl)ethanone, 4-(4-(1-methyl-1H-indazol-6-ylamino)-7H-pyrrolo[2,3-d]pyrimidin-2-ylamino)benzamide, 6-(4-(1-methyl-1H-indazol-5-ylamino)-7H-pyrrolo[2,3-d]pyrimidin-2-ylamino)-3,4-dihydroquinolin-2(1H)-one, 4-(4-(1-methyl-1H-indazol-5-ylamino)-7H-pyrrolo[2,3-d]pyrimidin-2-ylamino)benzamide, 4-(4-(1H-indazol-4-ylamino)-7H-pyrrolo[2,3-d]pyrimidin-2-ylamino)benzamide, 1-(4-(4-(4-(1H-indazol-4-ylamino)-7H-pyrrolo[2,3-d]pyrimidin-2-ylamino)phenyl)piperazin-1-yl)ethanone, or a pharmaceutically acceptable salt thereof.

17. A composition comprising a compound of claim 1 in combination with a pharmaceutically acceptable carrier or diluent.

* * * * *